US011693011B2

(12) United States Patent
Ireton et al.

(10) Patent No.: US 11,693,011 B2
(45) Date of Patent: Jul. 4, 2023

(54) NEUTRALIZING ANTIBODY IMMUNOASSAYS

(71) Applicant: InBios International, Inc., Seattle, WA (US)

(72) Inventors: Gregory Ireton, Seattle, WA (US); Syamal Raychaudhuri, Seattle, WA (US); James Needham, Seattle, WA (US); Dindo Reyes, Seattle, WA (US)

(73) Assignee: InBios International, Inc., Seattle, WA (US)

( * ) Notice: Subject to any disclaimer, the term of this patent is extended or adjusted under 35 U.S.C. 154(b) by 0 days.

(21) Appl. No.: 17/527,016

(22) Filed: Nov. 15, 2021

(65) Prior Publication Data

US 2022/0244269 A1 Aug. 4, 2022

Related U.S. Application Data

(60) Provisional application No. 63/271,052, filed on Oct. 22, 2021, provisional application No. 63/270,020, filed on Oct. 20, 2021, provisional application No. 63/125,022, filed on Dec. 14, 2020.

(51) Int. Cl.
| | |
|---|---|
| *G01N 33/68* | (2006.01) |
| *A61K 39/215* | (2006.01) |
| *C07K 14/005* | (2006.01) |
| *C12N 9/02* | (2006.01) |
| *G01N 33/49* | (2006.01) |
| *G01N 33/52* | (2006.01) |
| *G01N 33/543* | (2006.01) |
| *G01N 33/58* | (2006.01) |
| *C12N 7/00* | (2006.01) |
| *C12Q 1/6897* | (2018.01) |

(52) U.S. Cl.
CPC ....... *G01N 33/6854* (2013.01); *A61K 39/215* (2013.01); *C07K 14/005* (2013.01); *C12N 9/0069* (2013.01); *G01N 33/49* (2013.01); *G01N 33/521* (2013.01); *G01N 33/54306* (2013.01); *G01N 33/581* (2013.01); *C12N 7/00* (2013.01); *C12N 2770/20022* (2013.01); *C12N 2770/20023* (2013.01); *C12N 2770/20034* (2013.01); *C12N 2770/20042* (2013.01); *C12N 2770/20044* (2013.01); *C12N 2770/20071* (2013.01); *C12N 2770/36121* (2013.01); *C12N 2770/36134* (2013.01); *C12N 2770/36143* (2013.01); *C12Q 1/6897* (2013.01); *G01N 2333/165* (2013.01)

(58) Field of Classification Search
None
See application file for complete search history.

(56) References Cited

U.S. PATENT DOCUMENTS

| 10,787,501 B1 | 9/2020 | Alina |
| 11,054,429 B1 | 7/2021 | Wang |
| 11,112,412 B1 | 9/2021 | Wang |
| 2021/0340225 A1 | 11/2021 | Grosveld |

FOREIGN PATENT DOCUMENTS

| EP | 3 800 473 A1 | 4/2021 |
| WO | 2021/180602 A1 | 9/2021 |
| WO | 2021/194423 A1 | 9/2021 |

OTHER PUBLICATIONS

Hofmann et al., Scientific Reports, Mar. 2022, 12(1):3549, 9 pages. (Year: 2022).*
Barnes C. et al. "Structures of Human Antibodies Bound to SARS-CoV-2 Spike Reveal Common Epitopes and Recurrent Features of Antibodies." Cell Jun. 25, 2020.
Du L., et al., "*The spike protein of SARS-CoV—a target for vaccine and therapeutic development*", Nat. Rev. Microbiol.7(3):226-36 (Mar. 2009).
Fu J., et al.. "*Expressions and significances of the angiotensin-converting enzyme 2 gene, the receptor of SARS-CoV-2 for COVID-19*", Mol. Biol. Rep. 1-10, May 14, 2020.
Hasan A., et al., "*A review on the cleavage priming of the spike protein on coronavirus by angiotensin-converting enzyme-2 and furin*", J. Biomol. Struct. Dyn., 1-9 (Apr. 22, 2020).
Kruse R., "*Therapeutic strategies in an outbreak scenario to treat the novel coronavirus originating in Wuhan, China*", F1000 Research 9:72 (2020).
Li, X., et al., "Molecular immune pathogenesis and diagnosis of COVID-19", Journal of Pharmaceutical Analysis, Mar. 2020 https://doi.org/10.1016/J.JPHA.2020.03.001.
Ni W., et al., "*Role of angiotensin-converting enzyme 2 (ACE2) in COVID-19*", 13 Crit. Care. 24(1):422 (2020).
Okba, N. M. A., et al., (2020). "Severe Acute Respiratory Syndrome Coronavirus 2-Specific Antibody Responses in Coronavirus Disease Patients", Emerging Infectious Diseases, 26(7), 2020.
Padoan A., et al., "*IgA-Ab response to spike glycoprotein of SARS-CoV-2 in patients with COVID-19: A longitudinal study*", Clin. Chim. Acta., 507:164-66 ( Apr. 2020).
Sandonis V., et al., "*Role of Neutralizing Antibodies in CMV Infection: Implications for New Therapeutic Approaches*", Trends Microbiol. 28(11):900-912 (Nov. 2020).
Sangster M., et al., "*Role of Memory B Cells in Hemagglutinin-Specific Antibody Production Following Human Influenza A Virus Infection*", Pathogens 8:167 (Sep. 28, 2019).
Stawicki S.P., et al., *The 2019-2020 Novel Coronavirus (Severe Acute Respiratory Syndrome Coronavirus 2) Pandemic: A Joint American College of Academic International Medicine—World Academic Council of Emergency Medicine Multidisciplinary COVID-19 Working Group Consensus Paper*, J. Glob. Infect. Dis., 12(2):47-93 (May 22, 2020).

(Continued)

*Primary Examiner* — Stacy B Chen
(74) *Attorney, Agent, or Firm* — Seed IP Law Group LLP

(57) ABSTRACT

The present disclosure provides compositions and methods for detecting the presence of neutralizing antibodies in a sample. Unlike conventional assays, the methods provided herein do not require the use of live virus or virus pseudoparticles to identify neutralizing antibodies.

17 Claims, 17 Drawing Sheets

Specification includes a Sequence Listing.

(56) References Cited

OTHER PUBLICATIONS

Tan, C.W. et al., "A SARS-CoV-2 surrogate virus neutralization test based on antibody-mediated blockage of ACE2-spike protein-protein interaction", *Nature Biotechnology*, vol. 38, Sep. 2020, pp. 1073-1078.

Walls A.C., et al., "*Structure, Function, and Antigenicity of the SARS-CoV-2 Spike Glycoprotein*", Cell. 180: 281-292, 6$^{th}$ Ed. (2020).

Wang, J.J. et al., "Rapid lateral flow tests for the detection of SARS-CoV-2 neutralizing antibodies", *Expert Review of Molecular Diagnostics*, 2021, 8 pages.

Wieland A. and Ahmed R., "*Fc Receptors in Antimicrobial Protection*", Curr. Top. Microbiol. Immunol. 423:119-150 (2019).

Wu, F., et al., "A new coronavirus associated with human respiratory disease in China", Nature, 579(7798), 265-269. https://doi.org/10.1038/s41586-020-2008-3, Feb. 2020.

Yan R., et al., "*Structural basis for the recognition of SARS-CoV-2 by full-length human ACE2*", Science 367:1444-48 (Mar. 4, 2020).

Zheng M. and Song L., "*Novel antibody epitopes dominate the antigenicity of spike glycoprotein in SARS-CoV-2 compared to SARS-CoV*", Cellular & Molecular Immunology. 17(5):536-538 (Mar. 2020).

Zhou P., et al., "*A pneumonia outbreak associated with a new coronavirus of probable bat origin*", Nature, 579(7798):270-73 (2020).

Ejemel, M., et al. "A cross-reactive human IgA monoclonal antibody blocks SARS-CoV-2 spike—ACE2 interaction," Nature Comm, 11(1): 1-9 (Dec. 1, 2020).

"Technical Data Sheet: Purified Mouse Anti-Human c-Myc with Control," BD Pharmingen™ (Jan. 1, 2008).

Ju, Bin, et al. "Human neutralizing antibodies elicited by SARS-CoV-2 infection," Nature 584(7819): 22 pages. (May 26, 2020).

"Manual SARS-CoV-2 Neutralizing Antibodies Detection Kit," Adipogen (Jul. 14, 2020).

McAndrews, K., et al., "Identification of IgG antibody response to SARS-CoV-2 spike protein and its receptor binding domain does not predict rapid recovery from COVID-19," medRxiv (May 6, 2020).

"CPass SARS-CoV-2 Neutralization Antibody Detection Kit," Genscript (Jan. 1, 2020).

International Search Report in PCT/US2021/063060 (dated May 31, 2022).

\* cited by examiner

| SCoV-2 NAb Detect™ | | | | |
|---|---|---|---|---|
| PRNT₈₀ | 640 | 160 | 20 | 0 |
| LFE | 0.02 | 0.21 | 1.34 | 2.16 |
| Result interpretation | Strong positive | Moderate positive | Weak positive | Negative |

Fig. 16

| Sample type | Sample loading volume (μL) | | |
|---|---|---|---|
| | 10 | 20 | 50 |
| Covid-19 vaccinated serum diluted 1:5 | C T | C T | C T |
| LFE | 0.25 | 0.35 | 0.11 |
| Naturally infected (Covid +, Strong) | C T | C T | C T |
| LFE | 0.14 | 0.12 | 0.20 |
| Naturally infected (Covid +, Weak) | C T | C T | C T |
| LFE | 0.75 | 0.76 | 0.59 |
| Pre-Covid NHS | C T | C T | C T |
| LFE | 0.87 | 1.33 | 1.80 |

Fig. 17

NEUTRALIZING ANTIBODY IMMUNOASSAYS

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is 480376_411_SEQUENCE_LISTING. The text file is 47.2 KB, was created on Mar. 19, 2022 and is being submitted electronically via EFS-Web.

TECHNICAL FIELD

The present disclosure relates generally to compositions, methods, devices, and kits for detecting neutralizing antibodies (nAbs). More specifically, the disclosure relates to detecting neutralizing antibodies for SARS-CoV-2.

BACKGROUND

The production of antibodies (Abs) that specifically bind to epitopes present on non-self antigens are a fundamental part of the immune response that assists in fighting off infections. The administration of antibodies against an infectious agent from an individual who has survived such an infection to a second individual who is currently infected or is at risk of infection has emerged as a method of assisting the immune response in the second individual. Some antibodies are more suitable than others for such therapeutic use, such as antibodies that are neutralizing for the infectious agent. See, e.g., Sandonis V., et al., *Role of Neutralizing Antibodies in CMV Infection: Implications for New Therapeutic Approaches*, Trends Microbiol. 28(11):900-912 (November 2020); Sangster M., Nguyen P., Topham D., *Role of Memory B Cells in Hemagglutinin-Specific Antibody Production Following Human Influenza A Virus Infection*, Pathogens 8:167 (Sep. 28, 2019); Wieland A. and Ahmed R., *Fc Receptors in Antimicrobial Protection*, Curr. Top. Microbiol. Immunol. 423:119-150 (2019). Neutralizing activity is typically generally able to prevent or reduce the efficiency of infection of the infectious agent.

Neutralizing antibodies may make up only a fraction of the antibodies generated in response to an infectious agent. As noted above, the ability to identify specific antibodies as having neutralizing activity is useful for selection of candidates for therapeutic use. In addition, the ability to detect the presence of antibodies having neutralizing activity in an individual who has an infection, has recovered from an infection, or has been vaccinated for an infectious agent is useful for diagnostic and prognostic purposes. Currently, the detection of neutralizing antibodies typically requires the use of live virus or pseudovirus in complicated cellular assays and highly trained personnel.

Coronavirus disease 2019 (COVID-19) is the infectious disease caused by the severe acute respiratory syndrome coronavirus 2 (SARS-CoV-2), an ongoing pandemic with alarming fatality that has resulted in more than 241 million cases in over 221 countries and an estimated more than 4.9 million deaths as of October, 2021. The US has emerged as the country with the largest caseload of COVID—at around 45.9 million cases and 746,415 deaths reported in all 50 states. SARS-CoV-2 is a highly infectious novel coronavirus which first emerged in a wild animal market in Wuhan, China in late 2019 and causes upper respiratory tract infections that can quickly precipitate into more serious conditions. (Zhou P., Yang X. L., Wang X. G., Hu B., Zhang L., Zhang W., et al., *A pneumonia outbreak associated with a new coronavirus of probable bat origin*, Nature, 579(7798): 270-73 (2020).) In high-risk group individuals comprising the elderly and persons with underlying conditions including immune deficiency, diabetes, heart ailments and asthma, SARS-CoV-2 infection can prove fatal while a majority of infected individuals, especially in the younger age groups remain asymptomatic or display mild symptoms. (Stawicki S. P., Jeanmonod R., Miller A. C., Paladino L., Gaieski D. F., Yaffee A. Q., et al., *The 2019-2020 Novel Coronavirus (Severe Acute Respiratory Syndrome Coronavirus 2) Pandemic: A Joint American College of Academic International Medicine-World Academic Council of Emergency Medicine Multidisciplinary COVID-19 Working Group Consensus Paper*, J. Glob. Infect. Dis., 12(2):47-93 (May 22, 2020).)

Although high effective vaccines are now available, they are generally less effective in many high-risk groups, such as the elderly and those with immune deficiency. In addition, not all vaccines are equally effective, particularly in some countries with limited vaccine access or the inability to consistently store and administer vaccines as intended.

Human angiotensin-converting enzyme 2 (ACE2) (SEQ ID NO:3; GenBank accession NP_001358344.1) is the established target receptor by which SARS-CoV-2 enters host cells. (Ni W., Yang X., Yang D., Bao J., Li R., Xiao Y., et al., *Role of angiotensin-converting enzyme 2 (ACE2) in COVID-19*, 13 Crit. Care. 24(1):422 (2020); Fu J., Zhou B., Zhang L., Balaji K. S., Wei C., Liu X., et al. *Expressions and significances of the angiotensin-converting enzyme 2 gene, the receptor of SARS-CoV-2 for COVID-19*, Mol. Biol. Rep. 1-10 May 14, 2020.) The first 615 amino acids of the ACE2 sequence form the ectodomain, which includes the peptidase domain (PD) and has been identified as binding both full-length SARS-CoV-2 Spike protein and Spike receptor binding domain (RBD) as effectively as full-length ACE2. (See Kruse R., *Therapeutic strategies in an outbreak scenario to treat the novel coronavirus originating in Wuhan, China*, F1000 Research 9:72 (2020).)

The SARS-CoV-2 receptor-binding protein is the trimeric Spike protein (also referred to as "S protein" or simply "S") expressed on the viral surface (SEQ ID NO:1; GenBank accession QHD43416). (Walls A. C., Park Y. J., Tortorici M. A., Wall A., McGuire A. T., Veesler D., *Structure, Function, and Antigenicity of the SARS-CoV-2 Spike Glycoprotein*, Cell. 16-181(2):281-292, 6$^{th}$ Ed. (2020).) All known coronaviruses express some type of S protein with varying degrees of sequence conservation. S protein is the chief architect of membrane fusion and host cell entry, by means of its binding to the ACE2 ectodomain on a target cell and subsequent processes that enable infection of the target cell (Id.). Each S protein contains an S1 subunit and an S2 subunit. The S1 subunit contains the RBD (SEQ ID NO:2; GenBank accession 6MOJ_E)), which directly binds to the PD of ACE2. (Hasan A., Paray B. A., Hussain A., Qadir F. A., Attar F., Aziz F. M., et al., *A review on the cleavage priming of the spike protein on coronavirus by angiotensin-converting enzyme-2 and furin*, J. Biomol. Struct. Dyn., 1-9 (Apr. 22, 2020).) During viral infection, the trimeric S protein is cleaved into S1 and S2 subunits and S1 subunits are released in the transition to the post fusion conformation, while the S2 subunits remain on the viral membrane and aid in fusion of the viral membrane with the host cell membrane. (Yan R., Zhang Y., Li Y., Xia L., Guo Y., Zhou Q., *Structural basis for the recognition of SARS-CoV-2 by full-length human ACE2*, Science 367:1444-48 (Nov. 19, 2020)) The S protein is highly antigenic, and it is against S protein that the bulk of the host antibody repertoire is targeted. (Padoan A., Sciacovelli L., Basso D., Negrini D., Zuin S., Cosma C., et al., *IgA-Ab response to spike glycoprotein of SARS-CoV-2 in patients with COVID-19: A longitudinal study*, Clin. Chim. Acta., 507:164-66 (August 2020); Du L., He Y., Zhou Y., Liu S., Zheng B. J., Jiang S., *The spike protein of SARS-CoV—a target for vaccine and therapeutic development*, Nat. Rev. Microbiol. 7(3):226-36 (March 2009); Zheng M., Song L., *Novel antibody epitopes dominate the antigenicity of spike glycoprotein in SARS-CoV-2 compared to SARS-CoV*, Cellular & Molecular Immunology. 17(5):536-38 (May 2020).)

The mechanism of SARS-CoV-2 binding to ACE2 and the mechanism of S protein binding to ACE2 outside of the SARS-CoV-2 context are almost indistinguishable and thereby implies that disruption of the S-ACE2 interaction would block SARS-CoV-2 cell entry. (Du, et al.)

A recent study examining neutralizing antibodies from recovered COVID-19 patients revealed that competition with ACE2, rather than antibody binding affinity for S, better predicts antibody potency; the most potent neutralizing antibodies were directly competitive with ACE2, indicating that blocking the S protein-ACE2 interaction can serve to neutralize the virus. (Id.) Current assays able to detect neutralizing antibodies, as opposed to all, or a large proportion of antibodies that bind a SARS-CoV-2 protein without neutralizing effect, involve either the use of live virus or pseudovirus in complicated cellular assays requiring highly trained personnel and, in some cases, potential infection hazards.

BRIEF SUMMARY

The present disclosure provides an enzyme-linked immunosorbent assay (ELISA) method of detecting antibodies that are neutralizing for SARS-CoV-2 Spike protein binding to human angiotensin-converting enzyme 2 (ACE2), the method comprising: combining full-length SARS-CoV-2 Spike protein ectodomain with a strep tag protein label at one terminus and an anti-strep tag protein label antibody bound to the strep tag with a sample comprising antibodies to form a mixture; incubating the mixture with a human ACE2 protein ectodomain bound to a substrate for a length of time sufficient to allow the full-length SARS-CoV-2 Spike protein to bind the human ACE2 protein ectodomain; incubating the substrate with a detection antibody that specifically binds a constant region of the anti-strep tag protein label antibody and comprises an enzymatic detection label for a length of time sufficient for the detection antibody to bind to the anti-strep tag protein label antibody; washing the substrate to remove SARS-CoV-2 Spike protein ectodomain with a strep tag protein at one terminus, anti-strep tag protein label antibody, and detection antibody not bound to the human ACE2 protein ectodomain; incubating the substrate with an enzymatic substrate for the enzymatic detection label for a length of time sufficient for the enzymatic detection label to catalyze a reaction with the enzymatic substrate to produce a fluorescent or color reaction product; and measuring the amount of anti-strep tag protein label antibody associated with the substrate as compared to a negative control by measuring the amount of a fluorescent or color reaction product; wherein a reduced amount of fluorescent or color reaction product as compared to the negative control indicates the presence of antibodies that are neutralizing for SARS-CoV-2 Spike protein binding to human ACE2.

According to further embodiments of the above method, which may be combined with one another and any other portions of the present disclosure:

the full-length Spike protein ectodomain comprises the amino acid sequence according to SEQ ID NO:1;

the strep tag comprises the amino acid sequence according to SEQ ID NO: 6 or SEQ ID NO: 7;

the full-length SARS-CoV-2 Spike protein ectodomain with a strep tag protein label at one terminus is a fusion protein comprising the full-length SARS-CoV-2 Spike protein ectodomain and the strep tag protein label, more particularly, the fusion protein comprises the amino acid sequence according to SEQ ID NO: 4;

the human ACE2 protein ectodomain comprises the amino acid sequence according to SEQ ID NO: 3;

the human ACE2 protein ectodomain in comprised in an ACE2-Fc fusion protein that further comprises an immunoglobulin constant region (Fc), more particularly, the ACE2-Fc fusion protein comprises the amino acid sequence according to SEQ ID NO: 5;

measuring the amount of a reaction product resulting from action of the enzymatic detection label on the enzymatic substrate comprises measuring an optical density;

the sample is blood, serum, or plasma;

the method further comprising diluting the sample 1:20 with a buffer comprising the full-length SARS-CoV-2 Spike protein ectodomain with a strep tag protein label at one terminus and an anti-strep tag protein label antibody;

the method further comprising washing the substrate between incubating the mixture with the human ACE2 protein ectodomain and incubating the human ACE2 protein ectodomain bound to a substrate with the detection antibody to remove SARS-CoV-2 Spike protein ectodomain with a strep tag protein at one terminus, and anti-strep tag protein label antibody not bound to the human ACE2 protein ectodomain;

the method further comprising adding a stop reagent to the substrate between adding the enzymatic substrate and measuring the amount of the fluorescent or color reaction product resulting from the action of the enzymatic detection label on the enzymatic substrate;

the anti-strep tag protein label antibody comprises a constant region of the IgG1 isotype, the detection antibody comprises an anti-IgG1 antibody, the detection label comprises horseradish peroxidase (HRP), the enzymatic substrate comprises a colorimetric HRP substrate, and measuring the amount of a fluorescent or color reaction product comprises measuring optical density of the sample and at a wavelength of 450 nm ($OD_{450}$) to obtain a sample OD, and the method further comprising measuring $OD_{450}$ of the negative control to obtain a negative control OD, more particularly the method further comprising calculating a signal inhibition percent (SI %) for the sample using the following formula: SI %=(1−(sample OD÷negative control OD))×100%, even more particularly, if the SI % is greater than 25%, the sample is positive for antibodies that are neutralizing for SARS-CoV-2 Spike protein binding to human ACE2, if the SI % is between 15% and 25%, the sample is inconclusive for antibodies that are neutralizing for SARS-CoV-2 Spike protein binding to human ACE2, and, if the SI % is less than 15%, the sample is negative for antibodies that are neutralizing for SARS-CoV-2 Spike protein binding to human ACE2. If the SI % is between 15% and 25%, such that the sample is inconclusive, the method may be repeated again using the same sample.

The present disclosure further provides a kit, which may be used in any of the above methods, for performing an enzyme-linked immunosorbent assay (ELISA) to detect antibodies that are neutralizing for SARS-CoV-2 Spike protein binding to human ACE2, the kit comprising: a human angiotensin-converting enzyme 2 (ACE2) protein ectodomain bound to a substrate; a full-length SARS-CoV-2 Spike protein ectodomain with a strep tag protein label at one terminus; an anti-strep tag protein label antibody that specifically binds the strep tag protein label; and a detection antibody that specifically binds a constant region of the anti-strep tag protein label antibody and comprises an enzymatic detection label.

According to further embodiments of either of the above methods, which may be combined with one another and any other portions of the present disclosure:

the full-length Spike protein ectodomain comprises the amino acid sequence according to SEQ ID NO:1;

the strep tag comprises the amino acid sequence according to SEQ ID NO: 6 or SEQ ID NO: 7;

the full-length SARS-CoV-2 Spike protein ectodomain with a strep tag protein label at one terminus is a fusion protein comprising the full-length SARS-CoV-2 Spike protein ectodomain and the strep tag protein label, more particularly, the fusion protein comprises the amino acid sequence according to SEQ ID NO: 4;

the anti-strep tag protein label antibody comprises a constant region of the IgG1 isotype, the detection antibody comprises an anti-IgG1 antibody, and the detection label comprises horseradish peroxidase (HRP), more particularly, the kit further comprising a colorimetric HRP substrate;

the human ACE2 protein ectodomain comprises the amino acid sequence according to SEQ ID NO: 3;

the human ACE2 protein ectodomain is comprised in an ACE2-Fc fusion protein that further comprises an immunoglobulin constant region (Fc) more particularly, the ACE2-Fc fusion protein comprises the amino acid sequence according to SEQ ID NO: 5;

the substrate comprises a well of a plate and the kit further comprises the plate; and the kit further comprising a negative control and a positive control.

The present disclosure provides an ELISA assay comprising an human ACE2 protein ectodomain bound to a substrate, a SARS-CoV-2 Spike protein with a protein label at one terminus, a protein label antibody that specifically binds the protein label, and a detection label associated with the protein label antibody.

According to further embodiments, which may be combined with one another and any other portions of the present disclosure:

the tagged Spike protein comprises full-length Spike protein ectodomain;

the full-length Spike protein ectodomain comprises the amino acid sequence according to SEQ ID NO:1;

the protein label is a strep tag;

the Spike protein with a protein label is a Spike-strep tag fusion protein;

the Spike-strep tag fusion protein comprises the amino acid sequence according to SEQ ID NO: 4;

the assay further comprising a detection antibody that specifically binds a constant region of the protein label antibody and comprises the detection label;

the protein label antibody is an IgG1 antibody, the detection antibody is an anti-IgG1 antibody, and the detection label is horseradish peroxidase (HRP);

the assay further comprising a colorimetric HRP substrate;

the colorimetric HRP substrate is 3,3',5,5'-tetramethylbenzidine;

the ELISA is plate based and the ACE2 ectodomain is bound to at least one well in a plate.

The present disclosure provides an ELISA assay comprising an human ACE2 protein ectodomain bound to a substrate and a SARS-CoV-2 Spike protein with a non-protein label.

According to further embodiments, which may be combined with one another and any other portions of the present disclosure:

the tagged Spike protein comprises full-length Spike protein ectodomain;

the full-length Spike protein ectodomain comprises the amino acid sequence according to SEQ ID NO:1;

the non-protein label is a gold particle;

the non-protein label is a gold nanoparticle;

the Spike protein is absorbed onto the gold particle;

the ELISA is plate based and the ACE2 ectodomain is bound to at least one well in a plate.

The present disclosure further provides a method of detecting antibodies that are neutralizing for SARS-CoV-2 Spike protein binding to human ACE2. The method may be used with any ELISA assay disclosed above. The method comprises: a) combining a SARS-CoV-2 Spike protein with a protein label at one terminus with a sample comprising antibodies and a protein label antibody to form a mixture; b) exposing the mixture to a human ACE2 protein ectodomain bound to a substrate; c) incubating the mixture with the human ACE2 protein ectodomain for a length of time sufficient to allow the SARS-CoV-2 Spike protein to bind the human ACE2 protein ectodomain (if not prevented from doing so by a nAb); d) washing the substrate; and e) measuring the amount protein label antibody associated with the substrate as compared to a negative control; wherein a reduced amount of protein label antibody associated with the substrate as compared to a negative control indicate the presence of antibodies that are neutralizing for SARS-CoV-2 Spike protein binding to human ACE2. The assay may optionally further include a step between steps d) and f) of incubating the substrate with a detection antibody that specifically binds a constant region of the protein label antibody then washing the substrate.

The present disclosure additionally provides a method of detecting antibodies that are neutralizing for SARS-CoV-2 Spike protein binding to human ACE2 using the second ELISA described above. The method comprises: a) combining a SARS-CoV-2 Spike protein with a non-protein label with a sample comprising antibodies to form a mixture; b) exposing the mixture to human ACE2 protein ectodomain bound to substrate; c) incubating the mixture with the human ACE2 protein ectodomain for a length of time sufficient to allow the SARS-CoV-2 Spike protein to bind the human ACE2 protein ectodomain (if not prevented from doing so by a nAb); d) washing the substrate; and e) measuring the amount of the non-protein label associated with the substrate as compared to a negative control; wherein a reduced amount of non-protein label associated with the substrate as compared to a negative control indicate the presence of antibodies that are neutralizing for SARS-CoV-2 Spike protein binding to human ACE2. The assay may optionally further include a step between steps d) and f) of incubating the substrate with a detection antibody that specifically binds a constant region of the protein label antibody then washing the substrate.

According to further embodiments of either of the above methods, which may be combined with one another and any other portions of the present disclosure:

the tagged Spike protein comprises full-length Spike protein ectodomain;

the full-length Spike protein ectodomain comprises the amino acid sequence according to SEQ ID NO:1;

the protein tag is a strep tag;

the Spike protein with a protein label is a Spike-strep tag fusion protein;

the Spike-strep tag fusion protein comprises the amino acid sequence according to SEQ ID NO: 4;

the SARS-CoV-2 Spike protein with a protein label at one terminus is first combined with the sample comprising antibodies and then with the protein label antibody to form the mixture;

the SARS-CoV-2 Spike protein with a protein label at one terminus is first combined with the protein label antibody and then with the a sample comprising antibodies to form a mixture;

the a SARS-CoV-2 Spike protein with a protein label at one terminus, the sample comprising antibodies, and the protein label antibody are combined simultaneously to form a mixture;

further comprising exposing the mixture or the substrate after exposure to the mixture to a detection antibody that specifically binds a constant region of the protein label antibody and comprises the detection label;

the protein label antibody is an IgG1 antibody, the detection antibody is an anti-IgG1 antibody, and the detection label is horseradish peroxidase (HRP);

further comprising a colorimetric HRP substrate;

the colorimetric HRP substrate is 3,3',5,5'-tetramethylbenzidine;

the mixture or the substrate after exposure to the mixture is exposed to the detection antibody after washing, and the substrate is washed again after exposure to the detection antibody;

the ACE2 ectodomain is bound to at least one well in a plate;

measuring the amount protein label antibody associated with the substrate comprises measuring an optical density of the substrate;

the sample is blood, serum, or plasma;

the non-protein tag is a gold particle, particularly a gold nanoparticle.

The present disclosure further provides a kit for detection of antibodies that are neutralizing for SARS-CoV-2 Spike protein binding to human ACE2, the kit comprising at least an ectodomain of human ACE2 protein bound to a substrate, a SARS-CoV-2 Spike protein with a protein label at one terminus, and a protein label antibody.

According to further embodiments, which may be combined with one another and any other portions of the present disclosure the kit further comprises one or more of an ELISA plate, sample buffer, a wash buffer, a detection reagent, a stop reagent, a detection antibody, a negative control, and a positive control.

The present disclosure further provides a lateral flow assay comprising: a nitrocellulose membrane; a sample pad resting on the nitrocellulose membrane at a sample end; a conjugate pad resting on the nitrocellulose membrane in a direction of sample flow after the sample pad and comprising a SARs-CoV-2 spike protein labeled with colloidal gold and a control antibody that specifically binds a control target protein and is labelled with colloidal gold; a bridge pad resting on the nitrocellulose membrane in a direction of sample flow after the conjugate pad; a test line and a control line on the nitrocellulose membrane both in a direction of sample flow after the bridge pad, wherein the test line comprises a human ACE2 protein ectodomain bound to the nitrocellulose membrane and the control line comprises the control target protein bound to the nitrocellulose membrane; and an absorbent pad in a direction of sample flow after the conjugate pad.

According to further embodiments, which may be combined with one another and any other portions of the present disclosure:

the tagged Spike protein comprises full-length Spike protein ectodomain;

the full-length Spike protein ectodomain comprises the amino acid sequence according to SEQ ID NO:1;

further comprising a lateral flow assay cassette in which the nitrocellulose membrane, pads, and test lines are housed.

The disclosure further provides a method of detecting antibodies that are neutralizing for SARS-CoV-2 Spike protein binding to human ACE2, the method comprising: a) placing a sample comprising antibodies on the sample pad of an assay according to any lateral flow assay disclosed above or elsewhere herein; b) allowing the sample to remain on the assay for a period of time sufficient for the sample to flow over the test line and the control line and for SARS-CoV-2 Spike protein in the sample to bind to human ACE2 in the test line; and c) viewing the test line and the control line to determine if the control line is visible, indicating a valid assay, and if the test line is visible, indicating an absence or limited amount of neutralizing antibodies in the sample.

According to further embodiments, which may be combined with one another and any other portions of the present disclosure:

further comprising placing a chase buffer on the sample pad after the sample;

further comprising determining the intensity of the test line to provide a semi-quantitative of quantitative measure of neutralizing antibodies in the sample;

comprising determining the intensity of the test line using a reader; the reader comprises a camera and a smartphone app comprising an artificial intelligence component;

further comprising displaying a neutralizing antibody result of the method to a user;

further comprising providing a code corresponding to a neutralizing antibody result of the method to a second reader;

determining the intensity of the test line using a reader comprises: obtaining one or more first images of a lateral flow assay cassette used to perform the method; aligning the cassette including by overlaying a semi-transparent reference of the lateral flow assay device on the one or more first images; presenting the one or more overlaid images to a user in real time as the one or more first images are being obtained; employing a first artificial intelligence mechanism to determine a position of the lateral flow assay cassette in the one or more first images relative to the transparent reference; responsive to the position of the lateral flow assay cassette being in an acceptable position relative to the semi-transparent reference in at least one of the one or more first images: capturing a second image of the lateral flow assay cassette; employing a second artificial intelligence mechanism on the second image to determine if a result of the lateral flow assay cassette is valid; responsive to the result of the lateral flow assay cassette being invalid, presenting an invalid-test-result notification to the user; responsive to the result of the lateral flow assay cassette being valid, employing a third artificial intelligence mechanism on the second image to determine the presence or absence of and/or semi-quantitative or quantitative amount of neutralizing antibody in the sample; and presenting the presence or absence of and/or semi-quantitative or quantitative amount of neutralizing antibody in the sample result to the user;

employing a third artificial intelligence mechanism on the second image may comprise: determining the intensity of the control line by analytical methods comprising integrating grayscale images around the control line and determining the peak value present in the control line; determining the intensity of the test line by analytical methods comprising integrating grayscale images around the test line and determining the peak value present in the test line; determining the ratio of the test line peak value to the control line peak value; and using the determined ratio to present the presence or absence of and/or a semi-quantitative or quantitative amount of neutralizing antibody in the sample result to the user.

BRIEF DESCRIPTION OF THE DRAWINGS

Figures herein are not to scale.

As shown in FIG. 2A, an internal structure of a lateral flow assay cassette contains various components, including pads and test and control lines along a path of fluid flow. As shown in FIG. 2B, nAb-dependent binding of ACE2 to gold-labelled S protein is detected at a control line.

FIG. 16 depicts representative images captured by a smartphone app of SARS-CoV-2 lateral flow assay cassettes according to the present disclosure along with PRNT titers, LFE values, and interpreted results.

FIG. 17 depicts the effects of sample loading volume on results with SARS-CoV-2 lateral flow assay cassettes according to the present disclosure.

DETAILED DESCRIPTION

Figure 1:
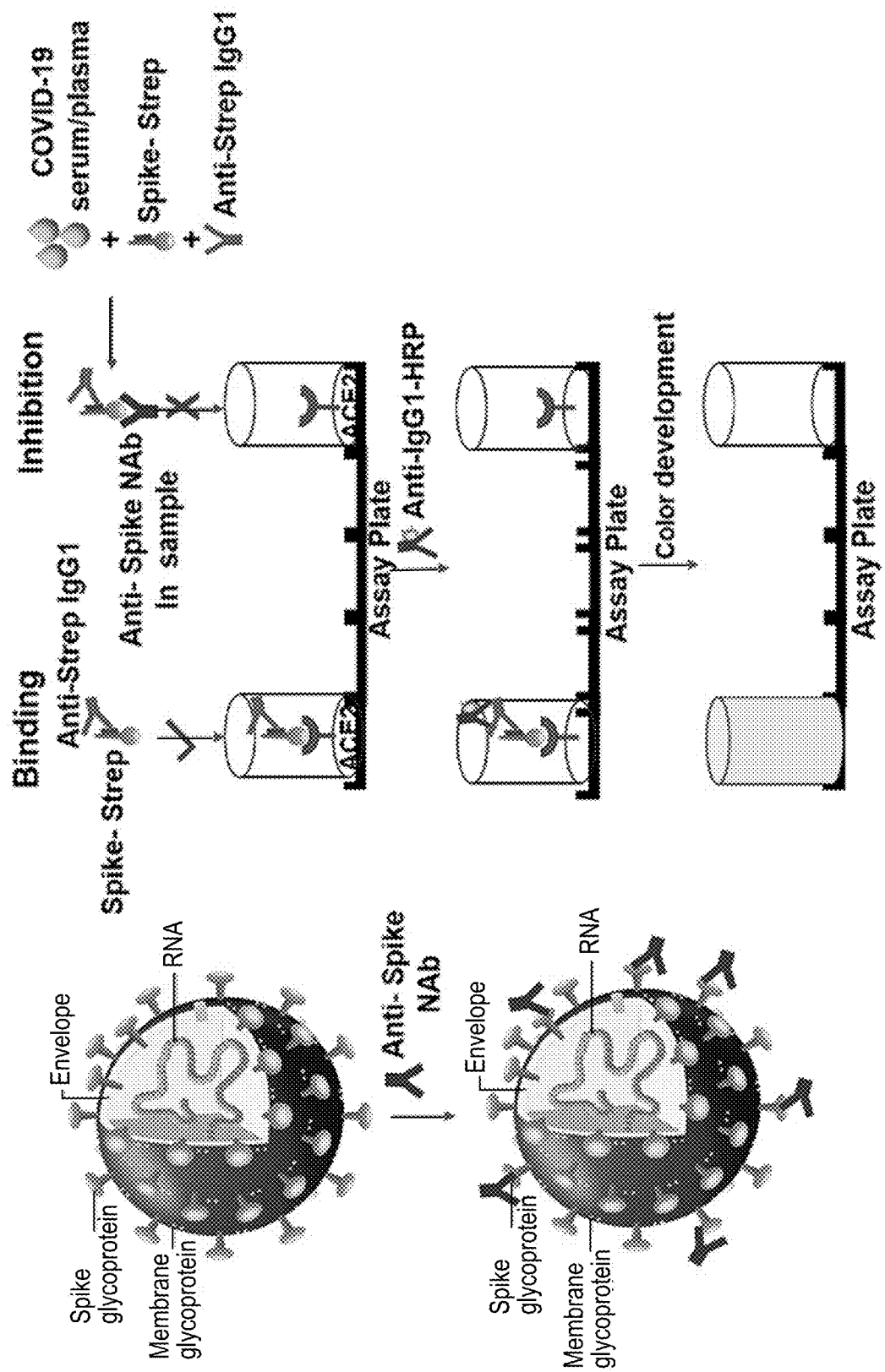
FIG. 1 depicts an exemplary embodiment of an ELISA-based neutralizing antibody detection assay, as provided herein. As shown on the left side of FIG. 1, the SARS-CoV-2 virus surface is covered by Spike protein trimers that are important for host cell infection. As shown on the right side of FIG. 1, from top to bottom: recombinant ACE2 is coated on wells to which recombinant S-Strep fusion is added in the presence of anti-Strep IgG; nAb-dependent binding of ACE2 to S is detected by an anti-IgG antibody conjugated to horseradish peroxidase (HRP); and the OD450 nm for color intensity is used as a measure of S protein-ACE2 binding levels, which can be interpreted in terms of binding inhibition in the presence of Nabs.

A major gap in the current diagnostic approach to infectious diseases, such as SARS-CoV-2, is the inability to quickly identify individuals with neutralizing antibodies in the population. The corresponding inability to identify neutralizing antibodies in samples from previously vaccinated or infected individuals for the development of further treatments, such as highly effective convalescent plasma or recombinant antibodies that target the infectious disease, and diagnostics that also rely on identification of specific neutralizing antibodies.

Accordingly, the present disclosure relates to the detection of neutralizing antibodies in a sample from a patient. In particular, the present disclosure provides compositions, methods, devices, and kits for detecting neutralizing antibodies. More specifically, the disclosure relates to detecting neutralizing antibodies for SARS-CoV-2.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

"Antibodies" is meant in a broad sense and includes immunoglobulin molecules belonging to any class, IgA, IgD, IgE, IgG and IgM, or sub-class IgA1, IgA2, IgG1, IgG2, IgG3 and IgG4 and including either kappa and lambda light chain.

"Epitope" refers to a portion of an antigen to which an antibody specifically binds. Epitopes usually consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Specifically binds," "specific binding" or "binds" refers to antibody binding to an antigen or an epitope within the antigen with greater affinity than for other antigens or epitopes. Typically, the antibody binds to the antigen or the epitope within the antigen with an equilibrium dissociation constant ($K_D$) of $1 \times 10^{-7}$ M or less, for example $1 \times 10^{-8}$ M or less, $1 \times 10^{-9}$ M or less, $1 \times 10^{-10}$ M or less, $1 \times 10^{-11}$ M or less, or $1 \times 10^{-12}$ M or less, typically with a $K_D$ that is at least one hundred-fold less than its $K_D$ for binding to a non-specific antigen (e.g., BSA, casein). The $K_D$ may be measured using standard procedures. Antibodies that specifically bind to the antigen or the epitope within the antigen may, however, have cross-reactivity to other related antigens, for example to the same antigen or a counterpart antigen from other species or virus, such as the S protein on multiple coronaviruses.

As used herein, a "neutralizing antibody" is any antibody that can prevent, inhibit, reduce, impede, or interfere with, the ability of an infectious agent to initiate and/or perpetuate an infection in a host. One way in which neutralizing antibodies may prevent infection is to interfere with the processes that lead to infection of the host. Where the infectious agent is a virus, such interference may occur when binding of the antibody to the virus interferes with the physical or conformational processes relating to infection, such as physically preventing a viral protein from binding to the cell or preventing conformational changes in a viral protein that are required for infection.

As used herein, a "viral binding neutralizing antibody" is a neutralizing antibody that can prevent, inhibit, reduce, impede or interfere with the ability of viral receptor-binding protein to bind its cellular target receptor. In most instances, the cellular target receptor is another protein and, in particular, is commonly the ectodomain of a cell membrane-associated protein found in a target cell in the host. In some embodiments, a viral binding neutralizing antibody recognizes the viral receptor-binding protein as its antigen. In more specific embodiments, the viral binding neutralizing antibody specifically binds an epitope located in a portion of the viral receptor-binding protein that is necessary for binding of the viral receptor-binding protein to the cellular target receptor protein.

A "patient" in the present disclosure is any organism capable of forming antibodies and of being infected by the infectious agent. Typically, the patient is an animal, more specifically a mammal. In particular embodiments, the patient may be a human. In other particular embodiment, the patient may be an animal that is capable of being infected by SARS-CoV-2, including a human, a non-human primate (more particularly a Rhesus macaque, a cynomolgus macaque, a baboon, a grivet, a marmoset, or a gorilla, a chimpanzee, or an orangutan), a cat (particularly a domesticated cat or another feline species such as a lion, tiger, leopard, cheetah, panther, bobcat, or other wild cat), a dog, a wolf, a bat (particularly a fruit bat), a fox, a coyote, a pangolin, a ferret, an otter, a mink, a deer (particularly a white-tailed deer), a vole (particularly a bank vole), a hamster, a pig, a rabbit, a raccoon, a squirrel, or a tree shrew. A patient need be infected with or have been exposed to or vaccinated for the infectious agent. Any individual organism that provides a sample may be considered a patient within the context of this disclosure.

A "sample" according to the present disclosure may include any biological material from the patient that may contain antibodies produced by that patient. In specific embodiments, the sample may be blood (particularly capillary or venous blood), plasma, serum, or interstitial fluid. In other specific embodiments in which is it helpful to detect the presence of neutralizing antibodies in a specific biological material, the sample may be that specific biological material, such as sputum, nasal secretions, ear secretions, saliva, fluid resulting from bronchoalveolar lavage, breast milk, pus, vaginal secretions, vomit, urine, or feces.

It will be appreciated that the sample type and the location from which the sample is obtained will vary depending on the infectious agent to be detected and whether the presence of neutralizing antibodies is to be detected in a specific biological material.

A sample may be treated or prepared in any manner sufficient to maintain antibodies within the sample. For example, it may be placed in an aqueous solution having a particular pH, treated, for example by centrifugation or lysis buffer, to remove whole cells, refrigerated, frozen, or subject to separation techniques.

In specific embodiments geared towards point-of-care or at-home detection of neutralizing antibodies, the sample may be collected though a non-surgical or minimally invasive medical procedure, such as venipuncture or finger stick to obtain blood, plasma, or serum, or skin stick, such as using a lancet adapted for obtaining blood sugar monitoring samples, to obtain interstitial fluid, or a nasal or throat swab.

Some samples, such as urine, feces, or breast milk, may be collected from biological materials naturally expelled from the body.

Exemplary infectious agents for which neutralizing antibodies may be detected using embodiments of the present disclosure include respiratory viruses such as coronavirus, including, SARS-CoV-2, influenza, and RSV, as well as gastrointestinal viruses. Other exemplary infectious agents include respiratory, gastrointestinal, and skin bacteria or fungi, such as tuberculosis, *S. aureus*, such as MRSA, and yeast. Specific exemplary infectious agents include, Human coronavirus, 229E; Human coronavirus, OC43; Human coronavirus, NL63; MERS-coronavirus; SARS-CoV-2; Adenovirus 21; Human Metapneumovirus (hMPV); Parainfluenza virus 1; Parainfluenza virus 2; Parainfluenza virus 3; Parainfluenza virus 4a; Influenza A; Influenza B; Enterovirus D68; Respiratory syncytial virus; Rhinovirus 40; *Haemophilus* influenza; *Streptococcus pneumonia; Streptococcus pyogenes; Candida albicans; Bordetella pertussis; Mycoplasma* pneumonia; *Chlamydia* pneumonia; *Legionella pneumophila*; and *Staphylococcus aureus*.

Infectious agents are known to mutate over time and nAbs for variants of the above and other infectious agents may also be detected using the assays of this disclosure. For example, nAbs for variants of SAR-CoV-2, particularly those of concern, such as the delta variant and later-arising variants, may be detected. If any variants contain a mutation in the spike protein, then an assay as disclosed herein may use the mutated spike protein associated with that variant to confirm that nAbs are able to neutralize the particular variant.

Following infection or vaccination, some individuals may not produce neutralizing antibodies and these individuals may remain at higher risk for being carriers as well as susceptible to a second wave of infection. In some instances it may be useful to know if someone previously infected by or vaccinated for an infectious agent produces neutralizing antibodies in certain locations or biological tissues, such as in breast milk, where the antibodies may benefit a nursing child. In still other instances, it may be useful to obtain information about neutralizing antibodies to evaluate the quality of convalescent plasma or to identify antibodies for development as therapeutic or diagnostic agents.

Existing antibody-binding assays measure total antibodies, i.e., all antibodies in the sample that bind the antigen, rather than measuring only neutralizing antibodies. Neutralizing antibodies can be detected using viral neutralization assays, such as the plaque reduction neutralization assay (PRNT), but such assays are not suitable for large scale deployment and some has associated disease risks for laboratory personnel.

An assay, such as embodiments of those provided herein, that can mimic the standard viral neutralization assays and be available for safe use in a reference laboratory, point-of-care, or even a home or in-the-field setting, is an extremely important addition to the existing tool kit for managing COVID-19. The present disclosure provides assay embodiments that detect and quantify specific neutralizing antibodies in sera or plasma in a reliable, easily interpretable, and rapidly deployable manner.

Embodiments of assays as provided herein can be used on presumptive patients, symptomatic patients, and vaccinated patients, as well as for surveillance of vulnerable groups to preempt outbreaks and identify at-risk individuals for isolation. Presumptive patients include individuals who have been exposed to an individual who has tested positive for SARS-CoV-2 infection or exhibits symptoms of SARS-CoV-2 infection; individuals who exhibit symptoms consistent with SARS-CoV-2 infection; and individuals who have been tested because of symptoms consistent with SARS-CoV-2 infection or possible exposure to SARS-CoV-2 and who are awaiting test results. Symptomatic patients exhibit one or more symptoms of SARS-CoV-2 infection. Vaccinated patients, who may include presumptive patients and symptomatic patients, are patients who have received at least one dose of a SARS-CoV-2 vaccine. In all patients, the assays provided herein may be used to assess immune response for therapeutic or prognostic decision making. For example, patients with high levels of neutralizing antibodies may be considered likely to recover sooner and have a lower chance of severe complications. Clinical care can be triaged based on these types of assessments. For surveillance of vulnerable groups, those with low levels or undetectable levels of neutralizing antibodies may be identified as high risk individuals and targeted for mitigation measures such as pre-emptive quarantine, vaccination, administration of a vaccine booster, or administration of an anti-viral drug. Vulnerable groups include the elderly, residents of nursing homes, health care workers, people working in industries that involve crowded indoor conditions such as warehouse workers, packing industry workers, airlines crews, etc., individuals with preexisting conditions such as diabetes, heart disease, etc, and individuals in location with high incidence of SARS-CoV-2 infection. The U.S. Centers for Disease Control (CDC) provide periodic updates on vulnerability factors and high-risk activities, as do other similar governmental bodies in other jurisdictions.

The provided assay is also useful in vaccine and vaccine booster trials, for example to determine whether recipients develop neutralizing antibodies, as well as in identifying priority vaccination or vaccine booster groups in the wider population, for example, those individuals with low or undetectable levels of neutralizing antibodies.

Advantages of embodiments of assays provided herein as compared to the currently available methods for detecting SARS-CoV-2 include use of the full-length, trimeric native SARS-CoV-2 Spike protein ectodomain instead of the RBD or S1 fragment of Spike, which enables the capture of neutralizing antibodies that are targeted to non-conventional RBD epitopes in Spike protein (see e.g. Barnes C O, West A P, Huey-Tubman K E, Hoffmann M A G, Sharaf N G, Hoffman P R, et al. "Structures of Human Antibodies Bound to SARS-CoV-2 Spike Reveal Common Epitopes and Recurrent Features of Antibodies." Cell 2020 Jun. 24 and Barnes C O, West A P, Huey-Tubman K E, Hoffmann M A G, Sharaf N G, Hoffman P R, et al. "Structures of Human Antibodies Bound to SARS-CoV-2 Spike Reveal Common Epitopes and Recurrent Features of Antibodies." Cell 2020 Jun. 24), as well as providing results that are more similar to live-virus or pseudovirus-based neutralization assays. In particular, embodiments of assay provided herein may specifically detect antibodies that prevent Spike binding to ACE2.

The present disclosure provides a method as illustrated in FIG. 1 using a full length viral receptor-binding protein ectodomain, or a truncated protein that encompasses at least 80%, at least 90%, at least 95%, or at least 99% of the full length protein ectodomain, with a deletion at one or both ends as compared to the full length viral receptor-binding protein ectodomain, or a protein at least 80%, 85%, 90%, 95%, 96%, 97%, 98%, or 99% identical to the full length ectodomain or truncated protein (each of which may be referred to as a "viral receptor-binding protein"), coupled at one end to a label, such as by a covalent bond between the viral receptor-binding protein to form a viral receptor-binding protein-label complex.

The viral receptor-binding protein-label complex may comprise or consist of the viral receptor-binding protein and the label. In embodiments with a non-protein label, the viral receptor-binding protein-label complex may comprise or consist of the viral receptor-binding protein, the label, and a moiety that conjugates the label to the protein component. In other embodiments, the viral receptor-binding protein complex may comprise or consist of the viral receptor-binding protein, a second protein covalently attached to the viral receptor-binding protein and/or a moiety that conjugates the label to the protein component. The second protein may simply be part of a contiguous fusion protein also containing the viral receptor-binding protein.

The label may be located anywhere on the viral receptor-binding protein such that the label does not substantially interfere with binding of the viral receptor-binding protein to it target protein. Non-protein labels, such as gold particles, particularly gold nanoparticles, may be randomly absorbed onto the viral receptor-binding protein. Larger labels, such as protein labels, may be attached at sites internal to the viral receptor-binding protein and not interfere with target protein binding capability. This is particularly true if protein labels are small, such as 20 amino acids or 10 amino acids or less in length. More commonly, the protein label may be attached to the N-terminus, the C-terminus, or both of the viral receptor-binding protein. In even more specific embodiments, the protein label may be attached only at the terminus most remote from a target protein binding domain in the viral receptor-binding protein. For example, if the viral receptor-binding protein is SARS-CoV-2 Spike protein, then protein label may be attached only at the C-terminus, which is farther from the RBD than the N-terminus.

In a specific embodiment, the label may also not substantially interfere with binding of at least one neutralizing antibody to the viral receptor-binding protein. More specifically, the label may not substantially interfere with specific binding of at least 90%, at least 98%, or at least 99% of neutralizing antibody types in a typical sample of the same type from the same organism containing neutralizing antibodies that are identified using a PRNT assay designed to detect neutralizing antibodies for the same viral receptor-binding protein. By using an antibody against the label, which is located away from binding portions of the viral receptor-binding protein and in such a way so as to not interfere with viral receptor-binding protein-target protein binding, the chances of interfering with nAb binding to the viral receptor-binding protein are mitigated. It is contemplated that there may be other locations on the viral receptor-binding protein to insert a label.

In some embodiments, such as those illustrated in FIG. 1 the label is a protein label recognized as an epitope by a detection antibody. In some embodiments, the protein label is between 5 and 500, 5 and 400, 5 and 300, 5 and 200, 5 and 100, between 5 and 50, between 5 and 25, between 5 and 20, between 5 and 15, or between 5 and 10 amino acids long. In specific embodiments, the protein label may comprise or consist of Strep-tag II, Strep-tag, FLAG (FLAG-1, FLAG-2, or FLAG-3), 6×His, HA, c-myc (also referred to in the art as simply myc), Avitag, GST, MBP, S-tag, CBP, TAP, V5, CBD, or any combinations thereof. In specific embodiments, the protein label may comprise or consist of a protein having any one or any combinations of the amino acids provided in SEQ ID Nos: 6-18 (Table 1). In a more specific embodiment, the protein label may comprise or consist of a strep tag, such as a strep tag having the amino acid sequence provided in SEQ. ID. NO: 6.

In other embodiments, the ELISA does not use a protein tag. Instead, the ELISA contains a viral receptor-binding protein complex with a non-protein tag, such as any non-protein tag described herein, particularly those also suitable for use in a lateral flow assay. In specific embodiments, the non-protein tag is a gold particle, particularly a gold nanoparticle. An ELISA using a non-protein tag may be conducted by combining a viral receptor-binding protein, such as a SARS-CoV-2 Spike protein, with a non-protein label (e.g. a viral receptor-binding protein-label complex) with a sample from a patient and including antibodies to form a mixture; exposing the mixture to a target protein, such as human ACE2 protein ectodomain, bound to substrate, incubating the mixture with the target protein for a length of time sufficient to allow the viral receptor-binding protein to bind the target protein (if not prevented from doing so by a nAb), washing the substrate, and measuring the amount of the non-protein label associated with the substrate as compared to a negative control. A reduced amount of non-protein label associated with the substrate as compared to a negative control indicate the presence of antibodies that are neutralizing for viral receptor-binding protein binding to target protein. Measurements may be conducted using light, for example, by measuring absorption at an OD specific for the non-protein label.

Figure 2A:
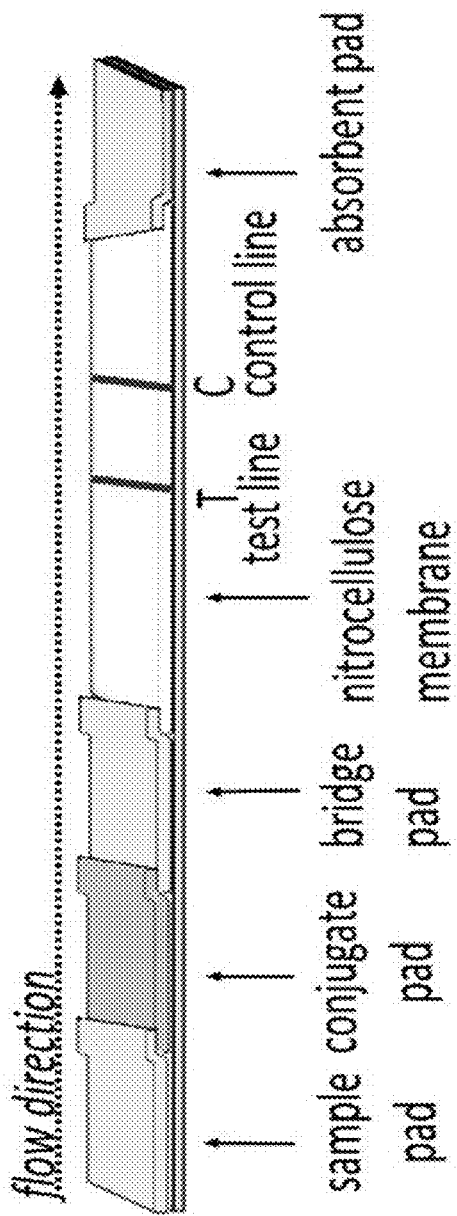
FIG. 2A and FIG. 2B depict an exemplary embodiment of a lateral flow neutralizing antibody detection assay, as provided herein.
Figure 2B:
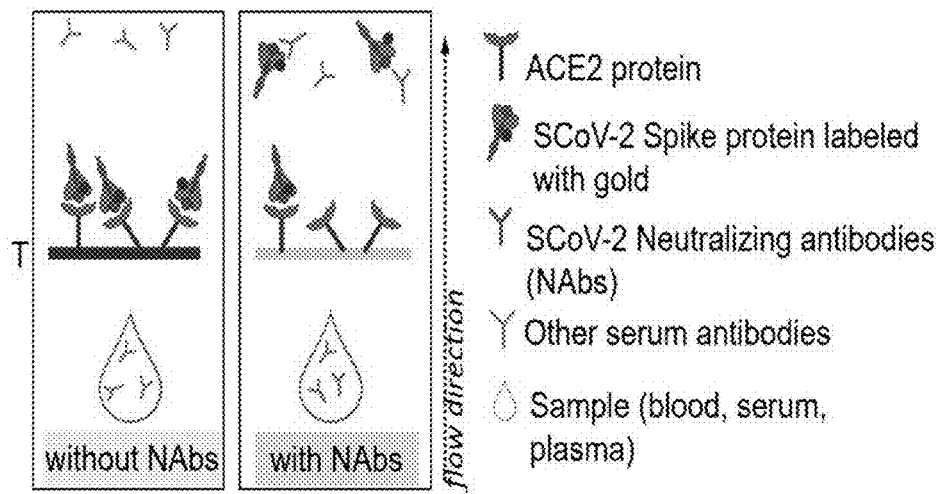

In other embodiments, such as those illustrated in FIG. 2A and FIG. 2B, the label is a non-protein label, particularly a gold particle, such as a gold nanoparticle. The non-protein label may be conjugated to the viral receptor-binding protein using a colloidal or liquid gold system. In specific embodiments, the label is randomly absorbed onto the viral receptor-binding protein using any suitable technique.

The viral receptor-binding protein-label complex may be assembled such that the viral receptor-binding protein has the conformation it would also exhibit on the viral envelope. This may be accomplished by including domains in the native protein responsible for a particular conformation, or by including a replacement domain that confers a similar conformation. For example, in an assay to detect nAbs for SARS-CoV-2, the Spike protein ectodomain may lack its native trimerization domain, but, it may be covalently attached at the C-terminus on an exogenous trimerization domain, such as a T4 fibritin trimerization domain, to ensure assembly into the natural trimeric Spike protein conformation.

In some embodiments, the viral receptor-binding protein-label complex may comprise or a protein component that comprises or consists of a full-length SARS-CoV-2 Spike protein ectodomain, or at least 80%, at least 90%, at least 95%, or at least 99% of the full-length SARS-CoV-2 Spike protein ectodomain, with a deletion at one or both ends as compared to the full length viral receptor-binding protein ectodomain, or a protein at least 80%, 85%, 90%, 95%, 96%, 97%, 98%, or 99% identical to the full length ectodomain or truncated protein. The SARS-CoV-2 Spike protein may comprise or consist of the amino acid sequence provided in SEQ ID NO: 1, or a protein at least 80%, 85%, 90%, 95%, 96%, 97%, 98%, or 99% identical to the full length ectodomain or truncated protein as disclosed herein.

In some embodiments, the SARS-CoV-2 Spike protein may be coupled to a protein tag as disclosed herein, particularly a strep tag. For example, the viral receptor-binding protein-label complex may comprise or consist of the amino acid sequence provided in SEQ ID NO:4, or a protein at least 80%, 85%, 90%, 95%, 96%, 97%, 98%, or 99% identical to the full length ectodomain or truncated protein as disclosed herein. The SARS-CoV-2 Spike protein may be coupled to the protein tag in a fusion protein that includes both proteins.

Assays of the present disclosure may further include a target protein that comprises or consists of the cellular target receptor protein, or at least a component thereof that is bound by the viral receptor-binding protein, such as all or part of an ectodomain of the cellular target receptor protein. The target protein may be coupled to a moiety that facilitates it being affixed to a substrate, such as a plate or an assay pad. When the target protein is affixed to substrate, the portion to which the viral receptor-binding protein binds may be exposed for binding.

In some embodiments in which the assay detects nAbs for SARS-CoV-2, the cellular target receptor protein may comprise or consist of ACE2, an ectodomain of ACE2, or a combination of ACE2 or an ectodomain of ACE2 with a moiety that facilitates the protein being affixed to a substrate. In some embodiments, the ACE2 protein may comprise or consist of an amino acid sequence having at least 80%, 85%, 90%, 95%, 96%, 97%, 98%, 99%, or 100% identity to the sequence provided in SEQ ID NO:3.

In some embodiments, the ACE2 protein is an ACE2-Fc fusion protein comprising an ectodomain fragment of ACE2. In some embodiments, the ACE2 protein comprises or consists of the amino acid sequence provided in SEQ ID NO:5. In some embodiments, the ACE2 protein comprises an amino acid sequence having at least 80%, 85%, 90%, 95%, 96%, 97%, 98%, 99%, or 100% identity to the sequence provided in SEQ ID NO:5.

Referring now to FIG. 1, which uses SARS-CoV-2 as a specific example, but is applicable to other infectious agents, the present disclosure provides an ELISA for detection of nAbs that can bind the infectious agent, in this example SARS-CoV-2 as depicted in the left panel. In an initial step, shown in the upper portion of the right panel, a target protein, in this example the human ACE2 ectodomain, is bound to an assay plate, for example in the well of a multi-well assay plate. A viral-receptor binding-protein, in this example full-length SARS-CoV-2 Spike protein ectodomain, is labeled with a protein label, in this example strep tag II. A sample from a patient is prepared for use in the assay. In this example, the sample is serum or plasma and is simply diluted with an appropriate buffer. As shown in the upper portion of the right panel, the sample is combined with the viral receptor-binding protein label complex, here Spike-strep tag II, and placed in a well with bound ACE2. If neutralizing antibody is not present, then Spike remains free to bind to ACE2, as depicted in the "binding" half of the diagram. If neutralizing antibody is present, then it prevents Spike from binding ACE2, as depicted in the "inhibiting" half of the diagram. The sample may be combined with the viral receptor-binding protein-label complex prior to or simultaneously with addition of the viral receptor-binding protein-label complex to the well with bound target protein. In the example depicted in FIG. 1, the sample and viral receptor-binding protein-label complex are combined prior to addition to the well with bound protein target.

A protein label monoclonal antibody that specifically binds the protein label, which is Strep tag II in this example, is added to the assay sample. The protein label monoclonal antibody may be added prior to, simultaneously with, or after incubation of the viral receptor-binding protein-label complex with the sample in the well with bound target protein. In the example depicted in FIG. 1, the protein label monoclonal antibody is added prior to incubation in the well.

Due to the placement of the label at the end of the viral receptor-binding protein, the presence of protein label monoclonal antibody typically does not interfere with binding to the target protein. For example, placement of the label at the end of a SARS-CoV-2 Spike protein ectodomain motif avoids interference with ACE2 binding. Accordingly, as simplified procedure, as depicted in FIG. 1, may be used in which the sample, the viral receptor-binding protein-label complex, and the protein label monoclonal antibody may simply all be combined together and incubated for a period of time sufficient to allow nAb-viral receptor-binding protein binding and protein label monoclonal antibody—viral receptor-binding protein-label complex binding, then added to the well with bound target protein.

After incubation of the viral receptor-binding protein-label complex and sample in the well for a sufficient time to allow binding of the viral receptor-binding protein to the target protein, if nAbs are not present, the well may be washed to remove unbound proteins. However, washing at this step is not required.

Next, as shown in the middle portion of the right panel, a detection monoclonal antibody is added. The detection polyclonal antibody specifically binds the constant region of the protein label monoclonal antibody. For example, the protein label monoclonal antibody may have a constant region of the IgG1 isotype, as depicted. In that case, the detection polyclonal antibody specifically binds constant regions with an IgG1 isotype.

As shown in the "binding" half of the figure, if a nAb in the sample did not interfere with viral receptor-binding protein-target protein binding, here Spike strep tag II-ACE2 binding, then the viral receptor-binding protein-label complex binds the target protein in the well and thereby becomes tethered in the well. The protein label monoclonal antibody binds the label and also becomes tethered in the well. Finally, the detection polyclonal antibody binds the protein label monoclonal antibody and becomes tethered in the well.

As shown in the "inhibition" half of the figure, if a nAb in the sample did interfere with viral receptor-binding protein binding to the target protein, nothing other than the target protein is tethered in the well.

The detection polyclonal antibody also contains a detection label, which may be any detection label used in the art. For example, as depicted in FIG. 1, the detection label may be a fluorophore, a chromophore, or an enzyme that catalyzes a reaction that produces a fluorescent or color reaction product when the enzyme is exposed to an enzymatic substrate. In a specific example, the detection label may be horseradish peroxidase.

After incubation with the detection polyclonal antibody, the well is washed to remove unbound proteins, in particular unbound detection polyclonal antibody. Then the detection polyclonal antibody is detected directly if the detection label facilitates direct detection, or a detection reagent that become detectable after interaction with the detection polyclonal antibody, such as a substrate for horseradish peroxidase that becomes fluorescent after cleavage by the enzyme, is added.

Finally, as shown in the lower portion of the right panel, the detection polyclonal antibody is detected in each well of the assay plate, for example by detecting color or fluorescence at a specific wavelength. As shown in the "binding" column, if no nAbs are present in the sample, a substantial amount of detection polyclonal antibody is detected, for example through detection of a high level of fluorescence. As shown in the "inhibition" column, if highly protective nAbs or a highly protective amount of nAbs are present in the sample, no detection polyclonal antibody is detected, for example, through detection of no or only a background level of fluorescence.

In practice, the amount of detection polyclonal antibody detected will likely lie somewhere between an amount that corresponds to no interference with viral receptor-binding protein-target protein binding (e.g. a sample with no antibodies, or only antibodies known not bind to the viral receptor-binding protein), and an amount that corresponds to complete or nearly complete neutralization of the viral receptor-binding protein (e.g. a sample with a large amount of an antibody known, for example through live virus or pseudovirus assays, to be strongly neutralizing). A calibration curve for a given assay type, a given assay lot, and/or a given detector may be developed and used to quantify the amount or potency of nAbs in the sample or to generate semi-quantitative results, such as absent, low, medium, and high, either of which, in turn be used for diagnostic or other medical purposes.

The use of an isotype-specific, here anti-IgG1, detection polyclonal antibody to detect the protein label antibody, here the anti-strep-tag antibody, enhances the detection signal, as it reduces the signal from non-specific interactions with other IgG molecules present in the blood or serum sample.

Further, at least certain ELISA assays of the present disclosure can accommodate the use of specimens diluted to a higher degree than other assays on the market. Currently available SARS-CoV-2 detection assays use from 1:1 to 1:10 fold diluted specimens, while the presently disclosed ELISA methods can use specimens diluted 1:40 fold or more. The increased dilution may allow conservation of valuable specimens, better discrimination of nAb titers between individuals, and/or minimized background that can arise from non-specific antibody binding commonly encountered with concentrated specimens. Thus, embodiments of the disclosed methods may provide a simple, safe, and/or less labor-intensive assay that can replace viral neutralization assays performed in specialized laboratories using live virus or pseudovirus without sacrificing reliability or fidelity of the results.

In an exemplary embodiment, which may be as described below or as combined with any other aspects of an ELISA disclosed herein, particularly in Examples 1-5, an enzyme-linked immunosorbent assay (ELISA) intended for the qualitative direct detection of total neutralizing antibodies to SARS-CoV-2 in human serum and plasma is provided. The human serum and plasma may additionally contain dipotassium EDTA, lithium heparin, sodium citrate, and any combinations thereof. The ELISA may be used in identifying individuals with an adaptive immune response to SARS-CoV-2, indicating recent or prior infection. The ELISA may be conducted in a laboratory, such as a laboratory authorized by a regulatory authority to perform high complexity tests.

More specifically the ELISA may detect neutralizing antibodies to SARS-CoV-2 that prevent binding of the SARS-CoV-2 Spike (S) protein to the human angiotensin converting enzyme 2 (ACE2) receptor. The protein-protein interaction may be designed to mimic the virus-host interaction. More specifically, the SARS-CoV-2 protein may comprise or consist of the amino acid sequence provided in SEQ ID NO:4. The ACE2 receptor may comprise or consist of the amino acid sequence provided in SEQ ID NO:5.

Diluted serum or plasma samples (obtained from specimens) may be first incubated with recombinant SARS-CoV-2 S protein and a monoclonal antibody, which may be a protein label monoclonal antibody. More specifically, the monoclonal antibody may be an IgG1 monoclonal antibody that specifically binds strep tag II. Then the mixture may be transferred to ACE2 receptor protein-coated wells. After incubation and washing, the monoclonal antibody-SARS-CoV-2 S protein immune complex remain bound to ACE2 on the plate surface unless the interaction was inhibited by neutralizing antibodies in the specimen. Secondary antibody conjugated to horseradish peroxidase targeting the monoclonal antibody may then be added to each well. More specifically, the secondary polyclonal antibody may be a goat polyclonal antibody that specifically binds IgG1 and that is tagged with horseradish peroxidase (HRP).

After incubation, the ELISA wells may be washed before a tetramethylbenzidine substrate may be added. An acidic solution, such as 1N Sulfuric acid, may finally be used to stop the reaction and the degree of enzymatic turnover of the substrate may be determined by measuring optical density (OD) at 450 nanometers.

A negative control and, optionally, also a positive control may be tested using the same assay, more specifically during the same assay run as the test sample.

The OD values may be used to calculate the signal inhibition according to the following equation:

$$\text{Signal Inhibition (\%)} = (1 - [\text{Sample OD} \div \text{Negative Control OD}]) \times 100\%$$

If Signal Inhibition is greater than 25%, the result is positive, which means that neutralizing antibodies for SARS-CoV-2 have been detected in the sample.

If Signal Inhibition is between 15% and 25%, the result is inconclusive and a retest is recommended. During a retest, the sample may be tested in duplicate. If the retest Signal Inhibition is greater than or equal to 20%, then neutralizing antibodies for SARS-CoV-2 have been detected in the sample. If the retest Signal Intensity is less than 20%, the neutralizing antibodies for SARS-CoV-2 have not been detected in the sample.

If Signal Inhibition is less than 15%, the results is negative, which means that neutralizing antibodies for SARS-CoV-2 have not been detected in the sample.

The assay may be conducted using a kit, which may include coated microtiter strips, negative control, positive control, neutralization mix, neutralization dilution buffer, conjugate, conjugate diluent, wash buffer, liquid TMB substrate and stop solution. Control materials may include a SCoV-2 NAB Positive Control, which may be provided in one vial, 150 μL. The Positive Control contains SARS-CoV-2 neutralizing antibodies and will aid in monitoring the integrity of the kit. Control materials may also include a SCoV-2 NAb Negative Control, which may be provided in one vial, 150 μL. The Negative Control will aid in monitoring the integrity of the kit and in interpreting sample results.

The present disclosure additionally provides a lateral flow assay as depicted in FIG. 2A, which may be carried out using a lateral flow assay cassette as depicted. Specifically the lateral flow assay cassette may contain an internal structure as depicted in FIG. 2B, having a nitrocellulose membrane on which rests, at a sample end, in the direction of sample flow when a liquid sample is applied, a sample pad, a conjugate pad, and a bridge pad. An absorbent pad rests on the absorbent end of the nitrocellulose membrane, where sample flow halts. In between the bridge pad and the absorbent pad, there are at least two assay lines, a test line and a control line, on the nitrocellulose membrane. In some embodiments, multiple test lines, for example with varying concentrations of target protein, and/or multiple control lines may be present.

Figure 3:
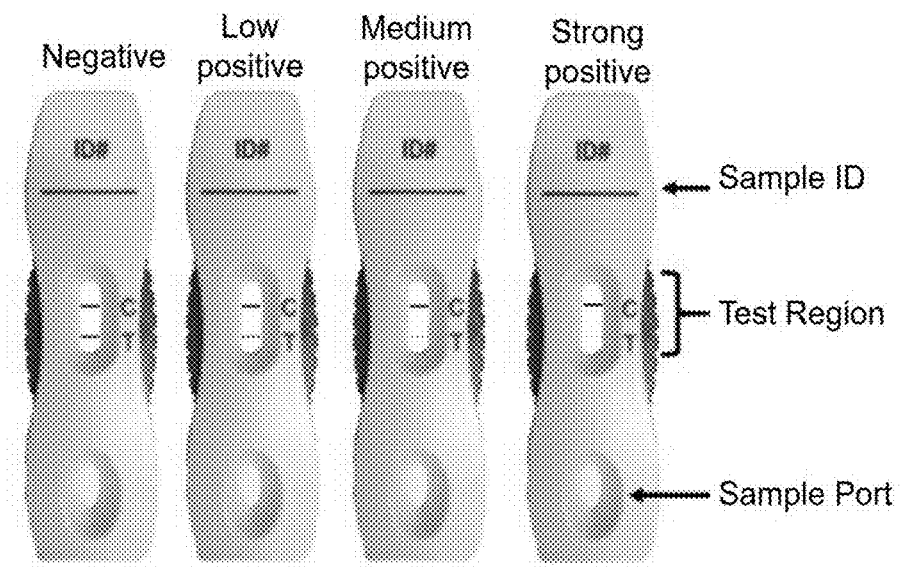
FIG. 3 depicts lateral flow assay cassettes used in a lateral flow neutralizing antibody detection assay of FIG. 2A and FIG. 2B. The cassettes illustrate negative, low positive, medium positive, and strong positive results.

The lateral flow assay cassette may have an external housing as depicted in FIG. 3, which may include a sample port, located above the sample pad, and a test region, in which the test line and control line are visible. The lateral flow assay cassette may further include indicators, such as C and T, that designate the test and control lines. The lateral flow assay cassette may further include a sample designator, which, as depicted may be a simple line on which an ID code may be written. The sample designator may also be a bar code, QR code, or other digitally readable code, which may be associated with the sample and/or the patient who contributed the sample.

In a first step, a liquid sample is placed on the sample pad, for example using the sample port of a lateral flow assay cassette. It then flows over the conjugate pad. The conjugate pad contains viral receptor-binding protein-label complex, which, in the example shown in FIG. 2A and FIG. 2B, is a SARS-CoV-2 spike protein labeled with colloidal gold. The conjugate pad also contains colloidal gold-labeled control antibodies that specifically bind a control target protein. Proteins may be labelled with colloidal gold using any conventional techniques. Other forms of gold labeling or labeling with other color or fluorescent elements or compounds may be used. Typically, the same type of label will be used for the viral receptor-binding protein label complex and the control antibody and may also be attached to both proteins using the same technique.

The sample flows from the sample pad into and through the conjugate pad. In the conjugate pad, any nAbs in the sample bind to the viral receptor-binding protein-label conjugate. The sample continues to flow into the bridge pad and finally onto the test line and control line, carrying viral receptor-binding protein-label complex and any attached nAbs as well as control antibodies with it.

If there are no nAbs in the sample, then the viral receptor-binding protein label complex binds to the target protein in the test line. In the example shown in FIG. 2A, left panel, the gold-labeled Spike protein binds to ACE2 in the test line. The bound viral receptor-binding protein label complex does not continue to flow with the liquid portion of the sample to the absorbent pad. Gold in the viral receptor-binding protein label complex becomes concentrated on the test line and is visible or detectable.

If there are highly protective nAbs or a highly protective amount of nAbs in the sample, then viral receptor-binding protein label complex binding to the target protein is blocked. In the example shown in FIG. 2A, right panel, the gold-labeled Spike protein does not bind to ACE2 in the test line and instead continues to flow with the liquid portion of the sample into the absorbent pad. Gold does not become concentrated on the test line and the test line remains invisible or very faint.

Regardless of what antibodies are in the sample, the control antibody that was picked up by the sample in the conjugate pad specifically binds to the control target in the control line and does not continue to flow with the liquid portion of the sample to the absorbent pad. The gold becomes concentrated on the control line and become visible or detectable, allowing verification that the assay functioned as intended.

In some embodiments, a chase buffer may be used to facilitate movement of the sample over the test and control lines and into the absorbent pad.

In practice, the amount of gold visible or detectable on the test line will likely lie somewhere between an amount that corresponds to no interference with viral receptor-binding protein-target protein binding (e.g. a sample with no antibodies, or only antibodies known not bind to the viral receptor-binding protein), and an amount that corresponds to complete or nearly complete neutralization of the viral receptor-binding protein (e.g. a sample with a large amount of an antibody known, for example through live virus or pseudovirus assays, to be strongly neutralizing).

For example, FIG. 3 shows four potential assay results in which a visible control line demonstrates assay function, and the darkness of the test line varies. In some embodiments, a user may simply rely on the presence or absence of a visible test line to determine whether any neutralizing antibodies are present. In other embodiments, such as that depicted in FIG. 3, the user may compare the test line to a key that shows different darknesses of test lines that correlate with semi-quantitative results, such as the sample being low positive, medium positive, or strong positive for nAbs.

In other embodiments, the test lines may be read by a reader that quantifies the darkness of the test line and, optionally, also the control line. The reader may provide a quantitative or semi-quantitative result reflecting the amount of potency of nAbs in the sample. The reader may use a calibration curve for a given assay type, a given assay lot, and or/a given reader. The calibration curve may also rely in part on the darkness of the control line.

In some embodiments, the test line and control line may be ready by a reader (e.g., smartphone app) to quantify the test and control line signal strength (e.g., peak or integrated values). The ratio of the test and control lines may then be calculated to provide a consistent metric which accounts for varying light sources, angles of operation, camera characteristics, etc.

In some embodiments, the reader may be a phone app or other program easily implemented by a point-of-care, home, or in-the-field user.

In some embodiments, the ratios and thresholds for test positivity may be lot dependent and can be remotely determined and set (e.g., on a remote server) where the reader may pull updated information regarding any specific test lot.

In some embodiments, an artificial intelligence-based reader may be used. In the context of such a reader, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, or devices. Accordingly, the various embodiments may be entirely hardware embodiments, entirely software embodiments, or embodiments combining software and hardware aspects.

Figure 4:
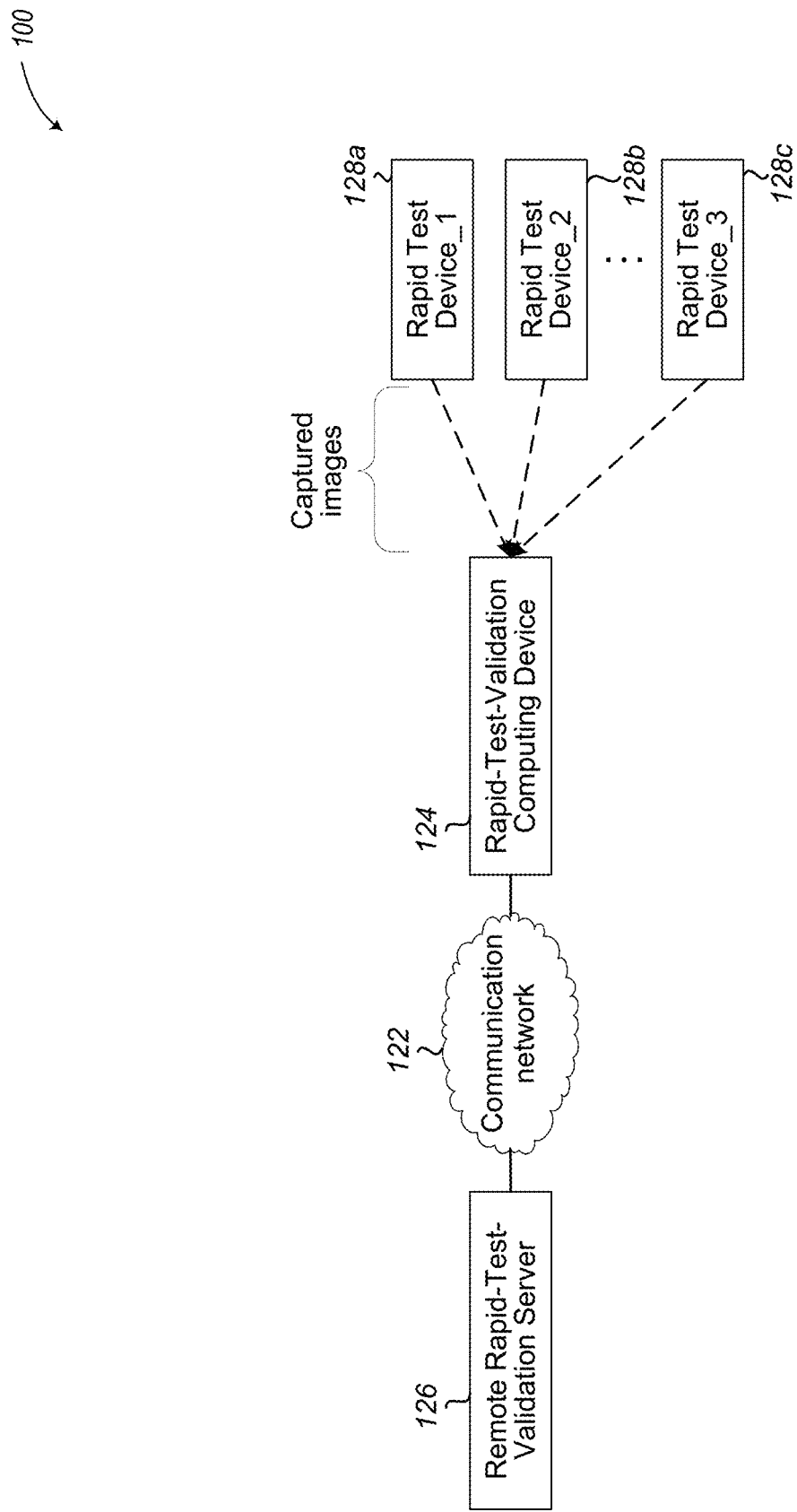
FIG. 4 illustrates a context diagram of an environment for validating lateral flow assay cassette results.

FIG. 4 illustrates a context diagram of an environment 100 for validating lateral flow assay results in accordance with embodiments described herein. Environment 100 includes a lateral flow assay validation computing device 124 and one or more lateral flow assay cassettes 128a-128c (individually and collectively referred to as lateral flow assay cassette 128).

The lateral flow assay cassettes 28a-128c perform a lateral flow assay for nAbs as described herein.

The reader 124 captures one or more images of the lateral flow assay cassette 128 via a camera (not illustrated). The reader 124 utilizes a first artificial intelligence mechanism to determine if a position of the lateral flow assay cassette 128 in the captured images is acceptable for processing, such as if it is in a particular position or within a threshold variance of a reference position. For example, the reader may use an auto-leveler function to ensure the lateral flow assay cassette is within a tolerable variance of being parallel to the camera. In some embodiments, the reader 124 may also augment the captured images by overlaying a semi-transparent reference or representation of the lateral flow assay cassette 128 to enable the user to properly align the reader 124 with the lateral flow assay cassette 128. In some embodiments, a plurality of images are captured and displayed to the user in real time to allow the user to move the position of the lateral flow assay cassette 128 or the reader 124 for proper alignment.

Although embodiments are described herein as using an artificial intelligence mechanism to determine a position of the rapid test device (or a color validation sheet), embodiments are not so limited. Rather, other techniques for tracking objects in images may be used, such as edge or shadow detection.

In some embodiments, the reader 124 may utilize the previously captured image that included the properly aligned lateral flow assay cassette 128 for further processing. In other embodiments, the reader 124 may capture another image in response to manual user input or automatically, such as when the lateral flow assay cassette 128 is properly aligned.

If the lateral flow assay cassette 128 is positioned properly in at least one of the captured images, the reader 124 utilizes a second artificial intelligence mechanism on the image to determine if a result of the lateral flow assay cassette 128 is valid or invalid. For example, if the control line is not present or is too faint, the result may be determined to be invalid and the user instructed to repeat the assay with a different lateral flow assay cassette and possibly also a different sample.

If the result is valid, the reader 124 may utilize a third artificial intelligence mechanism on the image to determine an objective characterization of the results (e.g., "positive," "negative," a semi-quantitative indicator, or a quantified amount, etc.). The objective characterization may be determined as described above using the darkness of the test line and, in some instances, also the control line. In one embodiment, the third may use the second image to determine the intensity of the control line by analytical methods that may include integrating grayscale images around the control line and determining the peak value present in the control line, determine the intensity of the test line by analytical methods including integrating grayscale images around the test line and determining the peak value present in the test line, determine the ratio of the test line peak value or the integrated test line value to the control line peak value or integrated control line value, and then use the determined ratio to present the presence or absence of and/or a semi-quantitative or quantitative amount of neutralizing antibody in the sample result to the user.

The reader 124 displays the objective characterization of the results to a user of the reader 124. The reader 124 also displays information indicating if the result of the lateral flow assay cassette 128 is valid or invalid.

In some embodiments, the reader 124 may omit the use of the second artificial intelligence mechanism and may not present information indicating if the result of the lateral flow assay cassette 128 is valid or invalid. In such embodiments, the user may be instructed to determine if a control line is visible and to disregard assay results if it is not. Alternatively, in such embodiments, the third artificial intelligence may be unable or present results, particularly if, as described above, the determining the results requires the presence of a control line to calculate a ratio.

In some embodiments, the reader 124 determines and displays the objective characterization of the results and the valid/invalid determination in real time as the user is using the reader 124 to capture images of the lateral flow assay cassette 128. In other embodiments, the reader 124 may capture images of one or more lateral flow assay cassettes 128 for post-processing and display to a user. In various embodiments, the reader 124 may transmit or upload the validation and objective results, along with the captured images, to one or more other computing devices for storage or review. The results may be associated with a sample identifier, for example a sample ID input by the user or scanned by the reader from the lateral flow assay cassette.

Results can be used to further train or refine the artificial intelligence mechanisms used herein. Examples of such other computing devices may include remote server 126, cloud computing resources, or other remote computing devices that maintain patient data. In some embodiments, an identifier or lot number of the lateral flow assay cassette may be stored with the results, which can be used to determine if a particular lateral flow assay cassette lot or batch is defective, e.g., due to erroneous results.

In some embodiments, a user may use the reader 124 to select a lateral flow assay cassette for processing. The user may select the appropriate lateral flow assay cassette from a list of possible lateral flow assay cassettes or the user may scan a machine readable symbol (e.g., barcode, QR code, etc.) or other identifier of the lateral flow assay cassette. In at least one embodiment, the reader 124 may be configured to start or utilize a timer for the selected lateral flow assay cassette. For example, if the lateral flow assay cassette requires 20 minutes to complete the assay and output a result, then the reader 124 may utilize a timer so as to not process the lateral flow assay cassette until after the timer has expired. In this way, the reader 124 does not process a lateral flow assay cassette and output a result before the lateral flow assay cassette has completed its assay. Likewise, the same timer or a second timer may establish a window of time in which to process the lateral flow assay cassette. This time window may be used to ensure the lateral flow assay cassette is not process too late.

Examples of the reader 124 include, but are not limited to, smartphones, tablet computers, desktop or laptop computers in communication with a camera, wearable computers, or other computing devices that have or are in communication with a camera.

In some embodiments, the environment 100 may optionally include a server 126. In various embodiments, the remote server 126 may perform many of the embodiments described herein as being performed by the reader 124. In at least one embodiment, the reader 124 may capture images of the lateral flow assay cassettes 128 and transmit the captured images to the remote server 126 via communication network 122 for processing. The communication network 122 includes one or more wired or wireless, or a combination of wired and wireless, data communication networks. The remote server 126 may output the results to a user via a display device (not illustrated) or may transmit the results back to the reader 124 for display.

Figure 5:
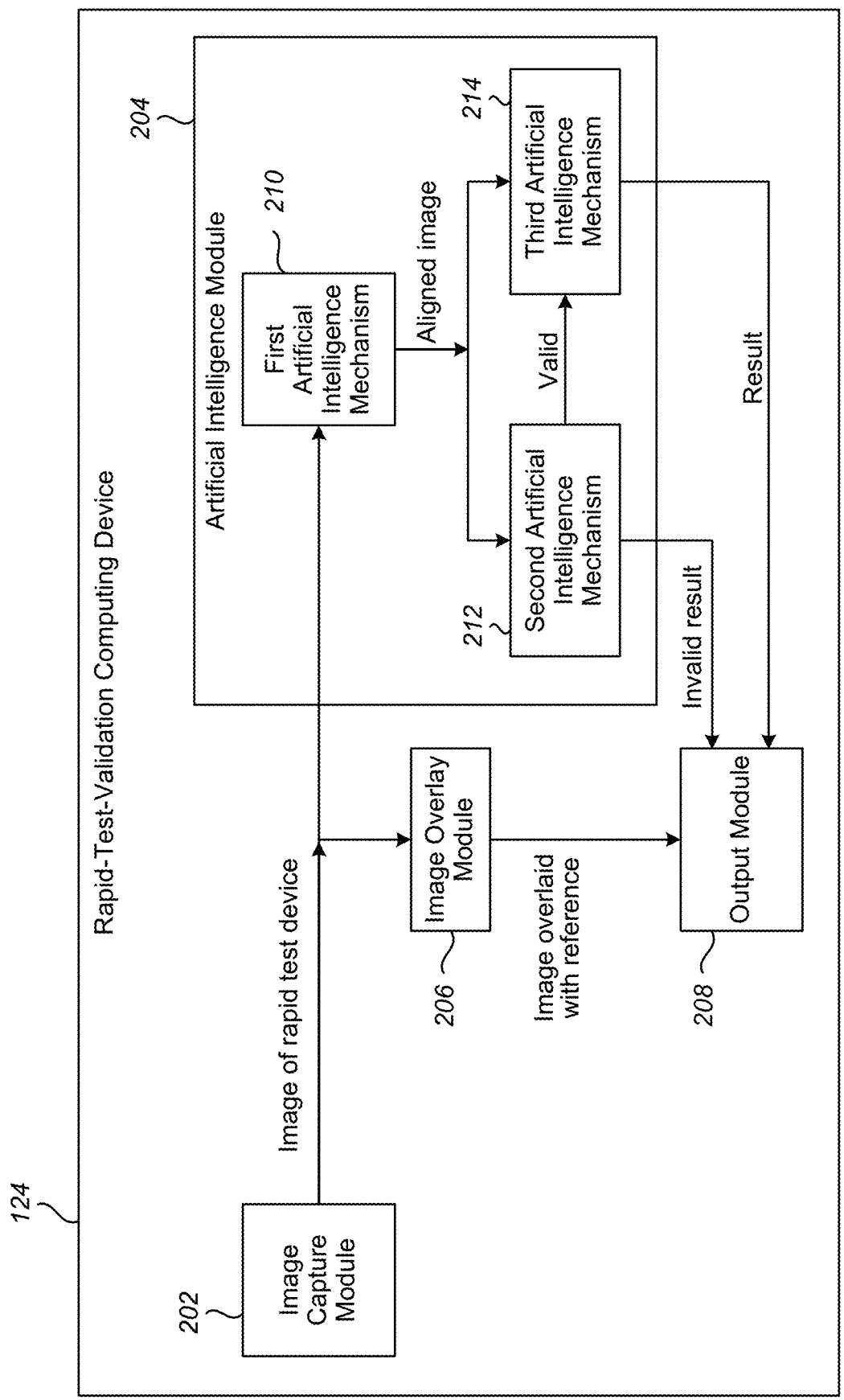
FIG. 5 illustrates a system diagram of a reader.

FIG. 5 illustrates a system diagram of a reader 124 in accordance with embodiments described herein. The system components of the reader 124 illustrated in FIG. 5 are for illustrative purposes and are not to be limiting. Moreover, the functionality of one or more of the illustrated system components may be combined into fewer components or separated in more components than what is shown.

In this illustrated example, the reader 124 includes an image capture module 202, an artificial intelligence module 204, an image overlay module 206, and an output module 208. The image capture module 202 performs embodiments described herein to capture or obtain images of one or more rapid test devices. The captured images are provided from the image capture module 202 to the artificial intelligence module 204 and to the image overlay module 206. The image overlay module 206 modifies or augments the captured images to overlay a semi-transparent reference or representation of the rapid test device. The modified images are provided from the image overlay module 206 to the output module 208 for presentation to a user.

The artificial intelligence module 204 includes a first artificial intelligence mechanism 210, a second artificial intelligence mechanism 212, and a third artificial intelligence mechanism 214. The first artificial intelligence mechanism 210 determines if the rapid test device is properly aligned in the captured image. The second artificial intelligence mechanism 212 determines if one or more results on the rapid test device are valid or invalid. If the results are invalid, the artificial intelligence module 204 presents the invalid determination to a user via the output module 208. The third artificial intelligence mechanism 214 determines an objective characterization of the valid results. The artificial intelligence module 204 presents the object characterization of the results to the user via the output module 208. In some embodiments, the artificial intelligence module 204 may instruct the image capture module 202 to capture additional images of the rapid test device, such as if the rapid test device is not properly positioned in the captured images.

In some embodiments, the output module 208 displays information to a user of the reader 124 via a display device. In other embodiments, the output module 208 transmits the results information to another computing device, such as remote server 126, for display, storage, or further processing (e.g., comparing a plurality of results from a plurality rapid test device).

The operation of certain aspects will now be described with respect to FIG. 6. In at least one of various embodiments, process 300 described in conjunction with Figure may be implemented by one or more processors or executed via circuitry on one or more computing devices, such as reader 124 of FIG. 4A or remote server 126 of FIG. 4.

Figure 6:
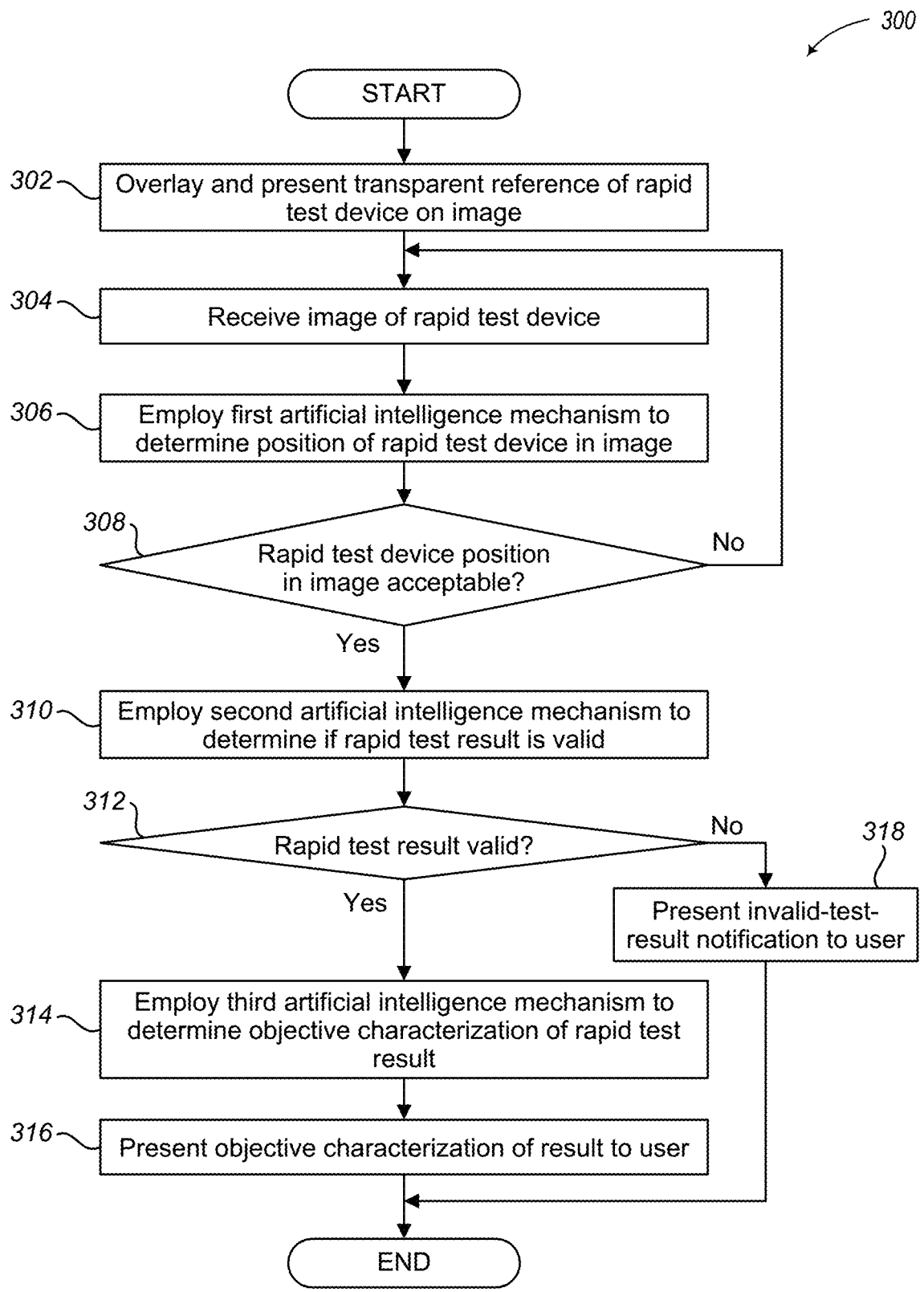
FIG. 6 illustrates a logical flow diagram showing one embodiment of a process for capturing images of a lateral flow assay cassette and employing artificial intelligence mechanisms to validate results.

FIG. 6 illustrates a logical flow diagram showing one embodiment of a process 300 for capturing images of a lateral flow assay cassette 128 and employing artificial intelligence mechanisms to validate results in accordance with embodiments described herein.

Process 300 begins, after a start block, at block 302, where a transparent reference of a lateral flow assay cassette is presented to a user as being overlaid on images captured by the reader. In some embodiments, the overlaid image is displayed to the user via a graphical user interface. In other embodiments, the overlaid image is transmitted or sent to another computing device for display to the user.

The transparent reference is a partially transparent representation of the lateral flow assay cassette being validated and may be referred to as the lateral flow assay cassette reference. The transparent reference provides a visual cue to a user as to an ideal position for the lateral flow assay cassette to be within the images for proper processing and analysis.

In some embodiments, the particular type of lateral flow assay cassette reference is selected by a user. In at least one embodiment, a list of possible lateral flow assay cassette references is presented to the user. The user can then select the lateral flow assay cassette that matches or corresponds to the rapid test device being validated. In other embodiments, an artificial intelligence mechanism is employed on the received image to select the lateral flow assay cassette reference. In yet other embodiments, the artificial intelligence mechanism may be employed to determine a set of possible lateral flow assay cassette references, which is then presented to the user. The user is then prompted to select the particular lateral flow assay cassette reference of the rapid test device being validated. In some other embodiments, a machine readable symbol (e.g., barcode or QR code) or other identifying information on the lateral flow assay cassette, or the packaging of the lateral flow assay cassette, may be scanned to identify or select the lateral flow assay cassette.

In embodiments where the image includes a plurality of lateral flow assay cassette, a plurality of lateral flow assay cassette references may be overlaid on the received image. In some embodiments, the positioning of the plurality of lateral flow assay cassette references in the overlaid image may be determined based on the positioning of lateral flow assay cassettes being validated within the received image, such as by employing a plurality of machine learning models trained to identify different lateral flow assay cassettes and their locations within an image.

Process 300 proceeds to block 304, where an image of a lateral flow assay cassette is received. In some embodiments, the image is captured by the device executing process 300, e.g., reader 124. In other embodiments, the image is captured by a device remote from the device executing process 300, e.g., remote server 126. In some embodiments, the image may include a plurality of lateral flow assay cassettes.

Process 300 continues at block 306, where a first artificial intelligence mechanism is employed to determine a position of the lateral flow assay cassette in the received image. In some embodiments, the first artificial intelligence mechanism is a machine learning model trained to identify the lateral flow assay cassette in an image. In other embodiments, the first artificial intelligence mechanism stores one or more characteristics of lateral flow assay cassettes in which to compare with the received image.

Process 300 proceeds next to decision block 308, where a determination is made whether the position of the lateral flow assay cassette in the received image is acceptable. In some embodiment, the positioning of the lateral flow assay cassette in the image is acceptable when the first artificial intelligence mechanism identifies the lateral flow assay cassette in the image. In other embodiments, the position of the lateral flow assay cassette in the image is acceptable when the first artificial intelligence mechanism indicates that the lateral flow assay cassette is positioned within a selected threshold size, rotation, and tilt of the lateral flow assay cassette reference. If the position of the lateral flow assay cassette in the image is acceptable, process 300 flows to block 310; otherwise, process 300 loops to block 302 to continue to receive additional images of the lateral flow assay cassette.

In some embodiments when process 300 loops to block 302, an instruction may be presented to the user indicating advice on how to better position the lateral flow assay cassette within the image. The looping of process 300 may enable a plurality of images to be captured as a video to be displayed to the user in real time so that the user can move the physical lateral flow assay cassette (or camera) in a way to align the physical lateral flow assay cassette with the lateral flow assay cassette reference overlaid on the video. Once aligned, one or more images can be captured to be further analyzed by process 300. These images can be captured in response to manual input from the user, or they may be automatically captured when the system determines that the position of the lateral flow assay cassette relative to the camera is acceptable.

At block 310, a second artificial intelligence mechanism is employed to determine if the lateral flow assay cassette result is valid. In some embodiments, the second artificial intelligence mechanism is a machine learning model trained to classify valid or invalid results output by the lateral flow assay cassette. In other embodiments, the second artificial intelligence mechanism stores one or more characteristics of valid and invalid lateral flow assay cassette results in which to compare with the received image.

Figures 7A, 7B:
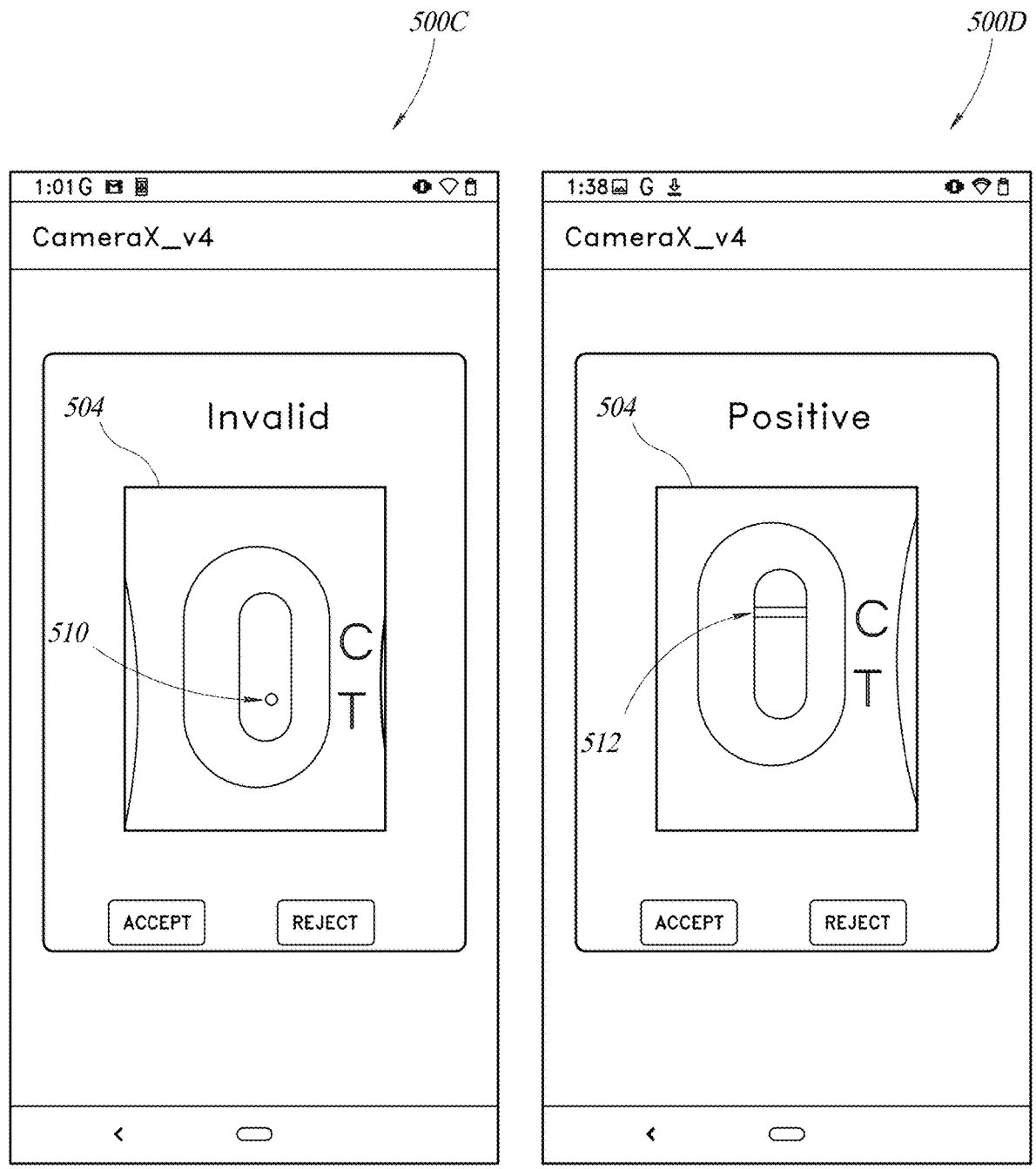
FIG. 7A and FIG. 7B illustrate use case examples of graphical user interfaces presenting information to a user with respect to validating lateral flow assay cassette results.

For example, a valid result may be a full-length control line as shown in FIG. 3 and FIG. 7A. In comparison, an invalid test result may be a dot in the area near the test and control line, e.g. as shown in FIG. 7B. In other embodiments, valid or invalid test results may be identifiable by color, intensity, etc.

In various embodiments, a plurality of second artificial intelligence mechanisms are generated for corresponding lateral flow assay cassettes of a plurality of different lateral flow assay cassettes. A particular second artificial intelligence mechanism is selected from the plurality of artificial intelligence mechanisms based on the lateral flow assay cassette selected or identified at block 304. This selected second artificial intelligence mechanism is then utilized with respect to the corresponding lateral flow assay cassette in the received image.

In some embodiments, a single lateral flow assay cassette may have multiple output areas with different results. In at least one such embodiment, different second artificial intelligence mechanisms are generated for each corresponding output area of the lateral flow assay cassette and employed on the received image to determine if results in each separate output area are valid or invalid.

Process 300 continues next at decision block 312, where a determination is made whether the lateral flow assay cassette results are valid based on the employment of the second artificial intelligence mechanism. If the test results are valid, process 300 flows to block 314; otherwise, process 300 flows to block 318 to present an invalid-test-result notification to the user via a graphical user interface. In some embodiments, the invalid-test-result notification may indicate the result "invalid," similar to what is shown in FIG. 7B. In other embodiments, the invalid-test-result notification may provide additional information indicating whether the sample was too small or tainted, or if the lateral flow assay cassette malfunctioned.

At block 314, a third artificial intelligence mechanism is employed to determine an objective characterization of the lateral flow assay cassette result. In some embodiments, the third artificial intelligence mechanism is a machine learning model trained to classify possible test results output by the lateral flow assay cassette. In other embodiments, the third artificial intelligence mechanism stores one or more characteristics of each possible test result of the lateral flow assay cassette in which to compare with the received image.

For example, a negative nAb test result may be a full-length control line and a full-length test line as illustrated in FIG. 3. A positive nAb test result may be a full-length control line and no test line, as illustrated in FIG. 3. In other embodiments, different objective results may be identifiable by color, intensity, alphanumeric codes, etc.

As described herein in the context of the lateral flow assay, semi-quantitative results, such as negative, weak positive, positive, and strong positive may be calculated by the third artificial intelligence mechanism using the intensity or darkness of the test line and any of various possible calibration references. A quantitative result may also be calculated by the third artificial intelligence mechanism.

In various embodiments, a plurality of third artificial intelligence mechanisms are generated for corresponding lateral flow assay cassettes of a plurality of different lateral flow assay cassettes. A particular third artificial intelligence mechanism is selected from the plurality of artificial intelligence mechanisms based on the lateral flow assay cassette selected or identified at block 304. This selected third artificial intelligence mechanism is then utilized with respect to the corresponding lateral flow assay cassette in the received image to identify the corresponding results.

As mentioned above, a single lateral flow assay cassette may have multiple output areas with different results. In at least one embodiment, different third artificial intelligence mechanisms are generated for each corresponding output area of the lateral flow assay cassette and employed on the received image to determine the objective characterization of the results in each separate output area.

Process 300 proceeds next to block 316, where the objective characterization of the assay results are presented to a user. In some embodiments, the results are displayed to the user via a graphical user interface. In other embodiments, the results are transmitted or sent to another computing device for display to the user. The displayed objective characterization may be qualitative or binary result, such as "positive" or "negative," or it may be semi-quantitative and/or quantitative. In some embodiments, a confidence level or value of the objective characterization may be determined and displayed to the user.

After block 316 or after block 318, process 300 terminates or otherwise returns to a calling process to perform other actions. In some embodiments, process 300 may loop (not illustrated) to block 302 to receive new images of lateral flow assay cassette.

Results of a lateral flow assay cassette validated using system 100 or process 300 may, in some embodiments, be generated and displayed using a smartphone app. In these embodiments, a ratio score may be generated based on signal intensity (e.g. darkness) of the test line compared to that of the control line. The ratio or another quantification based on it may be displayed to the user. Alternatively, or in addition, a cut-off ratio for the type of assay may be generated using a receiver operating characteristic curve from a panel of negative and positive samples. Ratios may be correlated with semi-quantitative values using a panel of known nAbs. A code may be supplied with each lateral flow assay cassette that provides adjustments to be made to the base cut-off ratio and semi-quantitative values, as well as possible adjustments to quantitative values to ensure uniformity across assays. The adjustments associated with the code are determined by testing of representative lateral flow assay cassettes from batches prior to shipment to users.

Figure 8:
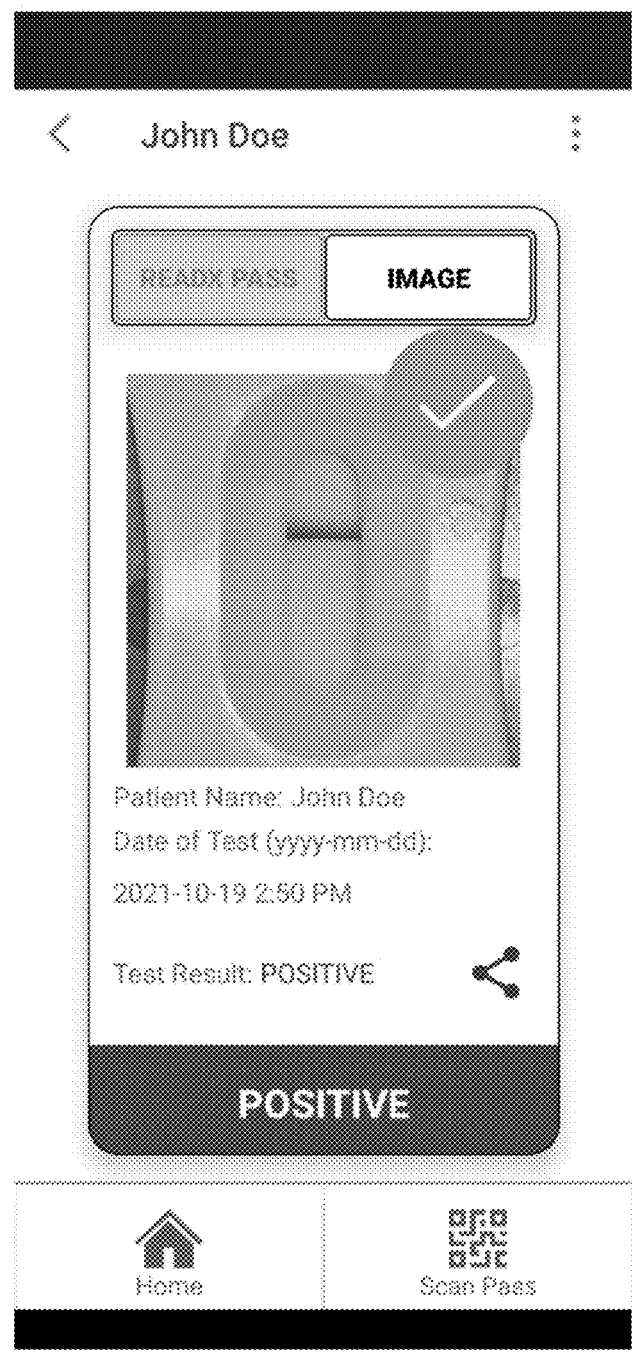
FIG. 8 illustrates an example validation result from a reader as described herein that may be transmitted from a user to another party.

Results may also be shared with others in a secure and verifiable fashion. For example, the smartphone app used to validate the results of a lateral flow assay cassette may generate a QR code or other digital code associated with the results. This code may be displayed on the smartphone and scanned by another smartphone or reader or it may be transmitted to another smartphone or reader. The QR code may be opened in the same or a compatible app on the other smartphone or reader and may display information regarding the lateral flow assay cassette validation results. For example, it may display information about the patient, date of assay, and positive/negative, semi-quantitative, or quantitative results. An example of the type of results that may be displayed by the reader is shown in FIG. 8.

Lateral flow assays of the present disclosure, particularly in conjunction with artificial intelligence-based readers as disclosed herein, may be readily usable by patients at home or by medical personnel in a point-of-care or field setting and may provide easy transmission and verification of neutralizing antibody status for SARS-CoV-2 or any of a range of infectious agents.

The present disclosure further provides a kit for detection of nAbs in a sample from a patient. The kit includes a viral receptor-binding protein-label complex and a target protein. Kits may further include sample preparation materials, such as buffers and diluents, and/or sample collection materials, such as lancets and/or swabs or capillary tubes.

For ELISA-based detection, the kit may further include an assay plate with wells to which the target protein is bound, or a reagent for binding the target protein to the wells of an assay plate. The kit may further include one or more detection antibodies, at least one of which specifically binds the label and at least one of which, which may be the same antibody, produced a detectable signal.

The ELISA-based kit may further include wash buffer, reagents for detection, instructions for use, and/or a digital or readable label identifying the assay and/or lot.

For lateral flow cassette-based detection, the kit may further include a lateral flow assay cassette as described herein that has at least a test line, a control line, and materials sufficient to cause results to be presented using the test line and control line. The lateral flow assay cassette may further include a chase buffer, instructions for use, a code or instructions of downloading a reader app, and/or a digital or readable label identifying the assay and/or lot.

TABLE 1

Sequences

| Sequence Description | SEQ ID NO. | Sequences |
|---|---|---|
| SARS-CoV-2 Spike protein; GenBank QHD43416 | 1 | MFVFLVLLPL VSSQCVNLTT RTQLPPAYTN SFTRGVYYPD KVFRSSVLHS TQDLFLPFFS NVTWFHAIHV SGTNGTKRFD NPVLPFNDGV YFASTEKSNI IRGWIFGTTL DSKTQSLLIV NNATNVVIKV CEFQFCNDPF LGVYYHKNNK SWMESEFRVY SSANNCTFEY VSQPFLMDLE GKQGNFKNLR EFVFKNIDGY FKIYSKHTPI NLVRDLPQGF SALEPLVDLP IGINITRFQT LLALHRSYLT PGDSSSGWTA GAAAYYVGYL QPRTFLLKYN ENGTITDAVD CALDPLSETK CTLKSFTVEK GIYQTSNFRV QPTESIVRFP NITNLCPFGE VFNATRFASV YAWNRKRISN CVADYSVLYN SASFSTFKCY GVSPTKLNDL CFTNVYADSF VIRGDEVRQI APGQTGKIAD YNYKLPDDFT GCVIAWNSNN LDSKVGGNYN YLYRLFRKSN LKPFERDIST EIYQAGSTPC NGVEGFNCYF PLQSYGFQPT NGVGYQPYRV VVLSFELLHA PATVCGPKKS TNLVKNKCVN FNFNGLTGTG VLTESNKKFL PFQQFGRDIA DTTDAVRDPQ TLEILDITPC SFGGVSVITP GTNTSNQVAV LYQDVNCTEV PVAIHADQLT PTWRVYSTGS NVFQTRAGCL IGAEHVNNSY ECDIPIGAGI CASYQTQTNS PRRARSVASQ SIIAYTMSLG AENSVAYSNN SIAIPTNFTI SVTTEILPVS MTKTSVDCTM YICGDSTECS NLLLQYGSFC TQLNRALTGI AVEQDKNTQE VFAQVKQIYK TPPIKDFGGF NFSQILPDPS KPSKRSFIED LLFNKVTLAD AGFIKQYGDC LGDIAARDLI CAQKFNGLTV LPPLLTDEMI AQYTSALLAG TITSGWTFGA GAALQIPFAM QMAYRFNGIG VTQNVLYENQ KLIANQFNSA IGKIQDSLSS TASALGKLQD VVNQNAQALN TLVKQLSSNF GAISSVLNDI LSRLDKVEAE VQIDRLITGR LQSLQTYVTQ QLIRAAEIRA SANLAATKMS ECVLGQSKRV DFCGKGYHLM SFPQSAPHGV VFLHVTYVPA QEKNFTTAPA ICHDGKAHFP REGVFVSNGT HWFVTQRNFY EPQIITTDNT FVSGNCDVVI GIVNNTVYDP LQPELDSFKE ELDKYFKNHT SPDVDLGDIS GINASVVNIQ KEIDRLNEVA KNLNESLIDL IAGLIAIVMV TIMLCCMTSC CSCLKGCCSC GSCCKFDEDD SEPVLKGVKL HYT |
| SARS-CoV-2 Spike protein RBD; GenBank 6MOJ_E | 2 | RVQPTESIVR FPNITNLCPF GEVFNATRFA SVYAWNRKRI SNCVADYSVL YNSASFSTFK CYGVSPTKLN DLCFTNVYAD SFVIRGDEVR QIAPGQTGKI ADYNYKLPDD FTGCVIAWNS NNLDSKVGGN YNYLYRLFRK SNLKPFERDI STEIYQAGST PCNGVEGFNC YFPLQSYGFQ PTNGVGYQPY RVVVLSFELL HAPATVCGPK KSTNLVKNKC VNFHHHEIHH |

TABLE 1-continued

Sequences

| Sequence Description | SEQ ID NO. | Sequences |
|---|---|---|
| Human ACE2 protein | 3 | MSSSSWLLLSLVAVTAAQSTIEEQAKTFLDKF NHEAEDLFYQSSLASWNYNTNITEENVQMNNA GDKWSAFLKEQSTLAQMYPLQEIQNLTVKLQL QALQQNGSSVLSEDKSKRLNTILNTMSTIYST GKVCNPDNPQECLLLEPGLNEIMANSLDYNER LWAWESWRSEVGKQLRPLYEEYVVLKNEMARA NHYEDYGDYWRGDYEVNGVDGYDYSRGQLIED VEHTFEEIKPLYEHLHAYVRAKLMNAYPSYIS PIGCLPAHLLGDMWGRFWTNLYSLTVPFGQKP NIDVTDAMVDQAWDAQRIFKEAEKFFVSVGLP NMTQGFWENSMLTDPGNVQKAVCHPTAWDLGK GDFRILMCTKVTMDDFLTAHHEMGHIQYDMAY AAQPFLLRNGANEGFHEAVGEIMSLSAATPKH LKSIGLLSPDFQEDNETEINFLLKQALTIVGT LPFTYMLEKWRWMVFKGEIPKDQWMKKWWEMK REIVGVVEPVPHDETYCDPASLFHVSNDYSFI RYYTRTLYQFQFQEALCQAAKHEGPLHKCDIS NSTEAGQKLFNMLRLGKSEPWTLALENVVGAK NMNVRPLLNYFEPLFTWLKDQNKNSFVGWSTD WSPYADQSIKVRISLKSALGDKAYEWNDNEMY LFRSSVAYAMRQYFLKVKNQMILFGEEDVRVA NLKPRISFNFFVTAPKNVSDIIPRTEVEKAIR MSRSRINDAFRLNDNSLEFLGIQPTLGPPNQP PVSIWLIVFGVVMGVIVVGIVILIFTGIRDRK KKNKARSGENPYASIDISKGENNPGFQNTDDV QTSF |
| SARS-CoV-2 Spike protein streptavidin fusion protein | 4 | MFVFLVLLPL VSSQCVNLTT RTQLPPAYTN SFTRGVYYPD KVFRSSVLHS TQDLFLPFFS NVTWFHAIHV SGTNGTKRFD NPVLPFNDGV YFASTEKSNI IRGWIFGTTL DSKTQSLLIV NNATNVVIKV CEFQFCNDPF LGVYYHKNNK SWMESEFRVY SSANNCTFEY VSQPFLMDLE GKQGNFKNLR EFVFKNIDGY FKIYSKHTPI NLVRDLPQGF SALEPLVDLP IGINITRFQT LLALHRSYLT PGDSSSGWTA GAAAYYVGYL QPRTFLLKYN ENGTITDAVD CALDPLSETK CTLKSFTVEK GIYQTSNFRV QPTESIVRFP NITNLCPFGE VFNATRFASV YAWNRKRISN CVADYSVLYN SASFSTFKCY GVSPTKLNDL CFTNVYADSF VIRGDEVRQI APGQTGKIAD YNYKLPDDFT GCVIAWNSNN LDSKVGGNYN YLYRLFRKSN LKPFERDIST EIYQAGSTPC NGVEGFNCYF PLQSYGFQPT NGVGYQPYRV VVLSFELLHA PATVCGPKKS TNLVKNKCVN FNFNGLTGTG VLTESNKKFL PFQQFGRDIA DTTDAVRDPQ TLEILDITPC SFGGVSVITP GTNTSNQVAV LYQDVNCTEV PVAIHADQLT PTWRVYSTGS NVFQTRAGCL IGAEHVNNSY ECDIPIGAGI CASYQTQTNS PSSASSVASQ SIIAYTMSLG AENSVAYSNN SIAIPTNFTI SVTTEILPVS MTKTSVDCTM YICGDSTECS NLLLQYGSFC TQLNRALTGI AVEQDKNTQE VFAQVKQIYK TPPIKDFGGF NFSQILPDPS KPSKRSFIED LLFNKVTLAD AGFIKQYGDC LGDIAARDLI CAQKFNGLTV LPPLLTDEMI AQYTSALLAG TITSGWTFGA GAALQIPFAM QMAYRFNGIG VTQNVLYENQ KLIANQFNSA IGKIQDSLSS TASALGKLQD VVNQNAQALN TLVKQLSSNF GAISSVLNDI LSRLDPPEAE VQIDRLITGR LQSLQTYVTQ QLIRAAEIRA SANLAATKMS ECVLGQSKRV DFCGKGYHLM SFPQSAPHGV VFLHVTYVPA QEKNFTTAPA ICHDGKAHFP REGVFVSNGT HWFVTQRNFY EPQIITTDNT FVSGNCDVVI GIVNNTVYDP LQPELDSFKE ELDKYFKNHT SPDVDLGDIS GINASVVNIQ KEIDRLNEVA KNLNESLIDL QELGKYEQYI KGGGGSGENL YFQGGYIPEA PRDGQAYVRK DGEWVLLSTF LGGGGSHHHH HHSSGWSHPQ FEKGGGSGGG SGGSGWSHPQ FEKGGS |

TABLE 1-continued

Sequences

| Sequence Description | SEQ ID NO. | Sequences |
|---|---|---|
| ACE2-IgG fusion protein | 5 | MSSSSWLLLSLVAVTAAQSTIEEQAKTFLDKF NHEAEDLFYQSSLASWNYNTNITEENVQNMNN AGDKWSAFLKEQSTLAQMYPLQEIQNLTVKLQ LQALQQNGSSVLSEDKSKRLNTILNTMSTIYS TGKVCNPDNPQECLLLEPGLNEIMANSLDYNE RLWAWESWRSEVGKQLRPLYEEYVVLKNEMAR ANHYEDYGDYWRGDYEVNGVDGYDYSRGQLIE DVEHTFEEIKPLYEHLHAYVRAKLMNAYPSYI SPIGCLPAHLLGDMWGRFWTNLYSLTVPFGQK PNIDVTDAMVDQAWDAWRIFKEAEKFFVSVGL PNMTQGFWENSMLTDPGNVQKAVCHPTAWDLG KGDFRILMCTKVTMDDFLTAHHEMGHIQYDMA YAAQPFLLRNGANEGFHEAVGEIMSLSAATPK HLKSIGLLSPDFQEDNETEINFLLKQALTIVG TLPFTYMLEKWRWMVFKGEIPKDQWMKKWWEM KREIVGVVEVPHDETYCDPASLFHVSNDYSFI RYYTRTLYQFQFQEALCQAAKHEGPLHKCDIS NSTEAGQLKLFNMLRLGKSEPWTLALENVVGA KNMNVRPLLNYFEPLFTWLKDQNKNSFVGWST DWSPYADEPKSCDKTHTCPPCPAPELLGGPSV FLFPPKPKDTLMISRTPEVTCVVVDVSHEDPE VKFNWYVDGVEVHNAKTKPREEQYNSTYRVVS VLTVLHQDWLNGKEYKCKVSNKALPAPIEKTI SKAKGQPREPQVYTLPPSRDELTKNQVSLTCL VKGFYPSDIAVEWESNGQPENNYKTTPPVLDS DGSFFLYSKLTVDKSRWQQGNVFSCSVMHEAL HNHYTQKSLSLSPGK |
| Strep-tag II | 6 | WSHPQFEK |
| Strep-tag | 7 | WSAPQFEK |
| FLAG-1 | 8 | DYKDDDK |
| 6 x His | 9 | HHHHHH |
| HA | 10 | YPYDVPDYA |
| c-myc | 11 | EQKLISEEDL |
| Avitag | 12 | GLNDIFEAWKIEWHE |
| GST | 13 | MSPILGYWKIKGLVQPTRLLLEYLEEKYEEHL YERDEGDKWRNKKFELGLEFPNLPYYIDGDVK LTQSMAIIRYIADKHNMLGGCPKERAEISMLE GAVLDIRYGVSRIAYSKDFETLKVDFLSKLPE MLKMFEDRLCHKTYLNGDHVTHPDFMLYDALD VVLYMDPMCLDAFPKLVCFKKRIEAIPQIDKY LKSSKYIAWPLQGWQATFGGGDHPPKSD |
| MBP | 14 | MKIEEGKLVIWINGDKGYNGLAEVGKKFEKDT GIKVTVEHPDKLEEKFPQVAATGDGPDIIFWA HDRFGGYAQSGLLAEITPDKAFQDKLYPFTWS AVRYNGKLIAYPIAVEALSLIYNKDLLPNPPK TWEEIPALDKELKAKGKSALMFNLQEPYFTWP LIAADGGYAFKYENGKYDIKDVGVDNAGAKA GLTFLVDLIKNKHMNADTDYSIAEAAFNKGET AMTINGPWAWSNIDTSKVNYGVTVLPTFKGQP SKPFVGVLSAGINAASPNKELAKEFLENYLLT DEGLEAVNKDKPLGAVALKSYEEELAKDPRIA ATMENAQKGEIMPNIPQMSAFWYAVRTAVINA ASGRQTVDEALKDAQTNSSSNNNNNNNNNLG IEGR |
| S-tag | 15 | KETAAAKFERQHMDS |
| CBP | 16 | KRRWKKNFIAVSAANRFKKISSSGAL |

TABLE 1-continued

Sequences

| Sequence Description | SEQ ID NO. | Sequences |
|---|---|---|
| TAP | 17 | GRRIPGLINPWKRRWKKNFIAVSAANRFKKIS SSGALDYDIPTTASENLYFQGEFGLAQHDEAV DNKFNKEQQNAFYEILHLPNLEEQRNAFIQSL KDDPSQSANLLAEAKKLNDAQAPKVDNKFNKE QQNAFYEILHLPNLNEEQRNAFIQSLKDDPSQ SANLLAEAKKLNDAQAPKVDANHQ |
| V5 | 18 | GKPIPNPLLGLDST |

Chitin binding domain CBD

EXAMPLES

Example 1: ELISA Assay for Detection of SARS-CoV-2 Neutralizing Antibodies

More specifically, a plate-based two-step ELISA was carried out as follows. An anti-strep IgG1 monoclonal antibody was used to detect strep-tagged recombinant S protein in Step 1, followed by detection of that complex by a mouse anti-IgG1-HRP secondary monoclonal antibody in Step 2 (FIG. 1). After two steps of detection and stringent washing, signal specific to the S protein-ACE2 complex was read in a standard ELISA plate reader after the colorimetric development of HRP (FIG. 1).

Briefly, 2 µg/mL of recombinant ACE2 was coated on ELISA plate wells at pH 7.4, overnight at 4° C. The plates were then washed thrice in 1×ELISA Wash Buffer (InBios International Inc. Seattle, USA) and blocked with InBlock (InBios International Inc. Seattle, USA). Plasma or serum samples were diluted in Sample Dilution Buffer, SDB for IgM Type B (InBios International Inc. Seattle, USA) in the presence of 150 pM recombinant S protein and 1 µg/mL of α-Strep mAb 417.69D5 (InBios International Inc. Seattle, USA). The mixture was incubated at room temperature for 30 minutes. Then 50 µL of the mixture was added to each ACE2 coated well and allowed to bind for 30 minutes at 37° C. After washing 6 times, 50 µL of anti-IgG1-HRP (Southern Biotech, USA) diluted 1:6000 in Indiluent (InBios International Inc., Seattle, USA) was added and incubated for 30 minutes at 37° C. After 6 more washes, 75 µL of 3,3',5,5'-Tetramethylbenzidine Liquid Substrate (SurModics, Eden Prairie, Minn., USA) was added for color development for 10 minutes at room temperature after which 50 µL of 1N Sulfuric acid Stop solution was added to stop the reaction. The optical density was then read at 450 nm in the VersaMax ELISA Plate Reader (Molecular Devices, San Jose, Calif.).

The assay may be carried out using a self-contained kit with a coated plate and all other reagents required for the assay along with a detailed product insert. SARS-CoV-2 Spike protein and mAb 417.69D5 are provided as a ready to use 100× mixture. The 100× Spike protein and mAb 417.69D5 is stable when stored at −20° C. All other kit components can be stored at 4° C. Formulating the 100× Spike protein and mAb 417.69D5 mixture with agents such as glycerol and BSA may allow this component to also be stored at 4° C.

Figure 9:
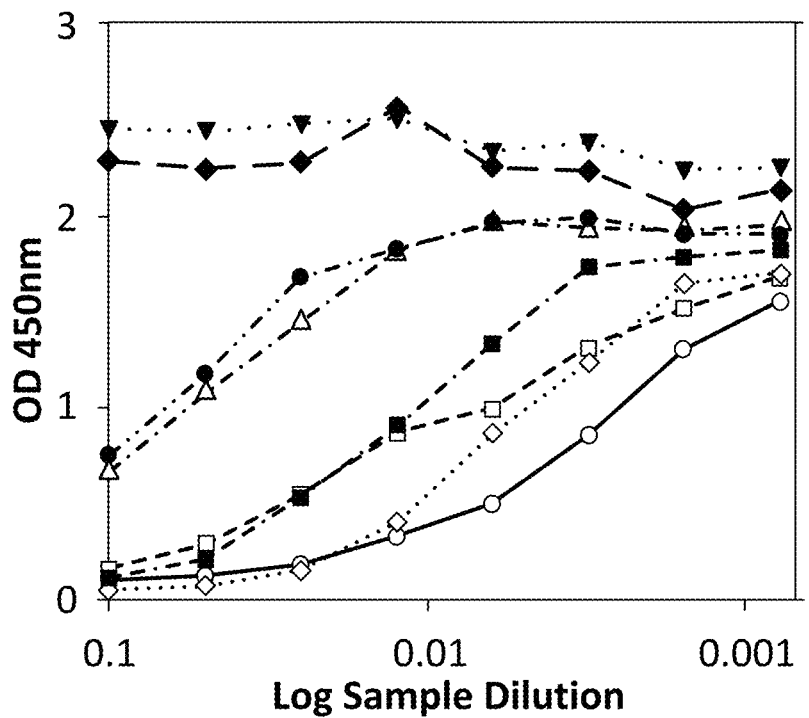
FIG. 9 depicts data obtained from an assay of the present disclosure, comparing serially diluted serum samples from patients previously diagnosed with COVID-19 with negative control normal human serum samples (NHS). The top panel shows an increase in OD 450 nm for serially diluted COVID-19 sera but not for NHS, which is indicative of decreasing inhibition of S protein-ACE2 binding by the sera with dilution. The bottom panel shows the sera-dilution-dependent percent inhibition of S-ACE2 binding by COVID-19 sera for the ELISA results shown in the top panel.
Figure 9:
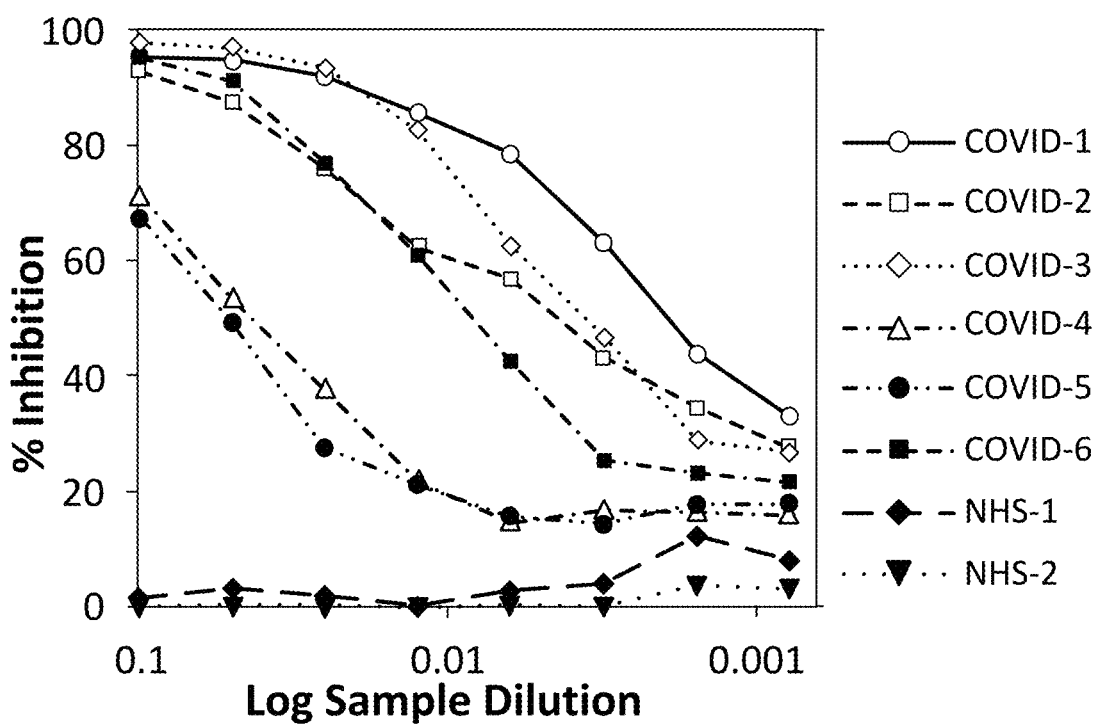
Figure 10:
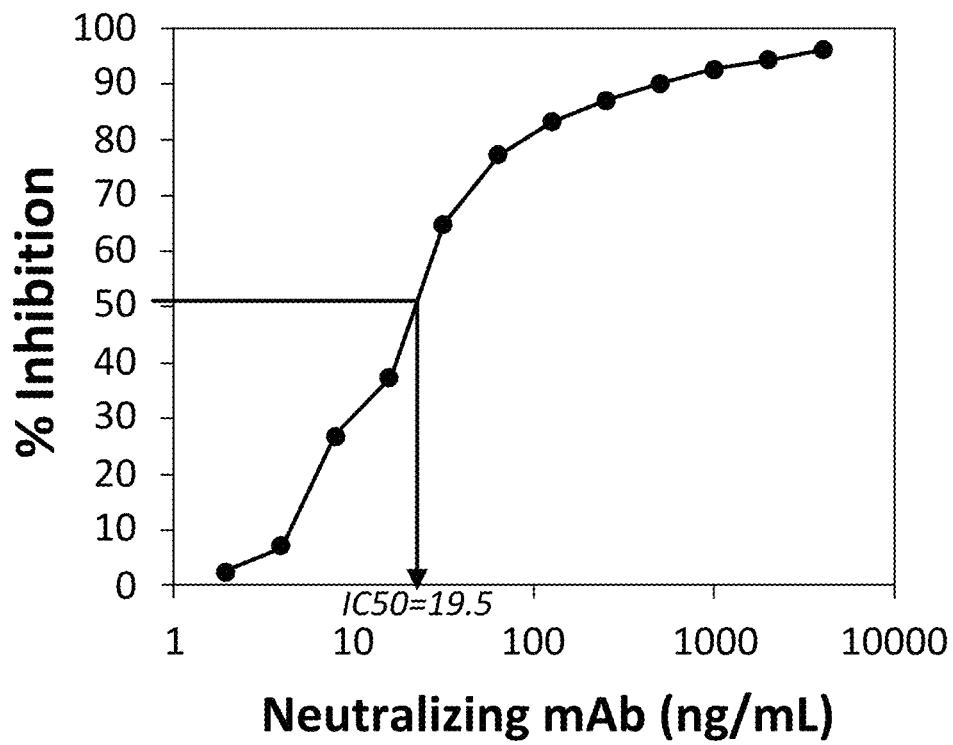
FIG. 10 depicts validation data for the assay shown in FIG. 1. The top panel shows concentration-dependent percent inhibition of S protein-ACE2 binding in the assay of FIG. 1 by a known neutralizing monoclonal antibody with an IC50 of 19.5 ng/mL, which is similar to the inhibition observed with COVID-19 sera in FIG. 9. The bottom panel shows data from measurement of the total binding IgG and IgM in the COVID-19 sera, which is consistent with expectations in convalescent sera.
Figure 10:
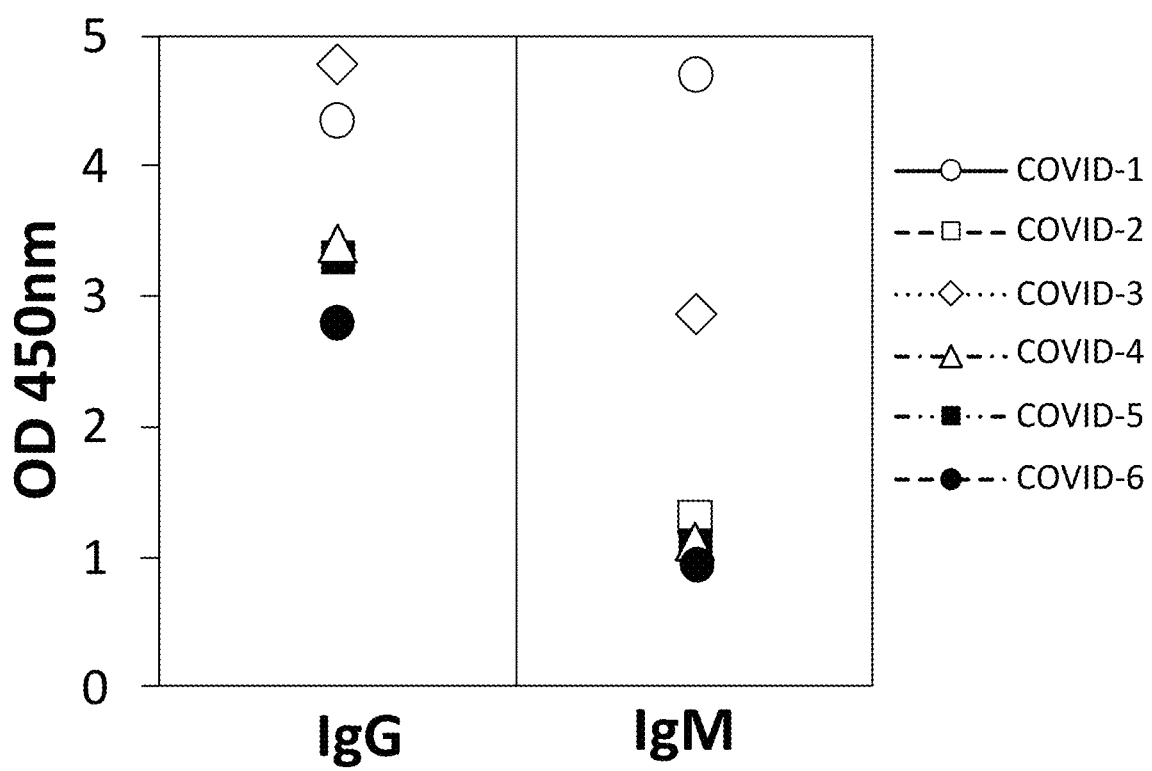

When tested on a panel of 6 COVID-19 sera, confirmed by RT-PCR, serially diluted sera displayed increase in OD 450 nm consistent with inhibition of S protein binding to the coated ACE2 receptor on the plate (FIG. 9, top panel). In comparison, the OD 450 nm measured for the NHS samples remained high and unchanged, indicative of no binding inhibition. In terms of % inhibition, high inhibition ranging from 70-98% was observed for the COVID-19 sera at a dilution of 1:10 with a gradual decrease in % inhibition as sera were diluted more, decreasing to 20-30% inhibition at final dilution of 1:1280 (FIG. 9, bottom panel). Thus, a serum dilution dependent inhibition of S protein binding to ACE2 was observed for the COVID-19 sera, distinct from the NHS. The inhibition of S protein-ACE2 binding by COVID-19 sera was comparable to that observed with a known neutralizing monoclonal antibody (InBios International Inc.), specifically raised to inhibit the interaction (FIG. 10, top panel). Thus, it is likely that the binding inhibition observed with the COVID-19 sera is due to the presence of neutralizing antibodies that interfere with S protein-ACE2 interaction.

The COVID-19 sera were also tested by FDA-EUA ELISAs for total binding antibodies and were confirmed as harboring high levels of SCoV-2 S protein-reactive IgG and IgM (FIG. 10, bottom panel). In addition, presence of total binding antibodies to equimolar amounts of S protein and RBD were also verified by indirect ELISAs, as shown in Table 2. Except for COVID-6, which harbored low levels of both IgM and IgG to S protein, all other sera were seen to harbor high levels of S protein and RBD specific total IgM and IgG.

TABLE 2

| Sample | Spike IgM | Spike IgG | RBD IgM | RBD IgG |
|---|---|---|---|---|
| COVID-1 | High | High | High | High |
| COVID-2 | High | High | High | High |
| COVID-3 | High | High | High | High |
| COVID-4 | High | High | High | High |
| COVID-5 | High | High | High | High |
| COVID-6 | Low | Low | High | High |

Example 2: Assay for Inhibition of S and RBD Binding by COVID-19 Sera

The RBD of the SARS-CoV-2 S protein has been identified as the domain that interacts with ACE2 and brings about the conformational changes that facilitate viral entry into host cells. This function also makes the RBD highly antigenic, harboring many epitopes identified as potential neutralizing antibody binding sites. Investigators have developed surrogate serological and pseudovirus-based neutralization assays using SARS-CoV-2 RBD alone for estimating the neutralization abilities of COVID-19 sera/plasma samples. In assays that compared the inhibition of S protein-ACE2 binding with RBD-ACE2 binding, similar IC50 was observed for both proteins with COVID-19 sera, indicating that S protein-ACE2 interactions are the same as RBD-ACE2 interactions (Table 3).

The neutralizing Abs in the COVID-19 sera are specific for the receptor binding domains of S protein, as established by structural and functional analysis of viral binding and entry into host cells. Emerging evidence shows that there are epitopes in S, outside of the RBD, that could be important for facilitating S protein-ACE2 interactions and viral entry. While using the RBD as an antigen in the two-step ELISA is an available option, use of full length S ectodomain as the antigen in the two-step ELISA offers sensitive and broad capture of neutralizing Abs. The sensitivity of the two-step ELISA is demonstrated by the results shown across a wide serial dilution range and the calculated IC50s obtained as well as by good correlation of positive results between this assay and confirmatory assays using alternate methods. The breadth of capture results from use of full length S protein ectodomain, which provides greater signal magnitude as compared to RBD, as well as more frequent signal saturation. Full length S protein ectodomain offers the most relevant means to recapitulate viral interaction with ACE2 and likely yields the most comprehensive surrogate serological assay to live or pseudovirus mediated neutralization assays.

TABLE 3

| Sample | $Log_{10}$ IC50 Spike | $Log_{10}$ IC50 RBD |
|---|---|---|
| COVID-1 | 2.4 | 2.5 |
| COVID-2 | 1.5 | 1.6 |
| COVID-6 | 1.6 | 1.5 |

Example 3: Cross-Reactivity of ELISA Assay

Figure 11:
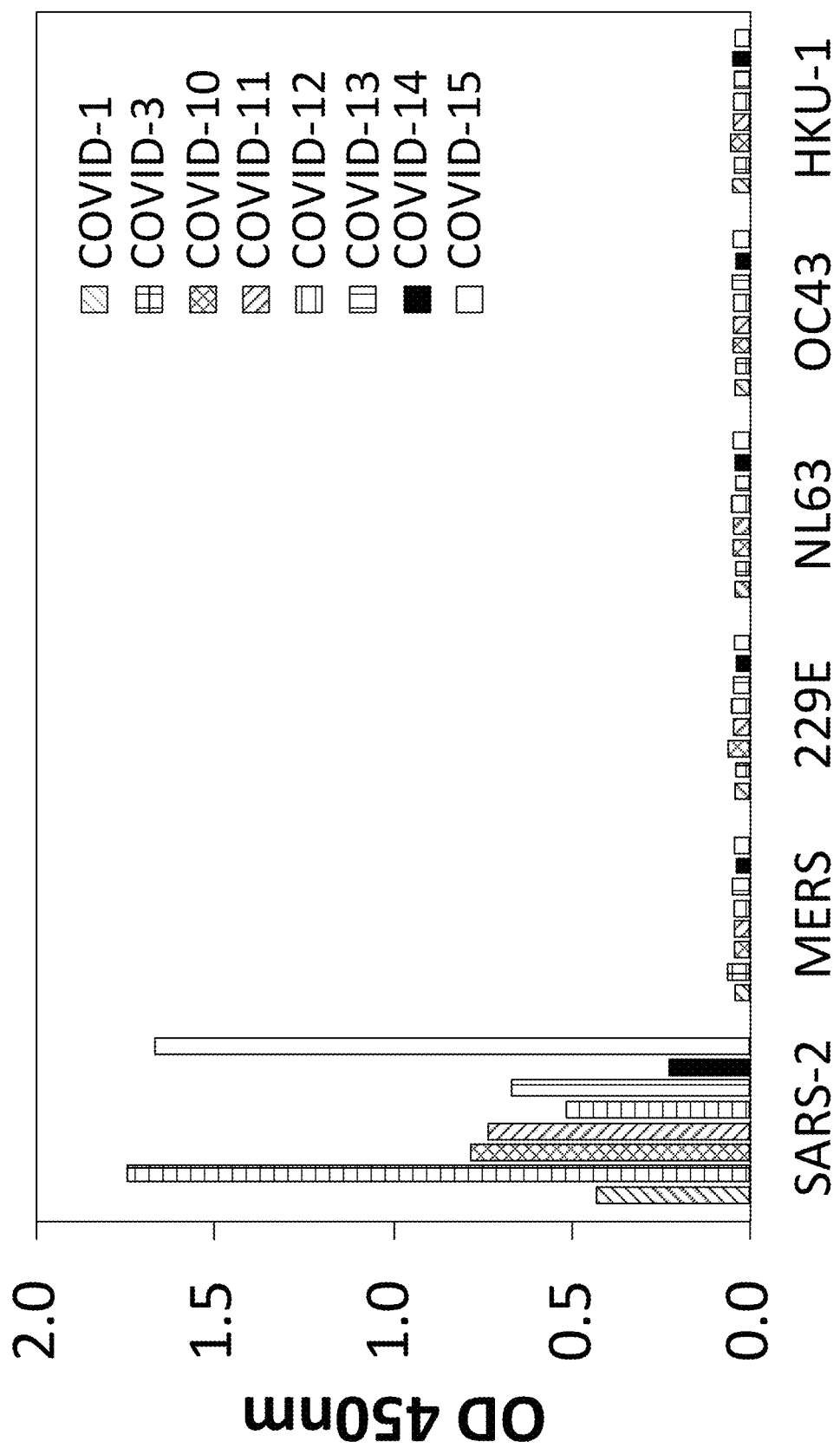
FIG. 11 depicts specific inhibition of SARS-CoV-2 binding of S protein in an assay of the present disclosure. S proteins from other coronaviruses did not cross react with the coated ACE2 on the ELISA plate.

To establish the specificity of the assay, COVID-19 sera was tested for cross-reactivity with S proteins from other high-circulating human alpha coronaviruses 229E and NL63, beta coronaviruses OC43 and HKU1, and MERS coronavirus. Sequence identity between SARS-CoV-2 S and the S proteins of these other coronaviruses is less than 32% (27.3% with 229E; 26.2% with NL63; 31% with OC43 and HKU1; 31.9% with MERS). Sequence identity with SARS-CoV-1 S protein is highest, at 77%, but that coronavirus was not tested as it is not currently in circulation. The S proteins were cloned and expressed using methods similar to that for the SARS-CoV-2 S protein and assayed alongside. Eight COVID-19 sera tested were obtained commercially and were verified for IgG and IgM using the InBios SARS-CoV-2 Detect™ IgG and IgM ELISAs as well as inhibition of S protein-ACE2 binding by the ELISA methods described herein. No cross-reactivity was observed between the COVID-19 sera and any of the other coronavirus S proteins, indicating that this assay was specific for SARS-CoV-2 and that the sera do not harbor antibodies that can cross react with other related S proteins (FIG. 11).

Example 4: Validation of ELISA Assay by PRNT

Figure 12:
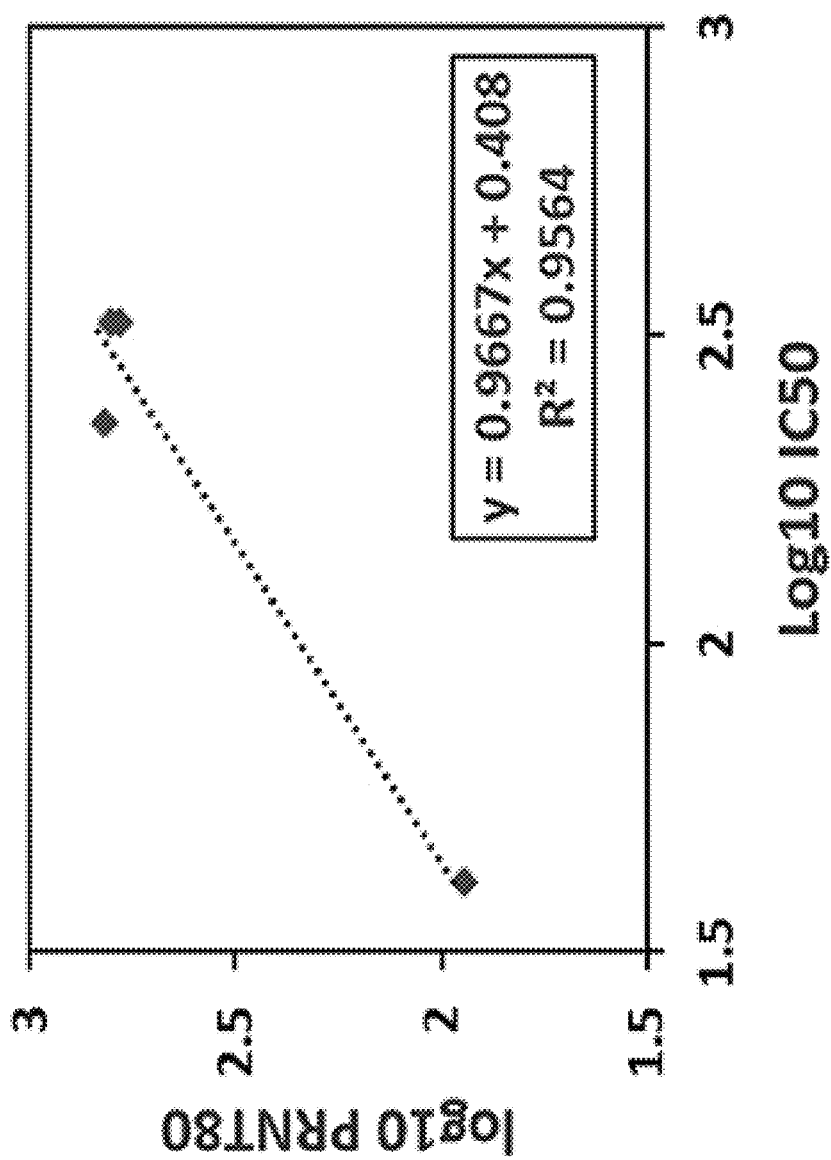
FIG. 12 depicts the R2 values for the $\log_{10}$ IC50 obtained by plaque reduction neutralization assay (PRNT) (vertical axis) and by an assay of the present disclosure (horizontal axis).

The ability of the ELISA to mimic a live virus neutralization assay was studied by comparing the inhibition measured by both assays. Plaque reduction neutralization assays (PRNT) were performed on four COVID-19 sera using live SARS-CoV-2 to generate PRNT80, which is a measure of the dilution of sera that can cause an 80% reduction in viral plaque formation. The alignment of PRNT80 and the IC50 values generated from the 2-step ELISA was then affirmed by plotting the log values of both and obtaining the R2 value (FIG. 12). Very good alignment was observed between the IC50 and PRNT80 values for the subset of samples tested, with a R2 value of 0.9564, indicating agreement. The four COVID-19 sera used for this study were also tested for presence of direct binding Abs to S protein or RBD by indirect ELISA and were found to harbor binding Abs to both antigens (Table 4). These results make it evident that the 2-step ELISA can serve as a surrogate serological assay for viral neutralization assays, and the inhibition of S protein-ACE2 binding observed in the ELISA is indeed responsible for neutralizing viral binding and entry into the host cell.

TABLE 4

| Sample | Spike IgM | Spike IgG | RBD IgM | RBG IgG |
|---|---|---|---|---|
| COVID-7 | High | High | High | High |
| COVID-8 | High | High | High | Low |
| COVID-9 | High | High | High | High |
| COVID-10 | High | High | High | High |

Example 5: ELISA Methods

Protein expression and purification: The S, RBD and ACE2 proteins were recombinantly expressed as follows. The 1211 amino acids for full length SARS-CoV-2 Spike protein ectodomain coded by the region spanning 923-4813 of the open reading frame, was cloned into the pcDNA3.1 (+)-Hygro vector along with a T4 fibritin trimerization domain in the C-terminus to ensure assembly into the natural trimeric conformation of S. A 6×-His tag and two iterations of the strep-tag were also added to the C-terminus. Similar Spike protein constructs were created for other related coronaviruses, namely HKU1, MERS, 229E, OC43 and NL63 and were expressed and purified as for SARS-CoV-2. For the RBD, residues 319-541 of the Spike protein containing the N-terminal secretion signal of the Spike protein were cloned into the pcDNA3.1(+)-Hygro vector with the T4 fibritin trimerization domain, 6×-His and Strep tags. Expi-CHO cells were transfected and cultures were harvested 10-14 days later. The secreted protein was purified from the supernatant using Nickel-NTA affinity chromatography and eluted with Imidazole. A mammalian-codon-optimized gene encoding human ACE2 residues 1-615 C-terminally fused to a human IgG Fc region (SEQ ID NO:5) was synthesized and subcloned into the eukaryotic expression vector pcDNA3.1(+)-Hygro. Expi-CHO cells were transfected and cultures were harvested 10-14 days later. The secreted protein was purified from the supernatant using Protein A affinity chromatography. Eluates were dialyzed and concentrated for storage and yield. Purity of all proteins was assessed by SDS-PAGE and spectroscopically by measuring absorbance at 280 nm.

Sera specimens: RT-PCR confirmed COVID-19 sera were either obtained from commercial sources (ABO Pharmaceuticals, San Diego, Calif.) or through collaborators. COVID-19 sera (COVID-1 through COVID-6 and COVID-11-COVID-15) obtained from ABO Pharmaceuticals were used to validate the assay while those obtained from collaborators (COVID-7 through COVID-10) were used to validate by PRNT80. All sera were also tested for presence of SARS-CoV-2 specific IgG and IgM by the FDA-EUA InBios SARS-CoV-2 IgG and IgM Detect™ ELISAs. Further, the sera were characterized for total binding IgM and IgG to S protein and RBD using indirect ELISAs in which S protein and RBD served as the direct capture antigens. As controls in ELISA, archived normal human sera (NHS) collected before December 2019 (InBios International Inc., Seattle, Wash.) were used.

Binding Inhibition calculations: Binding was observed in the presence of COVID-19 plasma/sera (COVID) compared to normal human sera (NHS), qualified as pre-COVID-19 and free of any cross reactivity. Uninhibited binding was defined as the binding of S protein to coated ACE2 in the absence of neutralizing Abs. A loss of color development indicated that the interaction between ACE2 and S protein was inhibited. Binding inhibition was calculated based on the color intensity of S protein bound to ACE2 in the presence or absence of COVID-19 serum. Percent binding inhibition was thus calculated as ((OD 450 nm NHS−OD 450 nm COVID/OD 450 nm NHS)*100). IC50 was defined as the point dilution at which 50% binding inhibition was observed. IC50 was calculated using the "Quest Graph™ IC50 Calculator which employs a 4-parameter logarithmic regression model (11). Input serum were generated by first preparing a 1/10 dilution of 20 uL serum and 180 uL SDB. Two-fold serial dilutions were prepared from this sample to create sample dilutions ranging from 1/10 to 1/1280. The minimum inhibition value was taken as the average signal of NHS samples included in the plate.

Viral Neutralization assays: Plaque Reduction Neutralization Assays (PRNT) were performed as previously described. Briefly, serial dilutions of heat inactivated COVID-19 serum and 600 plaque-forming units (PFU)/ml solution of SARS-CoV-2/WA/20 (BEI resources) were mixed 1:1 in DPBS (Fisher Scientific) and 0.3% gelatin (Sigma G7041) and incubated for 30 min. at 37° C. Serum/virus mixtures were added in duplicate, along with virus only and mock controls, to Vero E6 cells (ATCC) and incubated for 1 hr at 37° C. followed by overlaying with Avicel RC-591 (FMC). Plates were then incubated for 2 days at 37° C. Following incubation, overlay was removed and cells were stained with 1% crystal violet (Sigma-Aldrich). Plaques were enumerated and serum dilutions that resulted in 80% plaque neutralization was calculated relative to the virus-only control as PRNT80 outcome for each serum tested.

Correlation between PRNT and SARS-CoV-2 Neutralizing Ab (NAb) Detect™ ELISA: To correlate PRNT and IC50 estimates, the log of the PRNT80 was plotted against the log of the IC50 values for each serum sample. The points were fitted to obtain R2 values to indicate correlation of the two values for each sample. Data Analysis: All analysis and graphing were done using Microsoft Excel 15, Quest Graph™ IC50 Calculator and RStudio Version 1.2.1335.

In limited initial tests, 5 human serum samples containing known anti-mouse antibodies were tested to identify potential cross-reactivity. No samples were reactive (0/5 false positive), as expected since no mouse-derived antibodies are present in this assay. Because elevated rheumatoid factor (RF) titers are known to cross-react with and/or interfere with the NAb assay, a suitable blocker that mitigates RF interference without affecting true positive and negative signals may be used, however.

Example 6: ELISA and Kit

An ELISA may be conducted using materials as described herein, particularly as in Examples 1-5.

The assay is for in vitro diagnostic (IVD) use only and may be for prescription use only.

Intended Use

The SCoV-2 Detect™ Neutralizing Ab ELISA (InBios) is an enzyme-linked immunosorbent assay intended for the qualitative direct detection of total neutralizing antibodies to SARS-CoV-2 in human serum and plasma (dipotassium EDTA, lithium heparin, and sodium citrate). The SCoV-2 Detect™ Neutralizing Ab ELISA is intended for use as an aid in identifying individuals with an adaptive immune response to SARS-CoV-2, indicating recent or prior infection.

At this time, it is unknown for how long antibodies persist following infection and if the presence of neutralizing antibodies confers protective immunity. The SCoV-2 Detect™ Neutralizing Ab ELISA should not be used to diagnose or exclude acute SARS-CoV-2 infection.

Testing may be limited to laboratories certified under the Clinical Laboratory Improvement Amendments of 1988 (CLIA), 42 U.S.C. § 263a, that meet the requirements to perform high complexity tests, or other laboratories with similar capabilities in other jurisdictions.

Results are for the detection of SARS CoV-2 total neutralizing antibodies. Antibodies to SARS-CoV-2 are generally detectable in blood several days after initial infection, although the duration of time neutralizing antibodies are present post-infection is not well characterized. Individuals may have detectable virus present for several weeks following seroconversion.

Laboratories within the United States and its territories are required to report all results to the appropriate public health authorities.

The sensitivity of SCoV-2 Detect™ Neutralizing Ab ELISA early after infection is unknown. Negative results do not preclude acute SARS-CoV-2 infection. If acute infection is suspected, direct testing for SARS-CoV-2 is necessary.

False positive results for SCoV-2 Detect™ Neutralizing Ab ELISA may occur due to cross-reactivity from pre-existing antibodies or other possible causes.

The SCoV-2 Detect™ Neutralizing Ab ELISA is only for use under the Food and Drug Administration Emergency Use Authorization (EUA).

Summary and Explanation of the Test

The novel coronavirus, SARS-CoV-2 (the causative agent of COVID-19), has been responsible for the pandemic of pneumonia-like symptoms and associated deaths from late 2019 and into 2021. The detection of the initial outbreak in the Hubei Province of China and the subsequent need for an effective diagnosis were quickly described (Li, X., Geng, M., Peng, Y., Meng, L., & Lu, S. (2020). Molecular immune pathogenesis and diagnosis of COVID-19. Journal of Pharmaceutical Analysis. https://doi.org/10.1016/J.JPHA.2020.03.001; Wu, F., Zhao, S., Yu, B., Chen, Y.-M., Wang, W., Song, Z.-G., Hu, Y., Tao, Z.-W., Tian, J.-H., Pei, Y.-Y., Yuan, M.-L., Zhang, Y.-L., Dai, F.-H., Liu, Y., Wang, Q.-M., Zheng, J.-J., Xu, L., Holmes, E. C., & Zhang, Y.-Z. (2020). A new coronavirus associated with human respiratory disease in China. Nature, 579(7798), 265-269. https://doi.org/10.1038/s41586-020-2008-3; Zhou, P., Yang, X.-L., Wang, X.-G., Hu, B., Zhang, L., Zhang, W., Si, H.-R., Zhu, Y., Li, B., Huang, C.-L., Chen, H.-D., Chen, J., Luo, Y., Guo, H., Jiang, R.-D., Liu, M.-Q., Chen, Y., Shen, X.-R., Wang, X., . . . Shi, Z.-L. (2020). A pneumonia outbreak associated with a new coronavirus of probable bat origin. Nature, 579(7798), 270-273. https://doi.org/10.1038/s41586-020-2012-7).

It has been reported that RT-PCR-confirmed SARS-CoV-2 positive patients may seroconvert and develop antibodies against SARS-CoV-2 antigens anywhere from 6-21 days after the onset of clinical symptoms (Okba, N. M. A., Muller, M. A., Li, W., Wang, C., GeurtsvanKessel, C. H., Corman, V. M., et al. (2020). Severe Acute Respiratory Syndrome Coronavirus 2-Specific Antibody Responses in Coronavirus Disease 2019 Patients. Emerging Infectious Diseases, 26(7).). The specific and reliable detection of human antibodies capable of neutralizing SARS-CoV-2 remains a key method to monitor infections, for effective contact tracing, and for serosurveillance (Okba et al., 2020).

The SCoV-2 Detect™ Neutralizing Ab ELISA is a qualitative immunoassay for the detection of antibodies inhibiting the interaction between the human angiotensin converting enzyme 2 (ACE2) receptor and SARS-CoV-2 Spike (S) protein.

Principle of the Test

The SCoV-2 Detect™ Neutralizing Ab ELISA is a qualitative competitive inhibition ELISA that detects antibodies to SARS-CoV-2 and that prevent binding of the virus to the human ACE2 receptor. Serum or plasma specimens are first diluted and pre-incubated with proprietary monoclonal antibody (mAb) premixed with recombinant SARS-CoV-2 S protein. Then the mixture is transferred to ACE2 receptor protein-coated wells. After incubation and washing, the S protein-mAb immune complex remains bound on the plate surface unless the interaction was inhibited by neutralizing antibodies (NAbs) in the specimen. The protein-protein interaction is designed to mimic the virus-host interaction. Secondary antibody conjugated to horseradish peroxidase (HRP) targeting the mAb is then added to each well. After incubation, the ELISA wells are washed before a tetramethylbenzidine (TMB) substrate is added. An acidic solution is finally used to stop the reaction and the degree of enzymatic turnover of the substrate is determined by measuring optical density (OD) at 450 nanometers.

Positive and Negative Controls are provided to ensure the integrity of the assay and to determine the assay-specific threshold. Up to 92 specimens may be evaluated with each kit (as the controls are run in duplicate). The entire procedure takes approximately 3 hours from preparing the Sample Dilution Buffer, or approximately 1 hour and 40 minutes once sample dilution is started.

Kit Contents

Warning: Do not use any reagents where damage to the packaging has occurred.

The kit contains the following reagents:

1. COATED MICROTITER STRIPS FOR SCOV-2 NAB ELISA: Strip holder in a resealable foil pouch, containing 96 polystyrene microtiter wells coated with receptor protein in each well. Stable at 2-8° C. until the expiration date.

2. SCOV-2 NAB NEGATIVE CONTROL: One vial, 150 µL. Negative Control sample. The Negative Control will aid in monitoring the integrity of the kit and in interpreting sample results. Stable at 2-8° C. until the expiration date.

3. SCOV-2 NAB POSITIVE CONTROL: One vial, 150 µL. Positive Control contains neutralizing antibodies and will aid in monitoring the integrity of the kit. Stable at 2-8° C. until the expiration date.

4. 100× NEUTRALIZATION MIX FOR SCOV-2 NAB: One vial, 300 µL. This contains recombinant Spike antigen pre-mixed with proprietary secondary antibody. The 100× Neutralization Mix is added to the Neutralization Dilution Buffer prior to its use. Stable at 2-8° C. until the expiration date.

5. NEUTRALIZATION DILUTION BUFFER FOR SCOV-2 NAB: One bottle, 25 mL. Tris-HCl buffered solution (pH 7.2-7.6) with Tween 20, preservative and additives. The Neutralization Dilution Buffer will be used to dilute 100× Neutralization Mix prior to mixing with samples and controls. Stable at 2-8° C. until the expiration date.

6. 100× CONJUGATE FOR SCOV-2 NAB: One vial, 100 µL, containing horseradish peroxidase-labeled antibody in a Tris-based buffer with preservative. Stable at 2-8° C. until the expiration date.

7. CONJUGATE DILUENT FOR SCOV-2: One bottle, 9 mL, is to be used to dilute the 100× conjugate before adding to the ELISA plate. Stable at 2-8° C. until the expiration date.

8. 10× WASH BUFFER: One bottle, 120 mL. 10× concentrated phosphate buffered saline with Tween 20 (pH 6.8-7.0). Stable at 2-8° C. until the expiration date.

9. LIQUID TMB SUBSTRATE: One bottle, 12 mL, ready to use. Contains 3, 3', 5, 5'-tetramethylbenzidine (TMB) and hydrogen peroxide in a citric acid-citrate buffer (pH 3.3-3.8). Stable at 2-8° C. until the expiration date. Note: The substrate should always be stored in the light-protected bottle provided.

10. STOP SOLUTION: One bottle, 6 mL, ready to use. 1N Sulfuric Acid. Used to stop the reaction. Stable at 2-8° C. until the expiration date.

Warning: Strong acid. Wear protective gloves, mask and safety glasses. Dispose all materials according to all applicable safety rules and regulations.

Materials and Equipment Required but not Provided
  ELISA spectrophotometer capable of absorbance measurement at 450 nm
  Biological or high-grade water
  Appropriately sized beakers and stir bars
  Vacuum pump
  Automatic plate washer
  37° C. incubator without CO2 supply
  1-10 µL single-channel pipettors, 50-200 µL single- and multichannel pipettors
  Polypropylene tubes or 96 well dilution plates
  Parafilm or plastic plate cover
  Timer
  Vortex WARNINGS AND PRECAUTIONS (As of Oct. 22, 2021 for use in the US, some warning and precautions may become inapplicable at later times or may differ in other jurisdictions)
  For use Under Emergency Use Authorization only.
  in vitro diagnostic use only.
  For prescription use only.
  This product has not been FDA cleared or approved, but has been authorized for emergency use by FDA under an EUA for use by authorized laboratories.
  This product has been authorized only for detecting the presence of neutralizing antibodies to SARS-CoV-2, not for any other viruses or pathogens.
  The emergency use of this product is only authorized for the duration of the declaration that circumstances exist justifying the authorization of emergency use of in vitro diagnostics for detection and/or diagnosis of COVID-19 under Section 564(b)(1) of the Federal Food, Drug, and Cosmetic Act, 21 U.S.C. § 360bbb-3(b)(1), unless the declaration is terminated or authorization is revoked sooner.
  Laboratories within the United States and its territories are required to report all results to the appropriate public health authorities
  Follow standard precautions. All specimens and controls should be considered potentially infectious and handled in accordance with good laboratory procedure.

Safety Precautions
  Dispose of hazardous or biologically contaminated materials according to the practices of your institution. Discard all materials in a safe and acceptable manner and in compliance with prevailing regulatory requirements.
  Wear protective clothing, eye protection and disposable gloves while performing the assay. Wash hands thoroughly afterwards.
  Do not eat, drink, smoke, or apply cosmetics in the laboratory where immunodiagnostic materials are being handled.
  Do not pipette by mouth.

Technical Precautions
  This test must be performed on human serum or plasma only. The use of whole blood or other specimen matrices has not been validated.
  Do not mix various lots of any kit component within an individual assay.
  All reagents must be equilibrated to room temperature (15-25° C.) before commencing the assay. The assay will be affected by temperature changes.
  Samples should not be frozen and thawed more than once.
  Dispense reagents directly from bottles using clean pipette tips. Transferring reagents may result in contamination.
  Unused microtiter wells must be resealed immediately in the resealable foil pouch with the desiccant provided. Failure to do so may cause erroneous results with those unused microwells.
  Do not use any component beyond the expiration date shown on its label.
  Avoid exposure of the reagents to excessive heat or direct sunlight during storage and incubation.
  Some reagents may form a slight precipitate, mix gently before use. Do not vortex the 100× Neutralization Mix for SCoV-2 NAb.
  Incomplete washing will adversely affect the outcome and assay performance.
  To minimize potential assay drift due to variation in the substrate incubation time, care should be taken to add the stop solution into the wells in the same order and speed used to add the TMB solution.
  Avoid microbial contamination of reagents.
  Avoid contamination of the TMB Substrate Solution with the Conjugate Solution. The TMB Substrate Solution should be clear in color; a blue color change prior to use may indicate contamination has occurred.
  Use a clean disposable pipette tip for each reagent, standard, control or specimen.
  Cover working area with disposable absorbent paper.

Chemical Hazard
  Safety Data Sheets (SDSs) are available for all components of this kit. Review all appropriate SDSs before performing this assay and don required Personal Protective Equipment (PPE) as noted. Avoid all contact between hands and eyes or mucous membranes during testing. If contact does occur, consult the applicable SDS for appropriate treatment.

Specimen Collection and Preparation
  Only human serum or plasma (with dipotassium EDTA, lithium heparin, and sodium citrate) should be used for this assay, and the usual precautions for venipuncture should be observed. To obtain serum, blood obtained by venipuncture without anticoagulant should be allowed to clot at room temperature (20-25° C.) for 30 to 60 minutes and then centrifuged according to the Clinical and Laboratory Standards Institute (CLSI Approved Guideline—Procedures for the Handling and Processing of Blood Specimens for Common Laboratory Tests; GP44).
  Testing should be performed as soon as possible after collection. Do not leave sera or plasma at room temperature for prolonged periods. Separated serum or plasma should remain at 20-25° C. for no longer than 8 hours. If assays are not completed within 8 hours, samples should be refrigerated at 2-8° C. If assays are not completed within 48 hours, or the separated serum or plasma is to be stored beyond 48 hours, serum or plasma should be frozen at or below −20° C.
  Samples should not be frozen and thawed more than once. Frost-free freezers are not suitable for sample storage.
  Frozen samples should be thawed to room temperature and mixed thoroughly by gentle swirling or inversion prior to use. Always quick spin before use.
  If sera or plasma are to be shipped, they should be packed in compliance with Federal Regulations covering transportation of infectious agents.
  Do not use sera or plasma if any indication of microbial growth is observed.

Test Procedure
  CAUTION: The test procedure must be strictly followed. Any deviations from the procedure may produce erroneous results. Bring all reagents and specimens to room temperature (~25° C.) before use. Thoroughly mix the reagents and samples before use by gentle inversion. NOTE: For long-term storage, serum and plasma samples should not be frozen and thawed more than once. Sera and plasma should be further divided into small aliquots and stored at −20° C. or below.
  This assay is intended to be performed manually. Plate washing must be performed using a properly calibrated automated plate washer. This kit has not been optimized by InBios for use with a specific automated ELISA processing system. Use with an automated ELISA processing system will require proper validation.
  Preparation of Reagents:
  Preparation of Sample Dilution Buffer
    Dilute 250 µL of the 100× Neutralization Mix for SCoV-2 NAb into the 25 mL bottle of Neutralization Dilution Buffer for SCoV-2 NAb, and gently invert bottle several times. Do not vortex. Allow this bottle to equilibrate at room temperature for at least 1 hour before proceeding. Once mixed, this bottle should be used fresh and not stored for further use. Alternatively, use a clean pipette to remove the required volume of Neutralization Dilution Buffer and add the necessary volume of 100× Neutralization Mix for SCoV-2 NAb into a clean polypropylene test tube in order to maintain the 1:100 ratio.
  Preparation of 1× Wash Buffer
    Dilute the 10× Wash Buffer to 1× using Biological or High-Grade Water. To prepare a 1× Wash Buffer solution, mix 120 mL 10× Wash Buffer with 1080 mL distilled (or deionized) water. Mix thoroughly to ensure that any precipitate is dissolved and that the solution is uniform. Once diluted to 1×, the solution can be stored at room temperature for up to 6 months. Properly label the 1× Wash Buffer solution and carefully note the expiration date on the label. Check for contamination prior to use. Discard if contamination is suspected.
  Microtiter Strip Wells
    Select the number of coated wells required for the assay. The remaining unused wells should be repackaged immediately with the supplied desiccant and stored at 2-8 °C until ready to use or expiration.

Preparation of Conjugate Solution

Add 90 µL of 100× Conjugate for SCoV-2 NAb directly to the 9 mL bottle of Conjugate Diluent for SCoV-2 NAb (1 part:100 parts). Alternatively, use a clean pipette to remove the required volume of Conjugate Diluent and add the necessary volume of 100× Conjugate for SCoV-2 ELISA into a clean polypropylene test tube in order to maintain the 1:100 ratio. Mix by inverting the solution several times. This conjugate solution should be prepared immediately prior to running the assay and discarded immediately after use.

Assay Procedure:

1. Positive and negative controls should be assayed in duplicate, and run on every plate, each time an assay is performed. Test unknown serum and plasma samples in singlicate or duplicate. Up to ninety-two test specimens can be tested in singlicate with an entire plate. Immediately place any unused ELISA plate wells back into the original foil packaging with the provided desiccant, properly seal and store at 2-8° C.

2. Dilute each control and each test specimen 1:20 by adding 8 µL of sample to 152 µL of equilibrated Sample Dilution Buffer for SCoV-2 NAb. Dilute samples into a dedicated sample dilution block or appropriately sized tubes. Mix samples well by pipetting. Cover the top of the plate with parafilm (or a plastic plate cover) and remove any excess parafilm from the edges of the plate. Incubate these samples at 37° C. for 30 minutes.

3. Mix samples again via pipetting. Add 50 µL of the 1:20 diluted controls and test specimens onto the appropriate locations in the SCoV-2 Antigen Coated Microtiter Strip plate (ELISA plate). Note and record the locations of all controls and test samples in the ELISA plate wells.

4. Cover the top of the plate with parafilm (or a plastic plate cover) and remove any excess parafilm from the edges of the plate. Note: This is to make sure the temperature distribution is evenly spread out in all wells from bottom and sides; any extra parafilm can be cut off once the top is sealed to block evaporation 5. Incubate the plate(s) at 37° C. for 30 minutes in an incubator. Note: Do not stack plates on top of each other. They should be spread out as a single layer. This is very important for even temperature distribution. Do not use CO2 or other gases. Do not place plates in contact with any wet substances such as wet paper towels etc.

6. After the incubation, wash the plate 6 times with an automatic plate washer using 1× Wash Buffer. Use 300 µL per well in each wash cycle.

7. Add 50 µL per well of the freshly prepared Conjugate Solution (made from 100× Conjugate diluted into Conjugate Diluent) into all wells using a multi-channel pipettor. Discard the remaining Conjugate Solution.

8. Cover the plate with parafilm or a plastic plate cover and incubate the plate(s) at 37° C. for 30 minutes in an incubator.

9. After the incubation, wash the plate 6 times with the automatic plate washer using 1× Wash Buffer. Use 300 µL per well in each wash cycle.

10. Add 75 µL per well of Liquid TMB substrate into all wells using a multi-channel pipettor.

11. Incubate the plate uncovered at room temperature in the dark, for 10 minutes.

12. Add 50 µL per well of Stop Solution into all appropriate wells using a multi-channel pipetter. Make sure to add the Stop Solution in the same order and at approximately the same speed at which the TMB was applied. (Note: As the TMB substrate produces an enzymatic reaction with the HRP-conjugate, it is critical this incubation time point is followed as closely as possible). Let the plate stand, uncovered at room temperature, for 1 minute.

13. Read the optical density at 450 nm (OD450) with a microplate reader. DO NOT SUBTRACT OR NORMALIZE ANY BLANK VALUES OR WELLS.

14. Record the raw OD450 and evaluate the sample status as indicated in the Quality Control and Interpretation of Results sections.

Quality Control

Each kit contains positive and negative controls. These controls are intended to monitor for substantial reagent failure. The positive control will not ensure precision at the assay limit of detection. The test is invalid if the control sample values do not fall in the pre-established OD value ranges. If the test is invalid, the results cannot be used, and the testing must be repeated. Quality Control (QC) requirements must be performed in conformance with local, state, and/or federal regulations or accreditation requirements and your laboratory's standard Quality Control procedures. It is recommended that the user refer to CLSI C24 and 42 CFR 493.1256 for guidance on appropriate QC practices. The results below are given strictly for guidance purposes only and applicable for spectrophotometric readings only.

In order to establish the test is valid, first calculate the mean (average) negative and positive control raw OD450 values as shown in the following Tables 5-6 and 8, which include example values.

TABLE 5

| SCoV-2 Positive Control | |
| --- | --- |
| | OD450 |
| Replicate 1 | 0.527 |
| Replicate 2 | 0.548 |
| Sum | 1.075 |

Average Positive Control=1.075÷2=0.5375

TABLE 6

| SCoV-2 Negative Control | |
| --- | --- |
| | OD450 |
| Replicate 1 | 2.675 |
| Replicate 2 | 2.824 |
| Sum | 5.499 |

Average Negative Control=5.499÷2=2.7495

Finally, verify that the quality control requirements, listed in the table below, are fulfilled.

TABLE 7

| Quality Control Requirements | |
| --- | --- |
| Control | Requirement |
| Positive Control | OD < 1.2 |
| Negative Control | OD > 1.5 |

The results on the table above must be obtained for the assay to be considered valid. Non-fulfillment of these criteria is an indication of deterioration of reagents or an error in the test procedure and the assay must be repeated.

Interpretation of Results

The cut-off value was determined by screening a large number (277) of normal human serum (NHS) samples that were collected prior to the COVID-19 outbreak (~November, 2019). The cut-off selection was performed by estimating the mean of the negative specimens plus three (3) standard deviations.

Calculate Signal Inhibition (SI %): The test result of the unknown sample is determined by calculating Signal Inhibition. Signal Inhibition can be determined from the OD values of the sample and the Negative Control:

Signal Inhibition (%)=(1−[Sample OD÷Negative Control OD])*100%

If unknown samples were tested in duplicate, then calculate the average optical density (OD450) to input as the Sample OD.

TABLE 8

Calculate the SI % for a Sample

| Sample ID | Raw OD450 |
|---|---|
| Unknown Sample #1 | 1.321 |
| Negative Control | 2.985 |

SI=(1−[Sample OD÷Negative Control OD])*100%

SI %=(1−[1.321÷2.985])*100%=55.7%

TABLE 9

| SI %* | Results | Interpretation |
|---|---|---|
| >25% | Positive | Neutralizing antibodies for SARS-CoV-2 are detected. |
| 15-25% | Retest | Retest sample in duplicate. If retested Signal Inhibition (%) is ≥20%, then neutralizing antibodies for SARS-CoV-2 are detected. If retested SI % is <20%, then neutralizing antibodies for SARS-CoV-2 are not detected. |
| <15% | Negative | Neutralizing antibodies for SARS-CoV-2 are not detected. |

*Signal Inhibition Results should not be reported to the end user. The clinical applicability of detection or correlation with neutralizing activity for antibodies to SARS-CoV-2 at ≥20% SI is currently unknown and results cannot be interpreted as an indication of degree of immunity or protection from infection. Because SARS-CoV-2 neutralizing antibody assays are not standardized, and the performance characteristics of each SARS-CoV-2 neutralizing antibody test is uniquely established, results from different SARS-CoV-2 neutralizing antibody assays cannot be compared.

Limitations

This test is designed for qualitative detection of SARS-CoV-2 neutralizing antibodies.

To be used only under the conditions of the FDA Emergency Use Authorization.

Use of the SCoV-2 Detect™ Neutralizing Ab ELISA is limited to laboratory personnel who have been trained. Not for home use.

Performance has only been established with the specimen types listed in the Intended Use. Other specimen types have not been evaluated and should not be used with this assay.

The assay performance characteristics have not been established for visual result determination.

The assay has not been evaluated with fingerstick specimens. This test is not authorized for use with fingerstick whole blood.

Results from antibody testing should not be used to diagnose or exclude acute COVID-19 infection or to inform infection status.

A positive result may not indicate previous SARS-CoV-2 infection. Consider other information, including clinical history and local disease prevalence, in assessing the need for a second but different serology test to confirm an immune response.

A negative result for an individual subject indicates absence of detectable anti-SARS-CoV-2 neutralizing antibodies. Negative results do not preclude SARS-CoV-2 infection and should not be used as the sole basis for patient management decisions. The sensitivity of this assay early after infection is unknown.

A negative result can occur if the quantity of the anti-SARS-CoV-2 antibodies present in the specimen is below the detection limit of the assay, or the antibodies that are detected are not present during the stage of disease in which a sample is collected. Direct testing with a molecular diagnostic should be performed to evaluate for acute SARS-CoV-2 infection in symptomatic individuals.

It is unknown at this time if the presence of antibodies to SARS-CoV-2 confers immunity to re-infection.

False positive results may occur due to cross-reactivity from pre-existing antibodies or other possible causes.

False positive results due to cross-reactivity with Rheumatoid Factor (RF) can occur.

Not for the screening of donated blood.

Samples that are hemolyzed should be avoided for analysis with this assay.

Results from immunosuppressed patients must be interpreted with caution.

Assay results should be interpreted only in the context of other laboratory findings and the total clinical status of the patient.

The performance of this device has not been established in individuals that have received a COVID-19 vaccine. The clinical significance of a positive or negative antibody result following COVID-19 vaccination has not been established, and the result from this assay should not be interpreted as an indication or degree of protection from infection after vaccination.

The performance of this test was established based on the evaluation of a limited number of clinical specimens collected in the US from March 2020 to March 2021. Clinical performance has not been established with all circulating variants but is anticipated to be reflective of the prevalent variants in circulation at the time and location of the clinical evaluation. Performance at the time of testing may vary depending on the variants circulating, including newly emerging strains of SARS-CoV-2 and their prevalence, which change over time.

Performance Characteristics

Clinical Evaluation

The Clinical Evaluation tested 135 retrospectively collected serum samples, from subjects who had been confirmed positive for SARS-CoV-2 by an EUA-authorized RT-PCR assay. Samples were confirmed positive or negative for neutralizing antibodies by Plaque Reduction Neutralization Test at 90% reduction level (PRNT90). The tables below show the Positive Percent Agreement (PPA) and Negative Percent Agreement (NPA) between the SCoV-2 Detect™ Neutralizing Ab ELISA and the PRNT comparator assay. 95% confidence intervals (95% CI) were calculated by the Wilson score method.

TABLE 10

|  |  | Plaque Reduction Neutralization Test (PRNT$_{90}$) | |
| --- | --- | --- | --- |
|  |  | Positive | Negative |
| SCoV-2 Detect ™ Neutralizing Ab ELISA | Positive | 51 | 3 |
|  | Negative | 2 | 79 |
|  | Positive Percent Agreement [95% CI] | 96.2% [87.3%-99.0%] | NA |
|  | Negative Percent Agreement [95% CI] | NA | 96.3% [89.8%-98.8%] |

Cross-Reactivity (Analytical Specificity)

Cross-reactivity of the SCoV-2 Detect™ Neutralizing Ab ELISA Kit was evaluated by testing SARS-CoV-2 seronegative specimens from patients with antibodies to other viral infections and autoantibodies which could potentially cause false positive results. SCoV-2 Detect™ Neutralizing Ab ELISA demonstrates no cross-reactivity against antibodies for influenza A, influenza B, hepatitis B, hepatitis C, human immunodeficiency, respiratory syncytial viruses, antinuclear antibodies, dengue, zika, chikungunya, or antibodies against other human coronaviruses. Cross-reactivity was observed with high RF (>2000 IU/mL) samples, but did not correlate to RF levels.

TABLE 11

| Category | Number of samples tested | Number reactive |
| --- | --- | --- |
| Anti-Influenza A/B | 5 | 0 |
| Anti-Hepatitis B | 5 | 0 |
| Anti-Hepatitis C | 5 | 0 |
| Anti-HIV | 20 | 0 |
| Anti-Nuclear Antibody | 5 | 0 |
| Anti-Dengue | 8 | 0 |
| Anti-Zika | 8 | 0 |
| Anti-Chikungunya | 8 | 0 |
| Anti-HKU1, OC43, 229E, NL63 | 5 | 0 |
| Anti-Respiratory Syncytial Virus | 4 | 0 |
| Rheumatoid Factor | 6 | 6 |

Example 7: Lateral Flow Assay Cassettes

A semi-quantitative SCoV-2 nAb lateral flow assay cassette test (FIG. 2A, FIG. 2B and FIG. 3) is an inhibition assay that measures the presence of antibodies in patient capillary finger prick blood, serum or plasma that interfere with the binding of SARS-CoV-2 Spike to its target, ACE2. ACE2 protein is immobilized on the lateral flow assay cassette membrane in the test line region (T) while the Spike protein is labeled with colloidal gold and dried onto the conjugate pad. Sample is introduced to the sample port and gold-labeled Spike protein is rehydrated and flows over the membrane-bound ACE2 test line. If SCoV-2 nAbs are absent, the gold-labeled Spike protein binds to ACE2 on the test line, generating a dark test line. If SCoV-2 Nabs are present, they interact with the gold-labeled Spike protein and prevent the Spike and its associated gold particles from binding to ACE2. Test line signal intensity is proportional to the amount of SCoV-2 nAbs present in the sample. Inhibition ranges from 100% (complete inhibition/no test line), to partial inhibition (weaker test line) and to 0% (no inhibition/strong test line). A smartphone app (FIG. 13) captures and analyzes the read-out for the presence of nAbs as strong, moderate or weak positive, or negative. Gold-labeled control antibodies preferentially bind to target immobilized in the control region (C). Control line signal intensity measures validity and consistency from test to test. Total time to test result is 20-30 minutes.

Test kits include single-use disposable lateral flow assay cassettes, all reagents needed for the assay, standards to calculate a standard curve, and positive and negative controls.

The smartphone app reader acquires an image of each lateral flow assay cassette and provides a semi-quantitative analysis of results. Machine-learning (also referred to as artificial intelligence) algorithms confirm that the user has scanned the correct test and aligned and properly centered the image. A bar/QR code uniquely identifies each kit lot. The smartphone app automatically acquires and aligns the image and interprets the results using a set of assay-specific machine learning models. The smartphone app generates a ratio score (LFE) based on the signal intensity ratio of the test:control line (T:C) and assigns a cut-off LFE value and range for each outcome (i.e., negative, weak positive, moderate positive, strong positive). Using the code for each kit lot, it mitigates lot-to-lot variability by adjusting the cut-off LFE value and range according to calibrators and standards used to qualify each batch of tests, without operator intervention. The cut-off LFE is determined by generating a receiver operating characteristic ROC curve from a panel of negative and positive samples. The cut-off LFE is established for each cassette lot and stored in a remote database for use by a reader and artificial intelligence, such as a smartphone, to apply correct thresholds for each lot.

Figure 13:
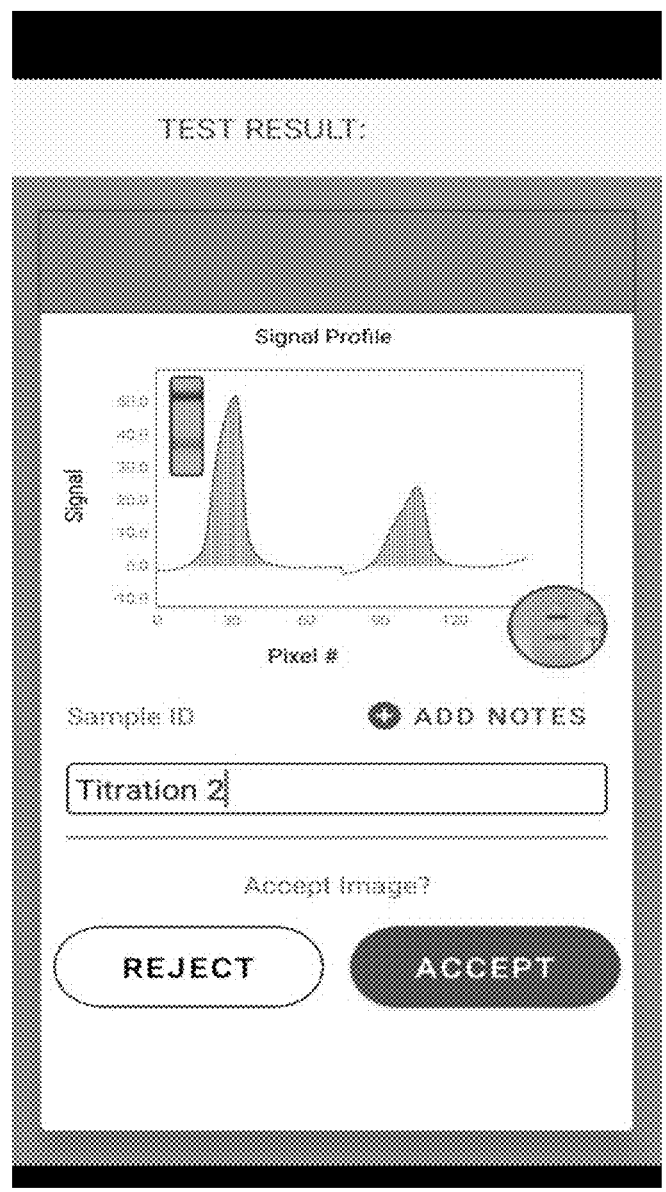
FIG. 13 depicts an example lateral flow assay cassette result displayed on a smartphone app in which the test line (right peak) has a reduced signal intensity relative to the control line (left peak).

Example results displayed on the smartphone app are presented in FIG. 13.

A specific SARS-CoV-2 test kit is intended for use a semi-quantitative of quantitative lateral flow assay to detect SARS-CoV-2 specific nAbs in patients, including vaccinated and unvaccinated patients and those who may be at high-risk for infection and/or severe disease. Capillary or venous whole blood, serum, or plasma may be used and is diluted prior to use.

The assay has a sensitivity of at least 90%, which means it will detect picomolar levels of nAbs to SARS-CoV-2 Spike protein.

The assay has a specificity of at least 95% for SARS-CoV-2.

The kit may contain a range of known concentrations of anti Spike RBD nAbs for calibration.

The shelf life of kits is at least 12 months or at least 18 months at room temperature (up to 30° C.).

Figure 14:
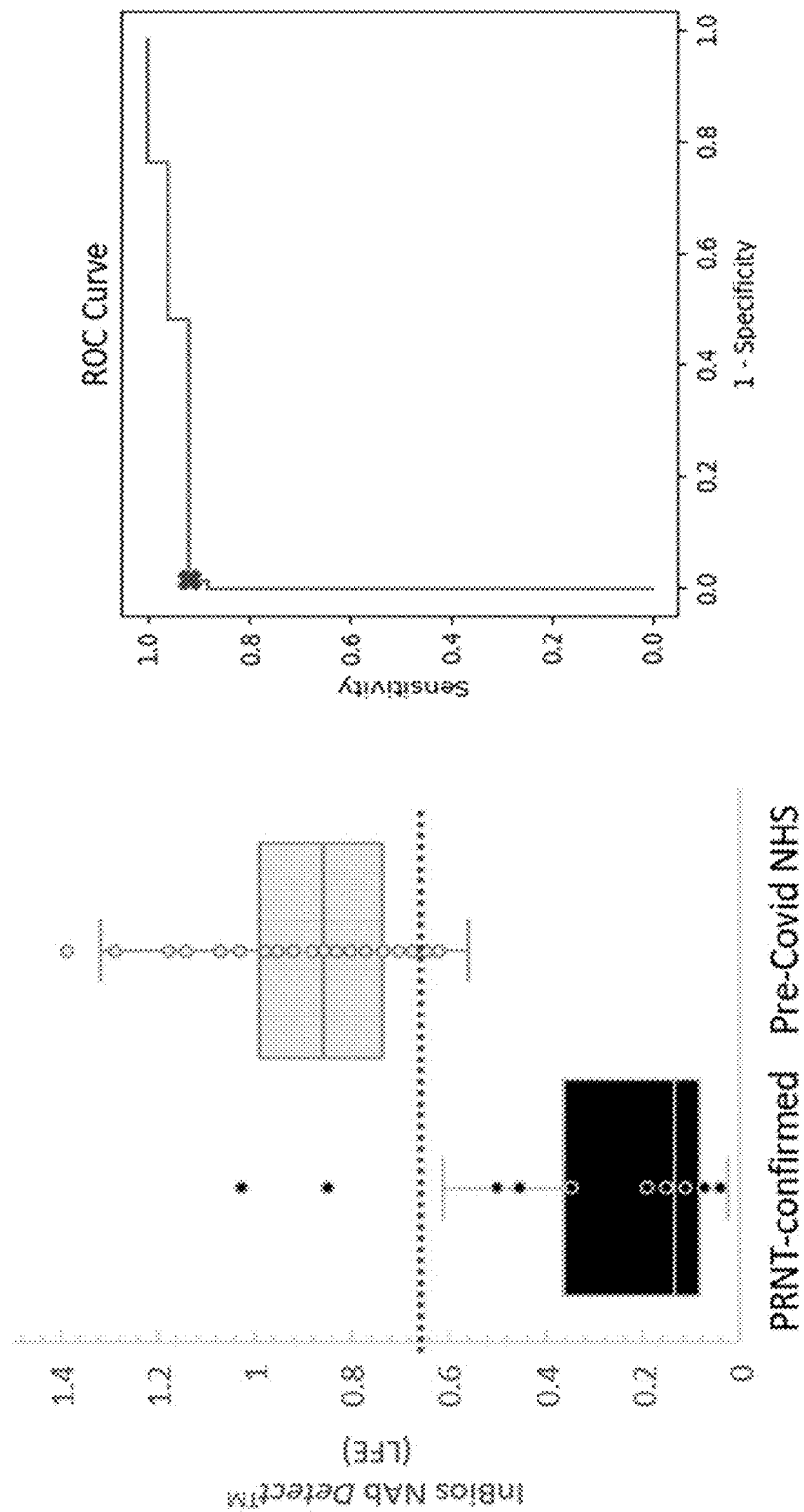
FIG. 14 depicts the distribution of SARS-CoV-2 plaque reduction neutralization test (PRNT)-confirmed positive and negative samples determined using a lateral flow assay cassette of the present disclosure and its corresponding receiver operator characteristic (ROC) curve (10 µl sample loading volume). LEFT: The box plots show the median values for each group, PRNT-confirmed serum specimens (n=25, black circles) and pre-Covid collected serum specimens (n=64, gray circles). RIGHT: Optimal cut-off LFE determined by ROC curve (bootstrap ROC analysis) is 0.63 and shown as a dashed red line.
Figure 15:
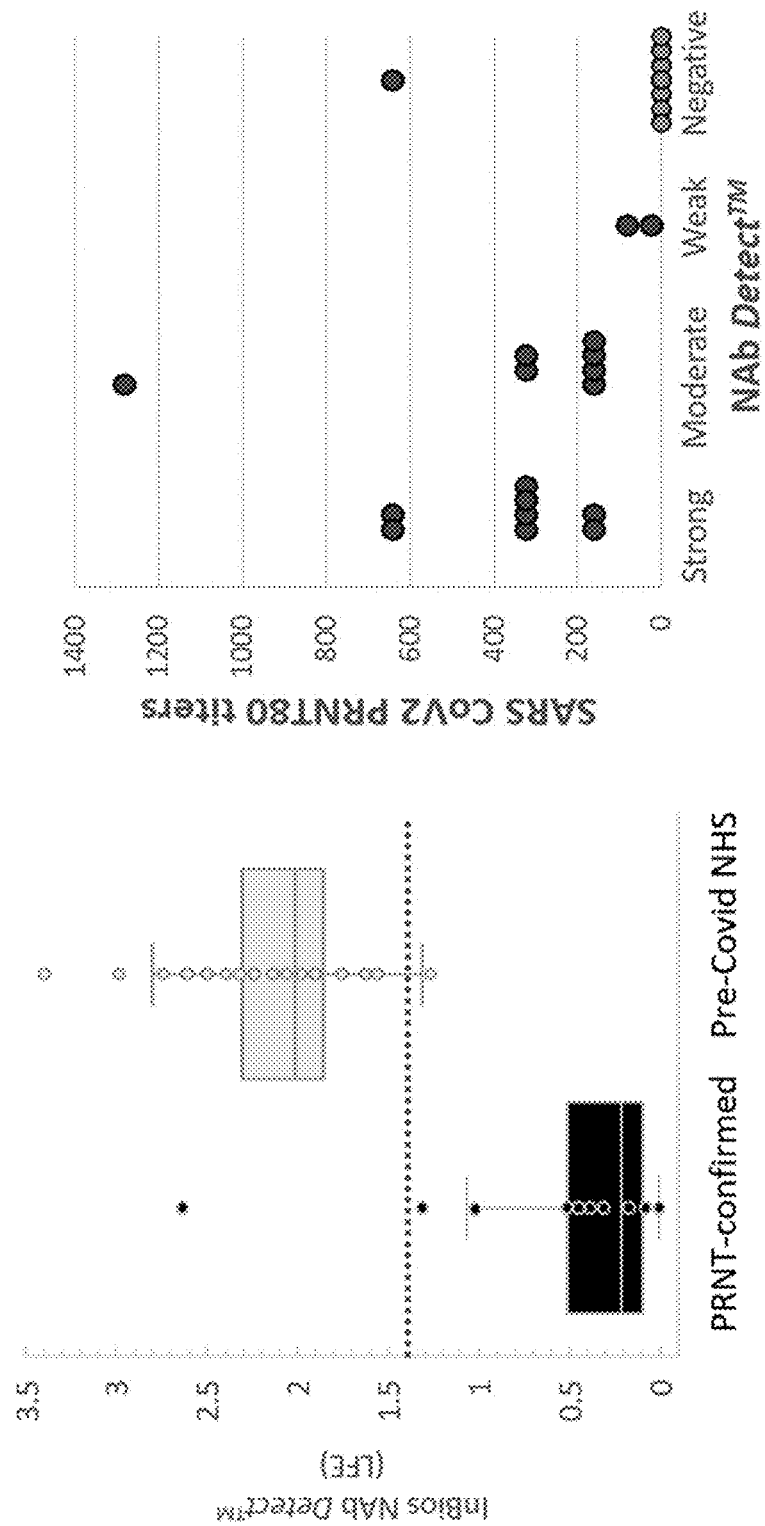
FIG. 15 depicts the distribution of SARS-CoV-2 PRNT-confirmed positive and negative samples determined using a lateral flow assay cassette of the present disclosure (50 µl sample size). LEFT: Box plots show median values for PRNT-confirmed serum specimens (n=18, black circles) and pre-Covid collected serum specimens (n=39, gray circles). Optimal cut-off LFE determined by ROC curve analysis is 1.4 (dashed red line). RIGHT: Comparison of PRNT80 titers with NAb Detect™ categories. Red=positive samples, green=negative samples.

Using example lateral flow assay cassettes and a calibration curve generated using mAbs directed to the Spike RBD (positive samples) or to remote sites of the protein (negative samples), samples were tested an compared to PRNT results (FIG. 14 and FIG. 15).

Specifically, to evaluate the signal intensity difference between negative and positive samples, a panel of 64 commercially acquired serum samples collected before November 2019 (before the emergence of SARS-CoV-2) and a panel of 25 qPCR/PRNT-confirmed COVID-19 positive plasma specimens (N=89) were tested using a lateral flow assay cassette for SARS-CoV-2.

There was a clear signal difference between the positive samples (black circles) and the negative samples (gray circles) (FIG. 14). The resulting LFEs were used to generate a ROC curve and identify an optimal cut-off of 0.63 LFE for the test lot. The estimated positive percent agreement (PPA) was 92% and the negative percent agreement (NPA) was 96.9%.

From the PRNT-confirmed specimens, defined LFE ranges were used to establish the semi-quantitative result categories of strong, moderate, and weak positives. Because the strongest samples generated LFEs of <0.2, this value was set as the threshold value for strong samples. The remaining distribution was divided in half such that LFEs>0.2 to 0.42 were classified as moderate positives, and >0.42 to <0.63 are classified as weak positives.

Separate panels of SARS CoV-2 PRNT-confirmed specimens (n=18) and pre-Covid-collected serum samples (n=39) were also. PRNT-confirmed specimens were acquired commercially from naturally infected patients in the U.S. Samples were collected ~10-20 days post symptom onset and were qPCR-positive for SARS CoV-2. 50 µl samples were used and the optimal cut-off LFE was adjusted to 1.4 based on ROC analysis. Among the 18 PRNT-confirmed serum samples, 17 tested positives by the lateral flow assay cassette (FIG. 15).

These samples were categorized semi-quantitatively based on their LFE values (strong is LFE<0.2, moderate is >0.2 and <0.8, weak is >0.8 and <1.4). Overall, the lateral flow assay cassette-assigned categories trended well with PRNT80 titers, with some overlap between categories (FIG. 15). This assay had PPA of 94.4% and NPA of 97.4%.

Representative images of the visual results along with PRNT titers are shown in FIG. 16. The use of a smartphone app or other AI-assisted reader removes ambiguity in categorizing the rapid assay results.

Sample size was also evaluated to arrive at a recommended sample volume for the SARS-CoV-2 nAb lateral flow assay. Four samples (Pre-Covid normal human serum, qPCR-confirmed naturally Covid-infected human serum, and serum from a SCoV-2 fully vaccinated (Moderna) individual diluted 1:5 in a pre-Covid serum) were tested at different loading volumes (10, 20, and 50 µl). Among samples containing anti-SCoV-2 NAbs, LFEs varied minimally among sample volumes (FIG. 17). However, for the Pre-Covid NHS sample, the signal increased with increased sample volume, which dramatically enhanced signal intensity separation between positive and negative samples (FIG. 17). Thus, larger sample volumes improved sensitivity for detecting weakly positive samples.

Sources of assay variability include the reagents, assembly/lamination, operator-to-operator variability, and the type of device used to run the smartphone app reader, but device-to-device variability using three Android devices (OnePlus, Pixel 4a, and Moto G7) was, and the T:C/LFE ratios were consistent and appropriately scaled the signal intensity with different camera types.

The coefficient of variation of the control line peak value does not vary more than 17% among the samples screened thus far (N=89).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An enzyme-linked immunosorbent assay (ELISA) method of detecting antibodies that are neutralizing for SARS-CoV-2 Spike protein binding to human angiotensin-converting enzyme 2 (ACE2), the method comprising:
combining full-length SARS-CoV-2 Spike protein ectodomain with a strep tag protein label at one terminus and an anti-strep tag protein label antibody bound to the strep tag with a sample comprising antibodies to form a mixture;
incubating the mixture with a human ACE2 protein ectodomain bound to a substrate for a length of time sufficient to allow the full-length SARS-CoV-2 Spike protein to bind the human ACE2 protein ectodomain;
incubating the substrate with a detection antibody that specifically binds a constant region of the anti-strep tag protein label antibody and comprises a detection label for a length of time sufficient for the detection antibody to bind to the anti-strep tag protein label antibody;
washing the substrate to remove SARS-CoV-2 Spike protein ectodomain with a strep tag protein label at one terminus, anti-strep tag protein label antibody, and detection antibody not bound to the human ACE2 protein ectodomain;
incubating the substrate with an enzymatic substrate; and
measuring the amount of anti-strep tag protein label antibody associated with the substrate as compared to a negative control by measuring an amount of the detection label;
wherein a reduced amount of detection label as compared to the negative control indicates the presence of antibodies in the sample that are neutralizing for SARS-CoV-2 Spike protein binding to human ACE2.

2. An enzyme-linked immunosorbent assay (ELISA) method of detecting antibodies that are neutralizing for SARS-CoV-2 Spike protein binding to human angiotensin-converting enzyme 2 (ACE2), the method comprising:
combining full-length SARS-CoV-2 Spike protein ectodomain with a strep tag protein label at one terminus and an anti-strep tag protein label antibody bound to the strep tag with a sample comprising antibodies to form a mixture;
incubating the mixture with a human ACE2 protein ectodomain bound to a substrate for a length of time sufficient to allow the full-length SARS-CoV-2 Spike protein to bind the human ACE2 protein ectodomain;
incubating the substrate with a detection antibody that specifically binds a constant region of the anti-strep tag protein label antibody and comprises an enzymatic detection label for a length of time sufficient for the detection antibody to bind to the anti-strep tag protein label antibody;
washing the substrate to remove SARS-CoV-2 Spike protein ectodomain with a strep tag protein at one terminus, anti-strep tag protein label antibody, and detection antibody not bound to the human ACE2 protein ectodomain;
incubating the substrate with an enzymatic substrate for a length of time sufficient for the enzymatic detection label to catalyze a reaction with the enzymatic substrate to produce a fluorescent or color reaction product; and
measuring the amount of anti-strep tag protein label antibody associated with the substrate as compared to a negative control by measuring an amount of a fluorescent or color reaction product;
wherein a reduced amount of fluorescent or color reaction product as compared to the negative control indicates the presence of antibodies in the sample that are neutralizing for SARS-CoV-2 Spike protein binding to human ACE2.

3. The method of claim 2, wherein the full-length Spike protein ectodomain comprises the amino acid sequence according to SEQ ID NO:1.

4. The method of claim 2, wherein the strep tag comprises the amino acid sequence according to SEQ ID NO: 6 or SEQ ID NO: 7.

5. The method of claim 2, wherein the full-length SARS-CoV-2 Spike protein ectodomain with a strep tag protein label at one terminus is a fusion protein comprising the full-length SARS-CoV-2 Spike protein ectodomain and the strep tag protein label.

6. The method of claim 5, wherein the fusion protein comprises the amino acid sequence according to SEQ ID NO: 4.

7. The method of claim 2, wherein the human ACE2 protein ectodomain comprises the amino acid sequence according to SEQ ID NO: 3.

8. The method of claim 2, wherein the human ACE2 protein ectodomain is comprised in an ACE2-Fc fusion protein that further comprises an immunoglobulin constant region (Fc).

9. The method of claim 8, wherein the ACE2-Fc fusion protein comprises the amino acid sequence according to SEQ ID NO: 5.

10. The method of claim 2, wherein measuring the amount of a reaction product resulting from action of the enzymatic detection label on the enzymatic substrate comprises measuring an optical density.

11. The method of claim 2, wherein the sample is blood, serum, or plasma.

12. The method of claim 11, further comprising diluting the sample 1:20 with a buffer comprising the full-length SARS-CoV-2 Spike protein ectodomain with a strep tag protein label at one terminus and an anti-strep tag protein label antibody.

13. The method of claim 2, further comprising washing the substrate between incubating the mixture with the human ACE2 protein ectodomain and incubating the human ACE2 protein ectodomain bound to a substrate with the detection antibody to remove SARS-CoV-2 Spike protein ectodomain with a strep tag protein at one terminus, and anti-strep tag protein label antibody not bound to the human ACE2 protein ectodomain.

14. The method of claim 2, further comprising adding a stop reagent to the substrate between adding the enzymatic substrate and measuring the amount of the fluorescent or color reaction product resulting from the action of the enzymatic detection label on the enzymatic substrate.

15. The method of claim 2, wherein the anti-strep tag protein label antibody comprises a constant region of the IgG1 isotype, the detection antibody comprises an anti-IgG1 antibody, the detection label comprises horseradish peroxidase (HRP), the enzymatic substrate comprises a colorimetric HRP substrate, and measuring the amount of a fluorescent or color reaction product comprises measuring optical density of the sample and at a wavelength of 450 nm ($OD_{450}$) to obtain a sample OD, and
the method further comprising measuring $OD_{450}$ of the negative control to obtain a negative control OD.

16. The method of claim 15, further comprising calculating a signal inhibition percent (SI %) for the sample using the following formula: SI %=(1−(sample OD÷negative control OD))×100%.

17. The method of claim 16, wherein, if the SI % is greater than 25%, the sample is positive for antibodies that are neutralizing for SARS-CoV-2 Spike protein binding to human ACE2, if the SI % is between 15% and 25%, the sample is inconclusive for antibodies that are neutralizing for SARS-CoV-2 Spike protein binding to human ACE2, and, if the SI % is less than 15%, the sample is negative for antibodies that are neutralizing for SARS-CoV-2 Spike protein binding to human ACE2.

\* \* \* \* \*

SEQUENCE LISTING

<160> NUMBER OF SEQ ID NOS: 18

<210> SEQ ID NO 1
<211> LENGTH: 1273
<212> TYPE: PRT
<213> ORGANISM: betacoronavirus SARS coronavirus 2

<400> SEQUENCE: 1

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125
```

-continued

```
Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
```

-continued

```
            545                 550                 555                 560
        Pro Phe Gln Gln Phe Gly Arg Asp Ile Ala Asp Thr Thr Asp Ala Val
                        565                 570                 575
        Arg Asp Pro Gln Thr Leu Glu Ile Leu Asp Ile Thr Pro Cys Ser Phe
                        580                 585                 590
        Gly Gly Val Ser Val Ile Thr Pro Gly Thr Asn Thr Ser Asn Gln Val
                        595                 600                 605
        Ala Val Leu Tyr Gln Asp Val Asn Cys Thr Glu Val Pro Val Ala Ile
                        610                 615                 620
        His Ala Asp Gln Leu Thr Pro Thr Trp Arg Val Tyr Ser Thr Gly Ser
        625                 630                 635                 640
        Asn Val Phe Gln Thr Arg Ala Gly Cys Leu Ile Gly Ala Glu His Val
                        645                 650                 655
        Asn Asn Ser Tyr Glu Cys Asp Ile Pro Ile Gly Ala Gly Ile Cys Ala
                        660                 665                 670
        Ser Tyr Gln Thr Gln Thr Asn Ser Pro Arg Arg Ala Arg Ser Val Ala
                        675                 680                 685
        Ser Gln Ser Ile Ile Ala Tyr Thr Met Ser Leu Gly Ala Glu Asn Ser
                        690                 695                 700
        Val Ala Tyr Ser Asn Asn Ser Ile Ala Ile Pro Thr Asn Phe Thr Ile
        705                 710                 715                 720
        Ser Val Thr Thr Glu Ile Leu Pro Val Ser Met Thr Lys Thr Ser Val
                        725                 730                 735
        Asp Cys Thr Met Tyr Ile Cys Gly Asp Ser Thr Glu Cys Ser Asn Leu
                        740                 745                 750
        Leu Leu Gln Tyr Gly Ser Phe Cys Thr Gln Leu Asn Arg Ala Leu Thr
                        755                 760                 765
        Gly Ile Ala Val Glu Gln Asp Lys Asn Thr Gln Glu Val Phe Ala Gln
                        770                 775                 780
        Val Lys Gln Ile Tyr Lys Thr Pro Pro Ile Lys Asp Phe Gly Gly Phe
        785                 790                 795                 800
        Asn Phe Ser Gln Ile Leu Pro Asp Pro Ser Lys Pro Ser Lys Arg Ser
                        805                 810                 815
        Phe Ile Glu Asp Leu Leu Phe Asn Lys Val Thr Leu Ala Asp Ala Gly
                        820                 825                 830
        Phe Ile Lys Gln Tyr Gly Asp Cys Leu Gly Asp Ile Ala Ala Arg Asp
                        835                 840                 845
        Leu Ile Cys Ala Gln Lys Phe Asn Gly Leu Thr Val Leu Pro Pro Leu
                        850                 855                 860
        Leu Thr Asp Glu Met Ile Ala Gln Tyr Thr Ser Ala Leu Leu Ala Gly
        865                 870                 875                 880
        Thr Ile Thr Ser Gly Trp Thr Phe Gly Ala Gly Ala Ala Leu Gln Ile
                        885                 890                 895
        Pro Phe Ala Met Gln Met Ala Tyr Arg Phe Asn Gly Ile Gly Val Thr
                        900                 905                 910
        Gln Asn Val Leu Tyr Glu Asn Gln Lys Leu Ile Ala Asn Gln Phe Asn
                        915                 920                 925
        Ser Ala Ile Gly Lys Ile Gln Asp Ser Leu Ser Ser Thr Ala Ser Ala
                        930                 935                 940
        Leu Gly Lys Leu Gln Asp Val Val Asn Gln Asn Ala Gln Ala Leu Asn
        945                 950                 955                 960
        Thr Leu Val Lys Gln Leu Ser Ser Asn Phe Gly Ala Ile Ser Ser Val
                        965                 970                 975
```

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu  Gln Thr Tyr Val
            995                 1000                1005

Thr Gln  Gln Leu Ile Arg Ala  Ala Glu Ile Arg Ala  Ser Ala Asn
         1010                1015                1020

Leu Ala  Ala Thr Lys Met Ser  Glu Cys Val Leu Gly  Gln Ser Lys
         1025                1030                1035

Arg Val  Asp Phe Cys Gly Lys  Gly Tyr His Leu Met  Ser Phe Pro
         1040                1045                1050

Gln Ser  Ala Pro His Gly Val  Val Phe Leu His Val  Thr Tyr Val
         1055                1060                1065

Pro Ala  Gln Glu Lys Asn Phe  Thr Thr Ala Pro Ala  Ile Cys His
         1070                1075                1080

Asp Gly  Lys Ala His Phe Pro  Arg Glu Gly Val Phe  Val Ser Asn
         1085                1090                1095

Gly Thr  His Trp Phe Val Thr  Gln Arg Asn Phe Tyr  Glu Pro Gln
         1100                1105                1110

Ile Ile  Thr Thr Asp Asn Thr  Phe Val Ser Gly Asn  Cys Asp Val
         1115                1120                1125

Val Ile  Gly Ile Val Asn Asn  Thr Val Tyr Asp Pro  Leu Gln Pro
         1130                1135                1140

Glu Leu  Asp Ser Phe Lys Glu  Glu Leu Asp Lys Tyr  Phe Lys Asn
         1145                1150                1155

His Thr  Ser Pro Asp Val Asp  Leu Gly Asp Ile Ser  Gly Ile Asn
         1160                1165                1170

Ala Ser  Val Val Asn Ile Gln  Lys Glu Ile Asp Arg  Leu Asn Glu
         1175                1180                1185

Val Ala  Lys Asn Leu Asn Glu  Ser Leu Ile Asp Leu  Gln Glu Leu
         1190                1195                1200

Gly Lys  Tyr Glu Gln Tyr Ile  Lys Trp Pro Trp Tyr  Ile Trp Leu
         1205                1210                1215

Gly Phe  Ile Ala Gly Leu Ile  Ala Ile Val Met Val  Thr Ile Met
         1220                1225                1230

Leu Cys  Cys Met Thr Ser Cys  Cys Ser Cys Leu Lys  Gly Cys Cys
         1235                1240                1245

Ser Cys  Gly Ser Cys Cys Lys  Phe Asp Glu Asp Asp  Ser Glu Pro
         1250                1255                1260

Val Leu  Lys Gly Val Lys Leu  His Tyr Thr
         1265                1270

<210> SEQ ID NO 2
<211> LENGTH: 229
<212> TYPE: PRT
<213> ORGANISM: betacoronavirus SARS coronavirus 2

<400> SEQUENCE: 2

Arg Val Gln Pro Thr Glu Ser Ile Val Arg Phe Pro Asn Ile Thr Asn
1               5                   10                  15

Leu Cys P

```
            50                  55                  60
Ser Pro Thr Lys Leu Asn Asp Leu Cys Phe Thr Asn Val Tyr Ala Asp
 65                  70                  75                  80

Ser Phe Val Ile Arg Gly Asp Glu Val Arg Gln Ile Ala Pro Gly Gln
                 85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
            195                 200                 205

Pro Lys Lys Ser Thr Asn Leu Val Lys Asn Lys Cys Val Asn Phe His
210                 215                 220

His His His His
225

<210> SEQ ID NO 3
<211> LENGTH: 805
<212> TYPE: PRT
<213> ORGANISM: Homo sapiens

<400> SEQUENCE: 3

Met Ser Ser Ser Trp Leu Leu Leu Ser Leu Val Ala Val Thr Ala Ala
 1               5                  10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
 50                  55                  60

Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190
```

```
Ala Asn His Tyr Glu Asp Tyr Gly Asp Tyr Trp Arg Gly Asp Tyr Glu
        195             200             205
Val Asn Gly Val Asp Gly Tyr Asp Tyr Ser Arg Gly Gln Leu Ile Glu
    210             215             220
Asp Val Glu His Thr Phe Glu Glu Ile Lys Pro Leu Tyr Glu His Leu
225             230             235             240
His Ala Tyr Val Arg Ala Lys Leu Met Asn Ala Tyr Pro Ser Tyr Ile
                245             250             255
Ser Pro Ile Gly Cys Leu Pro Ala His Leu Leu Gly Asp Met Trp Gly
            260             265             270
Arg Phe Trp Thr Asn Leu Tyr Ser Leu Thr Val Pro Phe Gly Gln Lys
        275             280             285
Pro Asn Ile Asp Val Thr Asp Ala Met Val Asp Gln Ala Trp Asp Ala
    290             295             300
Gln Arg Ile Phe Lys Glu Ala Glu Lys Phe Phe Val Ser Val Gly Leu
305             310             315             320
Pro Asn Met Thr Gln Gly Phe Trp Glu Asn Ser Met Leu Thr Asp Pro
                325             330             335
Gly Asn Val Gln Lys Ala Val Cys His Pro Thr Ala Trp Asp Leu Gly
            340             345             350
Lys Gly Asp Phe Arg Ile Leu Met Cys Thr Lys Val Thr Met Asp Asp
        355             360             365
Phe Leu Thr Ala His His Glu Met Gly His Ile Gln Tyr Asp Met Ala
    370             375             380
Tyr Ala Ala Gln Pro Phe Leu Leu Arg Asn Gly Ala Asn Glu Gly Phe
385             390             395             400
His Glu Ala Val Gly Glu Ile Met Ser Leu Ser Ala Ala Thr Pro Lys
                405             410             415
His Leu Lys Ser Ile Gly Leu Leu Ser Pro Asp Phe Gln Glu Asp Asn
            420             425             430
Glu Thr Glu Ile Asn Phe Leu Leu Lys Gln Ala Leu Thr Ile Val Gly
        435             440             445
Thr Leu Pro Phe Thr Tyr Met Leu Glu Lys Trp Arg Trp Met Val Phe
    450             455             460
Lys Gly Glu Ile Pro Lys Asp Gln Trp Met Lys Lys Trp Trp Glu Met
465             470             475             480
Lys Arg Glu Ile Val Gly Val Val Glu Pro Val His Asp Glu Thr
                485             490             495
Tyr Cys Asp Pro Ala Ser Leu Phe His Val Ser Asn Asp Tyr Ser Phe
            500             505             510
Ile Arg Tyr Tyr Thr Arg Thr Leu Tyr Gln Phe Gln Phe Gln Glu Ala
        515             520             525
Leu Cys Gln Ala Ala Lys His Glu Gly Pro Leu His Lys Cys Asp Ile
    530             535             540
Ser Asn Ser Thr Glu Ala Gly Gln Lys Leu Phe Asn Met Leu Arg Leu
545             550             555             560
Gly Lys Ser Glu Pro Trp Thr Leu Ala Leu Glu Asn Val Val Gly Ala
                565             570             575
Lys Asn Met Asn Val Arg Pro Leu Leu Asn Tyr Phe Glu Pro Leu Phe
            580             585             590
Thr Trp Leu Lys Asp Gln Asn Lys Asn Ser Phe Val Gly Trp Ser Thr
        595             600             605
Asp Trp Ser Pro Tyr Ala Asp Gln Ser Ile Lys Val Arg Ile Ser Leu
```

610                 615                 620
Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Phe Val Thr Ala Pro
                675                 680                 685

Lys Asn Val Ser Asp Ile Ile Pro Arg Thr Glu Val Glu Lys Ala Ile
                690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
                740                 745                 750

Ile Val Val Gly Ile Val Ile Leu Ile Phe Thr Gly Ile Arg Asp Arg
                755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 4
<211> LENGTH: 1296
<212> TYPE: PRT
<213> ORGANISM: Artificial Sequence
<220> FEATURE:
<223> OTHER INFORMATION: Synthetic sequence SARS-CoV-2 Spike protein
      streptavidin fusion protein

<400> SEQUENCE: 4

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

```
Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
        180                 185                 190

Val Phe Lys Asn Ile Asp Gly Tyr Phe Lys Ile Tyr Ser Lys His Thr
    195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Tyr Tyr Val Gly Tyr Leu Gln Pro
        260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
        340                 345                 350

Trp Asn Arg Lys Arg Ile Ser Asn Cys Val Ala Asp Tyr Ser Val Leu
    355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
        420                 425                 430

Val Ile Ala Trp Asn Ser Asn Asn Leu Asp Ser Lys Val Gly Gly Asn
    435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
        500                 505                 510

Leu Ser Phe Glu Leu Leu His Ala Pro Ala Thr Val Cys Gly Pro Lys
    515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
```

```
                580                 585                 590
Gly Gly Val Ser Val Ile Thr Pro Gly Thr Asn Thr Ser Asn Gln Val
            595                 600                 605
Ala Val Leu Tyr Gln Asp Val Asn Cys Thr Glu Val Pro Val Ala Ile
            610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
            645                 650                 655
Asn Asn Ser Tyr Glu Cys Asp Ile Pro Ile Gly Ala Gly Ile Cys Ala
            660                 665                 670
Ser Tyr Gln Thr Gln Thr Asn Ser Pro Ser Ser Ala Ser Ser Val Ala
            675                 680                 685
Ser Gln Ser Ile Ile Ala Tyr Thr Met Ser Leu Gly Ala Glu Asn Ser
            690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
            725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
            755                 760                 765
Gly Ile Ala Val Glu Gln Asp Lys Asn Thr Gln Glu Val Phe Ala Gln
            770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
            805                 810                 815
Phe Ile Glu Asp Leu Leu Phe Asn Lys Val Thr Leu Ala Asp Ala Gly
            820                 825                 830
Phe Ile Lys Gln Tyr Gly Asp Cys Leu Gly Asp Ile Ala Ala Arg Asp
            835                 840                 845
Leu Ile Cys Ala Gln Lys Phe Asn Gly Leu Thr Val Leu Pro Pro Leu
850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
            885                 890                 895
Pro Phe Ala Met Gln Met Ala Tyr Arg Phe Asn Gly Ile Gly Val Thr
            900                 905                 910
Gln Asn Val Leu Tyr Glu Asn Gln Lys Leu Ile Ala Asn Gln Phe Asn
            915                 920                 925
Ser Ala Ile Gly Lys Ile Gln Asp Ser Leu Ser Ser Thr Ala Ser Ala
            930                 935                 940
Leu Gly Lys Leu Gln Asp Val Val Asn Gln Asn Ala Gln Ala Leu Asn
945                 950                 955                 960
Thr Leu Val Lys Gln Leu Ser Ser Asn Phe Gly Ala Ile Ser Ser Val
            965                 970                 975
Leu Asn Asp Ile Leu Ser Arg Leu Asp Pro Pro Glu Ala Glu Val Gln
            980                 985                 990
Ile Asp Arg Leu Ile Thr Gly Arg  Leu Gln Ser Leu  Gln Thr Tyr Val
            995                 1000                1005
```

```
Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Gly Gly Gly Ser Gly Glu
    1205                1210                1215

Asn Leu Tyr Phe Gln Gly Gly Tyr Ile Pro Glu Ala Pro Arg Asp
    1220                1225                1230

Gly Gln Ala Tyr Val Arg Lys Asp Gly Glu Trp Val Leu Leu Ser
    1235                1240                1245

Thr Phe Leu Gly Gly Gly Gly Ser His His His His His His Ser
    1250                1255                1260

Ser Gly Trp Ser His Pro Gln Phe Glu Lys Gly Gly Ser Gly
    1265                1270                1275

Gly Gly Ser Gly Gly Ser Gly Trp Ser His Pro Gln Phe Glu Lys
    1280                1285                1290

Gly Gly Ser
    1295

<210> SEQ ID NO 5
<211> LENGTH: 847
<212> TYPE: PRT
<213> ORGANISM: Artificial Sequence
<220> FEATURE:
<223> OTHER INFORMATION: Synthetic sequence ACE2-IgG fusion protein

<400> SEQUENCE: 5

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45
```

-continued

```
Asn Tyr Asn Thr Asn Ile Thr Glu Glu Asn Val Gln Asn Met Asn Asn
         50                  55                  60
Ala Gly Asp Lys Trp Ser Ala Phe Leu Lys Glu Gln Ser Thr Leu Ala
 65                  70                  75                  80
Gln Met Tyr Pro Leu Gln Glu Ile Gln Asn Leu Thr Val Lys Leu Gln
                         85                  90                  95
Leu Gln Ala Leu Gln Gln Asn Gly Ser Ser Val Leu Ser Glu Asp Lys
                    100                 105                 110
Ser Lys Arg Leu Asn Thr Ile Leu Asn Thr Met Ser Thr Ile Tyr Ser
             115                 120                 125
Thr Gly Lys Val Cys Asn Pro Asp Asn Pro Gln Glu Cys Leu Leu Leu
    130                 135                 140
Glu Pro Gly Leu Asn Glu Ile Met Ala Asn Ser Leu Asp Tyr Asn Glu
145                 150                 155                 160
Arg Leu Trp Ala Trp Glu Ser Trp Arg Ser Glu Val Gly Lys Gln Leu
                165                 170                 175
Arg Pro Leu Tyr Glu Glu Tyr Val Val Leu Lys Asn Glu Met Ala Arg
            180                 185                 190
Ala Asn His Tyr Glu Asp Tyr Gly Asp Tyr Trp Arg Gly Asp Tyr Glu
        195                 200                 205
Val Asn Gly Val Asp Gly Tyr Asp Tyr Ser Arg Gly Gln Leu Ile Glu
    210                 215                 220
Asp Val Glu His Thr Phe Glu Glu Ile Lys Pro Leu Tyr Glu His Leu
225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
            260                 265                 270
Arg Phe Trp Thr Asn Leu Tyr Ser Leu Thr Val Pro Phe Gly Gln Lys
        275                 280                 285
Pro Asn Ile Asp Val Thr Asp Ala Met Val Asp Gln Ala Trp Asp Ala
    290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
            340                 345                 350
Lys Gly Asp Phe Arg Ile Leu Met Cys Thr Lys Val Thr Met Asp Asp
        355                 360                 365
Phe Leu Thr Ala His His Glu Met Gly His Ile Gln Tyr Asp Met Ala
    370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
            420                 425                 430
Glu Thr Glu Ile Asn Phe Leu Leu Lys Gln Ala Leu Thr Ile Val Gly
        435                 440                 445
Thr Leu Pro Phe Thr Tyr Met Leu Glu Lys Trp Arg Trp Met Val Phe
    450                 455                 460
```

```
Lys Gly Glu Ile Pro Lys Asp Gln Trp Met Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
                515                 520                 525

Leu Cys Gln Ala Ala Lys His Glu Gly Pro Leu His Lys Cys Asp Ile
                530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
                595                 600                 605

Asp Trp Ser Pro Tyr Ala Asp Glu Pro Lys Ser Cys Asp Lys Thr His
                610                 615                 620

Thr Cys Pro Pro Cys Pro Ala Pro Glu Leu Leu Gly Gly Pro Ser Val
625                 630                 635                 640

Phe Leu Phe Pro Pro Lys Pro Lys Asp Thr Leu Met Ile Ser Arg Thr
                645                 650                 655

Pro Glu Val Thr Cys Val Val Val Asp Val Ser His Glu Asp Pro Glu
                660                 665                 670

Val Lys Phe Asn Trp Tyr Val Asp Gly Val Glu Val His Asn Ala Lys
                675                 680                 685

Thr Lys Pro Arg Glu Glu Gln Tyr Asn Ser Thr Tyr Arg Val Val Ser
                690                 695                 700

Val Leu Thr Val Leu His Gln Asp Trp Leu Asn Gly Lys Glu Tyr Lys
705                 710                 715                 720

Cys Lys Val Ser Asn Lys Ala Leu Pro Ala Pro Ile Glu Lys Thr Ile
                725                 730                 735

Ser Lys Ala Lys Gly Gln Pro Arg Glu Pro Gln Val Tyr Thr Leu Pro
                740                 745                 750

Pro Ser Arg Asp Glu Leu Thr Lys Asn Gln Val Ser Leu Thr Cys Leu
                755                 760                 765

Val Lys Gly Phe Tyr Pro Ser Asp Ile Ala Val Glu Trp Glu Ser Asn
                770                 775                 780

Gly Gln Pro Glu Asn Asn Tyr Lys Thr Thr Pro Pro Val Leu Asp Ser
785                 790                 795                 800

Asp Gly Ser Phe Phe Leu Tyr Ser Lys Leu Thr Val Asp Lys Ser Arg
                805                 810                 815

Trp Gln Gln Gly Asn Val Phe Ser Cys Ser Val Met His Glu Ala Leu
                820                 825                 830

His Asn His Tyr Thr Gln Lys Ser Leu Ser Leu Ser Pro Gly Lys
                835                 840                 845

<210> SEQ ID NO 6
<211> LENGTH: 8
<212> TYPE: PRT
<213> ORGANISM: Artificial Sequence
<220> FEATURE:
<223> OTHER INFORMATION: Synthetic sequence Strep-tag II
```

```
<400> SEQUENCE: 6

Trp Ser His Pro Gln Phe Glu Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic sequence Strep-tag

<400> SEQUENCE: 7

Trp Ser Ala Pro Gln Phe Glu Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic sequence FLAG-1

<400> SEQUENCE: 8

Asp Tyr Lys Asp Asp Asp Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic sequence 6 x His

<400> SEQUENCE: 9

His His His His His His
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic sequence HA

<400> SEQUENCE: 10

Tyr Pro Tyr Asp Val Pro Asp Tyr Ala
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic sequence c-myc

<400> SEQUENCE: 11

Glu Gln Lys Leu Ile Ser Glu Glu Asp Leu
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Synthetic sequence Avitag
```

<400> SEQUENCE: 12

Gly Leu Asn Asp Ile Phe Glu Ala Gln Lys Ile Glu Trp His Glu
1               5                   10                  15

<210> SEQ ID NO 13
<211> LENGTH: 220
<212> TYPE: PRT
<213> ORGANISM: Artificial Sequence
<220> FEATURE:
<223> OTHER INFORMATION: Synthetic sequence GST

<400> SEQUENCE: 13

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp
    210                 215                 220

<210> SEQ ID NO 14
<211> LENGTH: 387
<212> TYPE: PRT
<213> ORGANISM: Artificial Sequence
<220> FEATURE:
<223> OTHER INFORMATION: Synthetic sequence MBP

<400> SEQUENCE: 14

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg
385

<210> SEQ ID NO 15
<211> LENGTH: 15
<212> TYPE: PRT
<213> ORGANISM: Artificial Sequence
<220> FEATURE:
<223> OTHER INFORMATION: Synthetic sequence S-tag

<400> SEQUENCE: 15

Lys Glu Thr Ala Ala Ala Lys Phe Glu Arg Gln His Met Asp Ser
1               5                   10                  15

<210> SEQ ID NO 16
<211> LENGTH: 26

```
<212> TYPE: PRT
<213> ORGANISM: Artificial Sequence
<220> FEATURE:
<223> OTHER INFORMATION: Synthetic sequence CBP

<400> SEQUENCE: 16

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 17
<211> LENGTH: 185
<212> TYPE: PRT
<213> ORGANISM: Artificial Sequence
<220> FEATURE:
<223> OTHER INFORMATION: Synthetic sequence TAP

<400> SEQUENCE: 17

Gly Arg Arg Ile Pro Gly Leu Ile Asn Pro Trp Lys Arg Arg Trp Lys
1               5                   10                  15

Lys Asn Phe Ile Ala Val Ser Ala Ala Asn Arg Phe Lys Lys Ile Ser
            20                  25                  30

Ser Ser Gly Ala Leu Asp Tyr Asp Ile Pro Thr Thr Ala Ser Glu Asn
        35                  40                  45

Leu Tyr Phe Gln Gly Glu Phe Gly Leu Ala Gln His Asp Glu Ala Val
    50                  55                  60

Asp Asn Lys Phe Asn Lys Glu Gln Gln Asn Ala Phe Tyr Glu Ile Leu
65              70                  75                  80

His Leu Pro Asn Leu Asn Glu Glu Gln Arg Asn Ala Phe Ile Gln Ser
                85                  90                  95

Leu Lys Asp Asp Pro Ser Gln Ser Ala Asn Leu Leu Ala Glu Ala Lys
            100                 105                 110

Lys Leu Asn Asp Ala Gln Ala Pro Lys Val Asp Asn Lys Phe Asn Lys
        115                 120                 125

Glu Gln Gln Asn Ala Phe Tyr Glu Ile Leu His Leu Pro Asn Leu Asn
    130                 135                 140

Glu Glu Gln Arg Asn Ala Phe Ile Gln Ser Leu Lys Asp Asp Pro Ser
145                 150                 155                 160

Gln Ser Ala Asn Leu Leu Ala Glu Ala Lys Lys Leu Asn Asp Ala Gln
                165                 170                 175

Ala Pro Lys Val Asp Ala Asn His Gln
            180                 185

<210> SEQ ID NO 18
<211> LENGTH: 14
<212> TYPE: PRT
<213> ORGANISM: Artificial Sequence
<220> FEATURE:
<223> OTHER INFORMATION: Synthetic sequence V5

<400> SEQUENCE: 18

Gly Lys Pro Ile Pro Asn Pro Leu Leu Gly Leu Asp Ser Thr
1               5                   10
```